United States Patent
Georg et al.

(10) Patent No.: US 11,780,828 B2
(45) Date of Patent: Oct. 10, 2023

(54) CONTRACEPTIVE COMPOUNDS AND METHODS

(71) Applicant: Regents of the University of Minnesota, Minneapolis, MN (US)

(72) Inventors: Ingrid Gunda Georg, Minneapolis, MN (US); Narsihmulu Cheryala, Minneapolis, MN (US)

(73) Assignee: REGENTS OF THE UNIVERSITY OF MINNESOTA, Minneapolis, MN (US)

( * ) Notice: Subject to any disclaimer, the term of this patent is extended or adjusted under 35 U.S.C. 154(b) by 0 days.

(21) Appl. No.: 17/735,918

(22) Filed: May 3, 2022

(65) Prior Publication Data
US 2022/0388993 A1 Dec. 8, 2022

Related U.S. Application Data

(60) Provisional application No. 63/326,524, filed on Apr. 1, 2022, provisional application No. 63/307,943, filed on Feb. 8, 2022, provisional application No. 63/184,014, filed on May 4, 2021.

(51) Int. Cl.
*C07D 405/04* (2006.01)
*A61P 15/16* (2006.01)

(52) U.S. Cl.
CPC ............ *C07D 405/04* (2013.01); *A61P 15/16* (2018.01)

(58) Field of Classification Search
CPC .............................. A61P 15/16; C07D 405/04
See application file for complete search history.

(56) References Cited

U.S. PATENT DOCUMENTS

| 6,110,959 A * | 8/2000 | Tagami | A61P 19/00 514/428 |
| 6,358,995 B1 * | 3/2002 | Tagami | A61P 19/00 562/490 |

FOREIGN PATENT DOCUMENTS

EP 0889032 A1 1/1999

OTHER PUBLICATIONS

Sanny S.W., et al., "Oral Administration of Retinoic Acid Receptor Antagonist Reversably Inhibits Spermatogenesis in Mice," Endocrinology, 152(6), 2492-2502 (2011).
Patent Cooperation Treaty, International Search Report and Written Opinion for PCT/US2022/027506, 11 pages, dated Aug. 25, 2022.

* cited by examiner

*Primary Examiner* — Nizal S Chandrakumar
(74) *Attorney, Agent, or Firm* — Viksnins Harris Padys Malen LLP

(57) ABSTRACT

The invention provides a compound of formula (I):

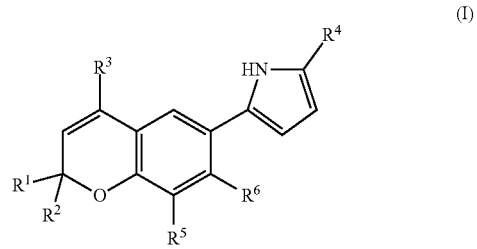

or a pharmaceutically acceptable salt, stereoisomer, solvate, or prodrug thereof, wherein $R^1$-$R^6$ have any of the values described in the specification, as well as compositions comprising a compound of formula (I). The compounds are useful as contraceptive agents.

17 Claims, 11 Drawing Sheets

CONTRACEPTIVE COMPOUNDS AND METHODS

CROSS REFERENCE TO RELATED APPLICATION

This application claims priority to U.S. Provisional Application No. 63/184,014, filed on 4 May 2021 and to U.S. Provisional Application No. 63/307,943, filed on 8 Feb. 2022, and to U.S. Provisional Application No. 63/326,524, filed on 1 Apr. 2022. The entire content of each of these United States Provisional applications is hereby incorporated by reference herein.

STATEMENT REGARDING FEDERALLY SPONSORED RESEARCH

This invention was made with government support under HD093540 and HHSN275201300017C awarded by National Institutes of Health. The government has certain rights in the invention.

BACKGROUND

Despite making progress worldwide in providing birth control options to families, the rate of unintended pregnancies, defined as both unwanted and mistimed pregnancies resulting from not using contraceptives or incorrect/inconsistent contraceptive use, remains high Bearak J., et al., 2018, Lancet Glob Health, 6, e380-e389). While rates of accidental pregnancies have decreased, the unintended pregnancy rates in developed nations are 45% and remain around 65% in developing nations Bearak J., et al., 2018, Lancet Glob Health, 6, e380-e389). Approximately 56% of all unintended pregnancies ended in abortion between 2010 and 2014-55% in developing nations and 59% in developed nations (Bearak J., et al., 2018, Lancet Glob Health, 6, e380-e389). There is thus a critical need for additional approaches and resources for reversible contraception. While many reversible contraceptive methods are available to women, such as hormonal birth control, emergency contraception, vaginal rings, cervical caps and spermicides, reversible methods for men are limited to condoms and withdrawal. For an in-depth reviews and discussions of male contraceptives, refer to Long J E., et al., 2019, Clin Chem, 65, 53-160; and Blithe D L., et al., 2016, Fertil Steril, 106, 1295-1302. There has been interest in the use of testosterone and various testosterone esters as potential contraceptive agents (Armory J K., et al., 2006, Nat Clin Pract Endocrinol Metab, 2, 32-41; and Page S T., et al., 2008, Endocr Rev, 29, 465-493); however, testosterone alone does not completely suppress sperm production, and there are ethnic differences in its efficacy (Armory J K., et al., 2006, Nat Clin Pract Endocrinol Metab, 2, 32-41; and Liu P Y., et al., 2008, J Clin Endocrinol Metab, 93, 1774-1783). Supplementation of testosterone administration with progestogens enhances the suppression of sperm production at lower doses of testosterone. However, the effects of long-term exogenous testosterone administration remain unclear. Treatment with testosterone has been associated with several negative side effects, which can include cardiac toxicity (Xu L., et al., 2013, BMC Medicine, 11, 108) and liver damage (Westaby D., et al., 1977, Lancet, 310, 261-263). The most common negative side effect was erythrocytosis, which has been linked to cerebrovascular disease (Coviello A D., et al., 2008, J Clin Endocrinol, 93, 914-919). Additionally, exogenous testosterone has been shown to lower HDL cholesterol and increase hematocrit, hemoglobin, and thromboxane, all of which are associated with cardiovascular disease (Xu L., et al., 2013, BMC Medicine, 11, 108). In addition to the more serious side effects, patients also experienced weight gain, acne, injection-site pain, and mood changes like aggression and decreased libido (World Health Organization Task Force on Methods for the Regulation of Male Fertility, 1990, Lancet, 336, 955-959). In the study described above, 2.2% of patients failed to reach the oligozoospermia threshold, indicating that certain men are "non-responders" to testosterone treatment (World Health Organization Task Force on Methods for the Regulation of Male Fertility, 1990, Lancet, 336, 955-959).

Therefore, a need exists for an effective, non-steroid hormone-based reversible male contraceptive that exhibits few if any side effects, health risks, and further complications. While hormone therapy relies on interrupting the spermatogenic process, there are far more targets for non-hormonal-based therapies that can be pursued (Blithe D., 2008, Contraception, 78, S23-S27). Non-hormonal male contraceptive approaches involve targeting proteins that affect either sperm production or sperm function and are anticipated to have minimal side effects, depending on the specificity and potency of inhibitors for the target protein.

SUMMARY

An effective, non-steroid hormone-based reversible male contraceptive that exhibits few if any side effects, health risks, or further complications has been identified. Accordingly, in one aspect the present invention provides a retinoic acid receptor-α antagonist compound of the invention, which is a compound of formula (I):

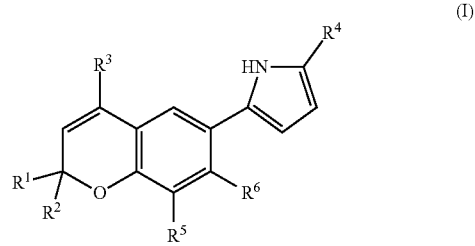

or a pharmaceutically-acceptable salt, stereoisomer, solvate, or prodrug thereof, wherein:

$R^1$ is H, $C_1$-$C_3$ alkyl, or halo$C_1$-$C_3$ alkyl;

$R^2$ is H, $C_1$-$C_3$ alkyl, or halo$C_1$-$C_3$ alkyl;

$R^3$ is $C_6$-$C_{10}$ aryl, 5-10 membered heteroaryl, $C_6$-$C_{10}$ aryl$C_1$-$C_3$ alkyl, or 5-10 membered heteroaryl$C_1$-$C_3$ alkyl, wherein any $C_6$-$C_{10}$ aryl, 5-10 membered heteroaryl, $C_6$-$C_{10}$ aryl$C_1$-$C_3$ alkyl, and 5-10 membered heteroaryl$C_1$-$C_3$ alkyl is optionally substituted with one or more groups independently selected from halo, cyano, nitro, carboxy, $C_1$-$C_6$ alkyl, $C_1$-$C_6$ alkoxy, $C_1$-$C_6$ alkanoyl, $C_1$-$C_6$ alkanoyloxy, $C_1$-$C_6$ alkoxycarbonyl, —$NR^aR^b$, or —$C(=O)NR^cR^d$, wherein any $C_1$-$C_6$ alkyl, $C_1$-$C_6$ alkoxy, $C_1$-$C_6$ alkanoyl, $C_1$-$C_6$ alkanoyloxy, and $C_1$-$C_6$ alkoxycarbonyl is optionally substituted with one or more groups independently selected from halo;

$R^4$ is $C_6$-$C_{10}$ aryl, 5-10 membered heteroaryl, $C_6$-$C_{10}$ aryl$C_1$-$C_3$ alkyl, or 5-10 membered heteroaryl$C_1$-$C_3$ alkyl, wherein any $C_6$-$C_{10}$ aryl, 5-10 membered heteroaryl, $C_6$-$C_{10}$ aryl$C_1$-$C_3$ alkyl, and 5-10 membered heteroaryl$C_1$-$C_3$ alkyl is substituted with carboxy and is further optionally substituted with one or more groups independently selected from halo, hydroxy, cyano, nitro, carboxy, $C_1$-$C_6$ alkyl, $C_1$-$C_6$ alkoxy, $C_1$-$C_6$ alkanoyl, $C_1$-$C_6$ alkanoyloxy, $C_1$-$C_6$ alkoxycarbonyl, —$NR^eR^f$, or —$C(=O)NR^gR^h$, wherein any $C_1$-$C_6$ alkyl, $C_1$-$C_6$ alkoxy, $C_1$-$C_6$ alkanoyl, $C_1$-$C_6$ alkanoyloxy, and $C_1$-$C_6$ alkoxycarbonyl is optionally substituted with one or more groups independently selected from halo;

$R^5$ is H, $C_1$-$C_3$ alkyl, hydroxy, $C_1$-$C_3$ alkoxy, halo or halo$C_1$-$C_3$ alkyl;

$R^6$ is H, $C_1$-$C_3$ alkyl, hydroxy, $C_1$-$C_3$ alkoxy, halo or halo$C_1$-$C_3$ alkyl;

each $R^a$ and $R^b$ is independently selected from the group consisting of H, $(C_1$-$C_6)$alkyl, $(C_3$-$C_6)$cycloalkyl, $(C_1$-$C_6)$alkanoyl, and $(C_3$-$C_6)$cycloalkyl$(C_1$-$C_6)$alkyl; or $R^a$ and $R^b$ together with the nitrogen to which they are attached form an aziridino, azetidino, morpholino, piperazino, pyrrolidino or piperidino ring, which ring is optionally substituted with one or more groups independently selected from $C_1$-$C_6$ alkyl and halo$C_1$-$C_6$ alkyl;

each $R^c$ and $R^d$ is independently selected from the group consisting of H, $(C_1$-$C_6)$alkyl, $(C_3$-$C_6)$cycloalkyl, $(C_1$-$C_6)$alkanoyl, and $(C_3$-$C_6)$cycloalkyl$(C_1$-$C_6)$alkyl; or $R^c$ and $R^d$ together with the nitrogen to which they are attached form an aziridino, azetidino, morpholino, piperazino, pyrrolidino or piperidino ring, which ring is optionally substituted with one or more groups independently selected from $C_1$-$C_6$ alkyl and halo$C_1$-$C_6$ alkyl;

each $R^e$ and $R^f$ is independently selected from the group consisting of H, $(C_1$-$C_6)$alkyl, $(C_3$-$C_6)$cycloalkyl, $(C_1$-$C_6)$alkanoyl, and $(C_3$-$C_6)$cycloalkyl$(C_1$-$C_6)$alkyl; or $R^e$ and $R^f$ together with the nitrogen to which they are attached form an aziridino, azetidino, morpholino, piperazino, pyrrolidino or piperidino ring, which ring is optionally substituted with one or more groups independently selected from $C_1$-$C_6$ alkyl and halo$C_1$-$C_6$ alkyl; and each $R^g$ and $R^h$ is independently selected from the group consisting of H, $(C_1$-$C_6)$alkyl, $(C_3$-$C_6)$cycloalkyl, $(C_1$-$C_6)$alkanoyl, and $(C_3$-$C_6)$cycloalkyl$(C_1$-$C_6)$alkyl; or $R^g$ and $R^h$ together with the nitrogen to which they are attached form an aziridino, azetidino, morpholino, piperazino, pyrrolidino or piperidino ring, which ring is optionally substituted with one or more groups independently selected from $C_1$-$C_6$ alkyl and halo$C_1$-$C_6$ alkyl.

The invention also provides a pharmaceutical composition comprising a compound of formula (I) or a pharmaceutically acceptable salt thereof, and a pharmaceutically acceptable excipient.

In another embodiment, the invention provides a method to reduce sperm count in a male subject, comprising administering a compound of formula (I) or a pharmaceutically acceptable salt thereof to the male subject (e.g., a human).

In another embodiment, the invention provides a method to produce reversible infertility in a male subject, comprising administering a compound of formula (I) or a pharmaceutically acceptable salt thereof to the male mammal (e.g., a human).

In another embodiment, the invention provides a method to reduce the likelihood of conception following intercourse between a male subject and a female subject, comprising administering a compound of formula (I) or a pharmaceutically acceptable salt thereof to the male subject (e.g., a human) prior to the intercourse.

In another embodiment, the invention provides a method for treating a disease or condition associated with RAR alpha activity in a subject wherein antagonism of RAR alpha is indicated, comprising administering a compound of formula (I) or a pharmaceutically acceptable salt thereof to the mammal.

In another embodiment, the invention provides a method for selectively antagonizing RAR alpha over RAR beta and RAR gamma in a subject, comprising administering a compound of formula (I) or a pharmaceutically acceptable salt thereof to the subject.

In another embodiment, the invention provides a method for selectively antagonizing RAR alpha over RAR beta and RAR gamma, comprising contacting RAR alpha, RAR beta, and RAR gamma in vitro with a compound of formula (I) or a salt thereof.

In another embodiment, the invention provides a compound of formula (I) or a pharmaceutically acceptable salt thereof for use in medical therapy.

In another embodiment, the invention provides a compound of formula (I) or a pharmaceutically acceptable salt thereof to reduce sperm count in a male subject.

In another embodiment, the invention provides a compound of formula (I) or a pharmaceutically acceptable salt thereof to produce reversible infertility in a male subject.

In another embodiment, the invention provides a compound of formula (I) or a pharmaceutically acceptable salt thereof to reduce the likelihood of conception following intercourse between a male subject and a female subject.

In another embodiment, the invention provides a compound of formula (I) or a pharmaceutically acceptable salt thereof to treating a disease or condition associated with RAR alpha activity.

In another embodiment, the invention provides a compound of formula (I) or a pharmaceutically acceptable salt thereof to selectively antagonize RAR alpha over RAR beta and RAR gamma in vitro.

In another embodiment, the invention provides the use of a compound of formula (I) or a pharmaceutically acceptable salt thereof to prepare a medicament to reduce sperm count in a male subject.

In another embodiment, the invention provides the use of a compound of formula (I) or a pharmaceutically acceptable salt thereof to prepare a medicament to produce reversible infertility in a male subject.

In another embodiment, the invention provides the use of a compound of formula (I) or a pharmaceutically acceptable salt thereof to prepare a medicament to reduce the likelihood of conception following intercourse between a male subject and a female subject.

In another embodiment, the invention provides the use of a compound of formula (I) or a pharmaceutically acceptable salt thereof to prepare a medicament treat a disease or condition associated with RAR alpha activity in a subject.

In another embodiment, the invention provides the use of a compound of formula (I) or a pharmaceutically acceptable salt thereof to prepare a medicament to selectively antagonize RAR alpha over RAR beta and RAR gamma in a subject.

In another embodiment, the invention provides a kit comprising packaging material that contains a compound of formula (I) or a pharmaceutically acceptable salt thereof, and instructions for use of the compound of formula (I) or a pharmaceutically acceptable salt thereof as a contraceptive (e.g., to reduce sperm count in a male subject, to produce reversible infertility in a male subject, and/or to reduce the likelihood of conception or eliminate the likelihood of conception).

In another embodiment, the invention provides a method to reduce sperm count in a male subject, comprising orally administering a compound that is a selective antagonist of RAR alpha or a pharmaceutically acceptable salt thereof to the male subject (e.g., a human).

In another embodiment, the invention provides a method to produce reversible infertility in a male subject, comprising administering a compound that is a selective antagonist of RAR alpha or a pharmaceutically acceptable salt thereof to the male subject (e.g., a human).

In another embodiment, the invention provides a method to reduce the likelihood of conception following intercourse between a male subject and a female subject, comprising administering a compound that is a selective antagonist of RAR alpha or a pharmaceutically acceptable salt thereof to the male subject (e.g., a human) prior to the intercourse.

In another embodiment, the invention provides a method for treating a disease or condition associated with RAR alpha activity in a subject wherein antagonism of RAR alpha is indicated, comprising administering a compound that is a selective antagonist of RAR alpha or a pharmaceutically acceptable salt thereof to the subject.

In another embodiment, the invention provides a compound that is orally active and a selective antagonist of RAR alpha or a pharmaceutically acceptable salt thereof to reduce sperm count in a male subject.

In another embodiment, the invention provides a compound that is orally active and a selective antagonist of RAR alpha or a pharmaceutically acceptable salt thereof to produce reversible infertility in a male subject.

In another embodiment, the invention provides a compound that is orally active and a selective antagonist of RAR alpha or a pharmaceutically acceptable salt thereof to reduce the likelihood of conception following intercourse between a male subject and a female subject.

In another embodiment, the invention provides a compound that is orally active and a selective antagonist of RAR alpha or a pharmaceutically acceptable salt thereof to treating a disease or condition associated with RAR alpha activity.

In another embodiment, the invention provides the use of a compound that is orally active and a selective antagonist of RAR alpha or a pharmaceutically acceptable salt thereof to prepare a medicament to reduce sperm count in a male subject.

In another embodiment, the invention provides the use of a compound that is orally active and a selective antagonist of RAR alpha or a pharmaceutically acceptable salt thereof to prepare a medicament to produce reversible infertility in a male subject.

In another embodiment, the invention provides the use of a compound that is orally active and a selective antagonist of RAR alpha or a pharmaceutically acceptable salt thereof to prepare a medicament to reduce the likelihood of conception following intercourse between a male subject and a female subject.

In another embodiment, the invention provides the use of a compound that is orally active and a selective antagonist of RAR alpha or a pharmaceutically acceptable salt thereof to prepare a medicament treat a disease or condition associated with RAR alpha activity in a subject.

The invention also provides processes and intermediates disclosed herein that are useful for preparing a compound of formula (I) or a pharmaceutically-acceptable salt, stereoisomer, solvate, or prodrug thereof.

DETAILED DESCRIPTION

Figure 1:
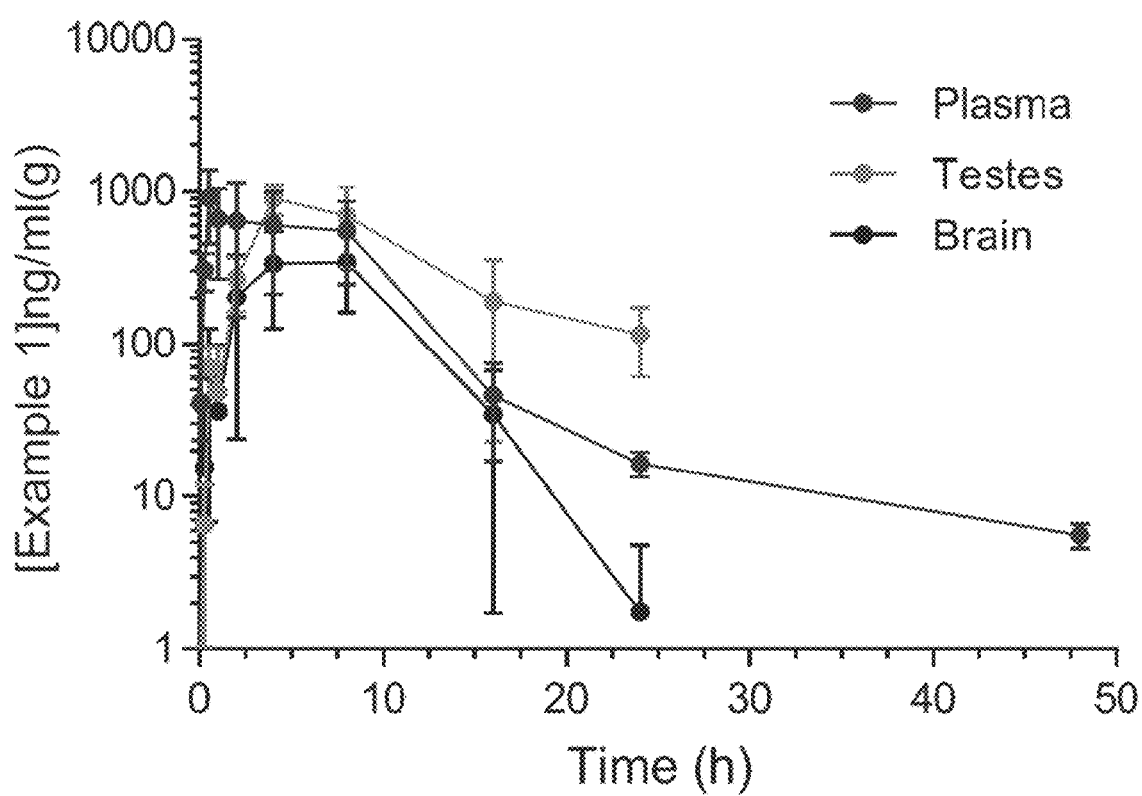
FIG. 1 shows distribution data for the compound of Example 1 from Example 14.

The following definitions are used, unless otherwise described: halo or halogen is fluoro, chloro, bromo, or iodo. Alkyl, alkoxy, etc. denote both straight and branched groups, but reference to an individual radical such as propyl embraces only the straight chain radical, a branched chain isomer such as isopropyl being specifically referred to.

The term "alkyl", by itself or as part of another substituent, means, unless otherwise stated, a straight or branched chain hydrocarbon radical, having the number of carbon atoms designated (i.e., $C_1$-$C_8$ means one to eight carbons). Examples include ($C_1$-$C_6$)alkyl, ($C_1$-$C_3$)alkyl, ($C_2$-$C_6$)alkyl and ($C_3$-$C_6$)alkyl. Examples of alkyl groups include methyl, ethyl, n-propyl, iso-propyl, n-butyl, t-butyl, iso-butyl, sec-butyl, n-pentyl, n-hexyl, n-heptyl, n-octyl, and higher homologs and isomers.

The term "alkoxy" refers to an alkyl group attached to the remainder of the molecule via an oxygen atom ("oxy").

The term "alkanoyl" refers to an alkyl group attached to the remainder of the molecule via a carbonyl C(=O)— group.

The term "cycloalkyl" refers to a saturated or partially unsaturated (non-aromatic) all carbon ring having 3 to 8 carbon atoms (i.e., ($C_3$-$C_8$)carbocycle). The term also includes multiple condensed, saturated all carbon ring systems (e.g., ring systems comprising 2, 3 or 4 carbocyclic rings). Accordingly, carbocycle includes multicyclic carbocycles such as a bicyclic carbocycles (e.g., bicyclic carbocycles having about 3 to 15 carbon atoms, about 6 to 15 carbon atoms, or 6 to 12 carbon atoms such as bicyclo[3.1.0]hexane and bicyclo[2.1.1]hexane), and polycyclic carbocycles (e.g tricyclic and tetracyclic carbocycles with up to about 20 carbon atoms). The rings of the multiple condensed ring system can be connected to each other via fused, spiro and bridged bonds when allowed by valency requirements. For example, multicyclic carbocycles can be connected to each other via a single carbon atom to form a spiro connection (e.g., spiropentane, spiro[4,5]decane, etc), via two adjacent carbon atoms to form a fused connection (e.g., carbocycles such as decahydronaphthalene, norsabinane, norcarane) or via two non-adjacent carbon atoms to form a bridged connection (e.g., norbornane, bicyclo[2.2.2]octane, etc). Non-limiting examples of cycloalkyls include cyclopropyl, cyclobutyl, cyclopentyl, cyclohexyl, bicyclo[2.2.1]heptane, pinane, and adamantane.

The term "aryl" as used herein refers to a single all carbon aromatic ring or a multiple condensed all carbon ring system wherein at least one of the rings is aromatic. For example, in certain embodiments, an aryl group has 6 to 20 carbon atoms, 6 to 14 carbon atoms, 6 to 12 carbon atoms, or 6 to 10 carbon atoms. Aryl includes a phenyl radical. Aryl also includes multiple condensed carbon ring systems (e.g., ring systems comprising 2, 3 or 4 rings) having about 9 to 20 carbon atoms in which at least one ring is aromatic and wherein the other rings may be aromatic or not aromatic (i.e., cycloalkyl). The rings of the multiple condensed ring system can be connected to each other via fused, spiro and bridged bonds when allowed by valency requirements. It is to be understood that the point of attachment of a multiple condensed ring system, as defined above, can be at any position of the ring system including an aromatic or a carbocycle portion of the ring. Non-limiting examples of aryl groups include, but are not limited to, phenyl, indenyl, indanyl, naphthyl, 1, 2, 3, 4-tetrahydronaphthyl, anthracenyl, and the like.

The term "heterocycle" refers to a single saturated or partially unsaturated ring that has at least one atom other than carbon in the ring, wherein the atom is selected from the group consisting of oxygen, nitrogen and sulfur; the term also includes multiple condensed ring systems that have at least one such saturated or partially unsaturated ring, which multiple condensed ring systems are further described below. Thus, the term includes single saturated or partially unsaturated rings (e.g., 3, 4, 5, 6 or 7-membered rings) from about 1 to 6 carbon atoms and from about 1 to 3 heteroatoms selected from the group consisting of oxygen, nitrogen and sulfur in the ring. The sulfur and nitrogen atoms may also be present in their oxidized forms. Exemplary heterocycles include but are not limited to azetidinyl, tetrahydrofuranyl and piperidinyl. The term "heterocycle" also includes multiple condensed ring systems (e.g., ring systems comprising 2, 3 or 4 rings) wherein a single heterocycle ring (as defined above) can be condensed with one or more groups selected from cycloalkyl, aryl, and heterocycle to form the multiple condensed ring system. The rings of the multiple condensed ring system can be connected to each other via fused, spiro and bridged bonds when allowed by valency requirements. It is to be understood that the individual rings of the multiple condensed ring system may be connected in any order relative to one another. It is also to be understood that the point of attachment of a multiple condensed ring system (as defined above for a heterocycle) can be at any position of the multiple condensed ring system including a heterocycle, aryl and carbocycle portion of the ring. In one embodiment the term heterocycle includes a 3-15 membered heterocycle. In one embodiment the term heterocycle includes a 3-10 membered heterocycle. In one embodiment the term heterocycle includes a 3-8 membered heterocycle. In one embodiment the term heterocycle includes a 3-7 membered heterocycle. In one embodiment the term heterocycle includes a 3-6 membered heterocycle. In one embodiment the term heterocycle includes a 4-6 membered heterocycle. In one embodiment the term heterocycle includes a 3-10 membered monocyclic or bicyclic heterocycle comprising 1 to 4 heteroatoms. In one embodiment the term heterocycle includes a 3-8 membered monocyclic or bicyclic heterocycle comprising 1 to 3 heteroatoms. In one embodiment the term heterocycle includes a 3-6 membered monocyclic heterocycle comprising 1 to 2 heteroatoms. In one embodiment the term heterocycle includes a 4-6 membered monocyclic heterocycle comprising 1 to 2 heteroatoms. Exemplary heterocycles include, but are not limited to aziridinyl, azetidinyl, pyrrolidinyl, piperidinyl, homopiperidinyl, morpholinyl, thiomorpholinyl, piperazinyl, tetrahydrofuranyl, dihydrooxazolyl, tetrahydropyranyl, tetrahydrothiopyranyl, 1,2,3,4-tetrahydroquinolyl, benzoxazinyl, dihydrooxazolyl, chromanyl, 1,2-dihydropyridinyl, 2,3-dihydrobenzofuranyl, 1,3-benzodioxolyl, 1,4-benzodioxanyl, spiro[cyclopropane-1,1'-isoindolinyl]-3'-one, isoindolinyl-1-one, 2-oxa-6-azaspiro[3.3]heptanyl, imidazolidin-2-one imidazolidine, pyrazolidine, butyrolactam, valerolactam, imidazolidinone, hydantoin, dioxolane, phthalimide, and 1,4-dioxane.

The term "heteroaryl" as used herein refers to a single aromatic ring that has at least one atom other than carbon in the ring, wherein the atom is selected from the group consisting of oxygen, nitrogen and sulfur; "heteroaryl" also includes multiple condensed ring systems that have at least one such aromatic ring, which multiple condensed ring systems are further described below. Thus, "heteroaryl" includes single aromatic rings of from about 1 to 6 carbon atoms and about 1-4 heteroatoms selected from the group consisting of oxygen, nitrogen and sulfur. The sulfur and nitrogen atoms may also be present in an oxidized form provided the ring is aromatic. Exemplary heteroaryl ring systems include but are not limited to pyridyl, pyrimidinyl, oxazolyl or furyl. "Heteroaryl" also includes multiple condensed ring systems (e.g., ring systems comprising 2, 3 or 4 rings) wherein a heteroaryl group, as defined above, is condensed with one or more rings selected from cycloalkyl, aryl, heterocycle, and heteroaryl. It is to be understood that the point of attachment for a heteroaryl or heteroaryl multiple condensed ring system can be at any suitable atom of the heteroaryl or heteroaryl multiple condensed ring system including a carbon atom and a heteroatom (e.g., a nitrogen). Exemplary heteroaryls include but are not limited to pyridyl, pyrrolyl, pyrazinyl, pyrimidinyl, pyridazinyl, pyrazolyl, thienyl, indolyl, imidazolyl, triazolyl, tetrazolyl, oxazolyl, isoxazolyl, thiazolyl, furyl, oxadiazolyl, thiadiazolyl, quinolyl, isoquinolyl, benzothiazolyl, benzoxazolyl, indazolyl, quinoxalyl, and quinazolyl.

The term "alkoxycarbonyl" as used herein refers to a group (alkyl)-O—C(=O)—, wherein the term alkyl has the meaning defined herein.

The term "alkanoyloxy" as used herein refers to a group (alkyl)-C(=O)—O—, wherein the term alkyl has the meaning defined herein.

As used herein, the term "heteroatom" is meant to include oxygen (O), nitrogen (N), sulfur (S) and silicon (Si).

As used herein, the term "protecting group" refers to a substituent that is commonly employed to block or protect a particular functional group on a compound. For example, an "amino-protecting group" is a substituent attached to an amino group that blocks or protects the amino functionality in the compound. Suitable amino-protecting groups include acetyl, trifluoroacetyl, t-butoxycarbonyl (BOC), benzyloxycarbonyl (CBZ) and 9-fluorenylmethylenoxycarbonyl (Fmoc). Similarly, a "hydroxy-protecting group" refers to a substituent of a hydroxy group that blocks or protects the hydroxy functionality. Suitable protecting groups include acetyl and silyl. A "carboxy-protecting group" refers to a substituent of the carboxy group that blocks or protects the carboxy functionality. Common carboxy-protecting groups include phenylsulfonylethyl, cyanoethyl, 2-(trimethylsilyl)ethyl, 2-(trimethylsilyl)ethoxymethyl, 2-(p-toluenesulfonyl)ethyl, 2-(p-nitrophenylsulfenyl)ethyl, 2-(diphenylphosphino)-ethyl, nitroethyl and the like. For a general description of protecting groups and their use, see P. G. M. Wuts and T. W. Greene, Greene's Protective Groups in Organic Synthesis 4$^{th}$ edition, Wiley-Interscience, New York, 2006.

As used herein a wavy line "⁓" that intersects a bond in a chemical structure indicates the point of attachment of the bond that the wavy bond intersects in the chemical structure to the remainder of a molecule.

The terms "treat", "treatment", or "treating" to the extent it relates to a disease or condition includes inhibiting the disease or condition, eliminating the disease or condition, and/or relieving one or more symptoms of the disease or condition. The terms "treat", "treatment", or "treating" also refer to both therapeutic treatment and/or prophylactic treatment or preventative measures, wherein the object is to prevent or slow down (lessen) an undesired physiological change or disorder. For example, beneficial or desired clinical results include, but are not limited to, alleviation of symptoms, diminishment of extent of disease or disorder, stabilized (i.e., not worsening) state of disease or disorder, delay or slowing of disease progression, amelioration or palliation of the disease state or disorder, and remission (whether partial or total), whether detectable or undetectable. "Treat", "treatment", or "treating," can also mean prolonging survival as compared to expected survival if not receiving treatment. Those in need of treatment include those already with the disease or disorder as well as those prone to have the disease or disorder or those in which the disease or disorder is to be prevented. In one embodiment "treat", "treatment", or "treating" does not include preventing or prevention, The phrase "therapeutically effective amount" or "effective amount" includes but is not limited to an amount of a compound of the that (i) treats or prevents the particular disease, condition, or disorder, (ii) attenuates, ameliorates, or eliminates one or more symptoms of the particular disease, condition, or disorder, or (iii) prevents or delays the onset of one or more symptoms of the particular disease, condition, or disorder described herein.

The term "subject" as used herein refers to any individual or patient to which the subject methods are performed. Generally, the subject is a mammal, specifically human, although as will be appreciated by those in the art, the subject may be an animal. Thus other animals, including vertebrate such as rodents (including mice, rats, hamsters and guinea pigs), cats, dogs, rabbits, farm animals including cows, horses, goats, sheep, pigs, chickens, etc., and primates (including monkeys, chimpanzees, orangutans and gorillas) are included within the definition of subject. In one embodiment the subject is a mammalian subject. In one embodiment, the subject is a human subject.

The term "mammal" as used herein refers to humans, higher non-human primates, rodents, domestic, cows, horses, pigs, sheep, dogs and cats. In one embodiment, the mammal is a human.

The term "selective antagonist of RAR alpha" refers to a compound that has at least 2, 5, or 10 fold greater antagonist activity at RAR alpha compared to its activity at either RAR beta or RAR gamma. In one embodiment, the term "selective agonist of RAR alpha" refers to a compound that has at least 2, 5, or 10 fold greater antagonist activity at RAR alpha compared to its activity at both RAR beta and RAR gamma.

The compounds disclosed herein can also exist as tautomeric isomers in certain cases. Although only one delocalized resonance structure may be depicted, all such forms are contemplated within the scope of the invention.

It is understood by one skilled in the art that this invention also includes any compound claimed that may be enriched at any or all atoms above naturally occurring isotopic ratios with one or more isotopes such as, but not limited to, deuterium ($^2$H or D). As a non-limiting example, a —CH$_3$ group may be substituted with —CD$_3$.

Stereochemical definitions and conventions used herein generally follow S. P. Parker, Ed., McGraw-Hill Dictionary of Chemical Terms (1984) McGraw-Hill Book Company, New York; and Eliel, E. and Wilen, S., "Stereochemistry of Organic Compounds", John Wiley & Sons, Inc., New York, 1994. The compounds of the invention can contain asymmetric or chiral centers, and therefore exist in different stereoisomeric forms. It is intended that all stereoisomeric forms of the compounds of the invention, including but not limited to, diastereomers, enantiomers and atropisomers, as well as mixtures thereof such as racemic mixtures, form part of the present invention. Many organic compounds exist in optically active forms, i.e., they have the ability to rotate the plane of plane-polarized light. In describing an optically active compound, the prefixes D and L, or R and S, are used to denote the absolute configuration of the molecule about its chiral center(s). The prefixes d and l or (+) and (−) are employed to designate the sign of rotation of plane-polarized light by the compound, with (−) or l meaning that the compound is levorotatory. A compound prefixed with (+) or d is dextrorotatory. For a given chemical structure, these stereoisomers are identical except that they are mirror images of one another. A specific stereoisomer can also be referred to as an enantiomer, and a mixture of such isomers is often called an enantiomeric mixture. A 50:50 mixture of enantiomers is referred to as a racemic mixture or a racemate, which can occur where there has been no stereoselection or stereospecificity in a chemical reaction or process. The terms "racemic mixture" and "racemate" refer to an equimolar mixture of two enantiomeric species, devoid of optical activity.

It will be appreciated by those skilled in the art that compounds of the invention having a chiral center may exist in and be isolated in optically active and racemic forms. Some compounds may exhibit polymorphism. It is to be understood that the present invention encompasses any racemic, optically-active, polymorphic, or stereoisomeric form, or mixtures thereof, of a compound of the invention, which possess the useful properties described herein, it being well known in the art how to prepare optically active forms (for example, by resolution of the racemic form by recrystallization techniques, by synthesis from optically-active starting materials, by chiral synthesis, or by chromatographic separation using a chiral stationary phase.

When a bond in a compound formula herein is drawn in a non-stereochemical manner (e.g. flat), the atom to which the bond is attached includes all stereochemical possibilities. When a bond in a compound formula herein is drawn in a defined stereochemical manner (e.g. bold, bold-wedge, dashed or dashed-wedge), it is to be understood that the atom to which the stereochemical bond is attached is enriched in the absolute stereoisomer depicted unless otherwise noted. In one embodiment, the compound may be at least 51% the absolute stereoisomer depicted. In another embodiment, the compound may be at least 60% the absolute stereoisomer depicted. In another embodiment, the compound may be at least 80% the absolute stereoisomer depicted. In another embodiment, the compound may be at least 90% the absolute stereoisomer depicted. In another embodiment, the compound may be at least 95 the absolute stereoisomer depicted. In another embodiment, the compound may be at least 99% the absolute stereoisomer depicted.

Specific values listed below for radicals, substituents, and ranges, are for illustration only; they do not exclude other defined values or other values within defined ranges for the radicals and substituents. It is to be understood that two or more values may be combined. It is also to be understood that the values listed herein below (or subsets thereof) can be excluded.

Specifically, $(C_1-C_6)$alkyl can be methyl, ethyl, propyl, isopropyl, butyl, iso-butyl, sec-butyl, pentyl, 3-pentyl, or hexyl; $(C_1-C_6)$alkoxy can be methoxy, ethoxy, propoxy, isopropoxy, butoxy, iso-butoxy, sec-butoxy, pentoxy, 3-pentoxy, or hexyloxy; $(C_1-C_6)$alkanoyl can be acetyl, propanoyl or butanoyl; aryl can be phenyl, indenyl, or naphthyl; and heteroaryl can be furyl, imidazolyl, triazolyl, triazinyl, oxazoyl, isoxazoyl, thiazolyl, isothiazoyl, pyrazolyl, pyrrolyl, pyrazinyl, tetrazolyl, pyridyl, (or its N-oxide), thienyl, pyrimidinyl (or its N-oxide), indolyl, isoquinolyl (or its N-oxide) or quinolyl (or its N-oxide).

A specific value for $R^1$ is $C_1-C_3$ alkyl.
A specific value for $R^1$ is methyl.
A specific value for $R^2$ is $C_1-C_3$ alkyl.
A specific value for $R^2$ is methyl.
A specific value for $R^3$ is $C_6-C_{10}$ aryl that is optionally substituted with one or more (e.g., 1, 2, 3, or 4) groups independently selected from halo, cyano, nitro, carboxy, $C_1-C_6$ alkyl, $C_1-C_6$ alkoxy, $C_1-C_6$ alkanoyl, $C_1-C_6$ alkanoyloxy, $C_1-C_6$ alkoxycarbonyl, —$NR^aR^b$, and —$C(=O)NR^cR^d$, wherein any $C_1-C_6$ alkyl, $C_1-C_6$ alkoxy, $C_1-C_6$ alkanoyl, $C_1-C_6$ alkanoyloxy, and $C_1-C_6$ alkoxycarbonyl is optionally substituted with one or more groups independently selected from halo.

A specific value for $R^3$ is phenyl that is optionally substituted with one or more (e.g., 1, 2, 3, or 4) groups independently selected from halo, cyano, nitro, carboxy, $C_1-C_6$ alkyl, $C_1-C_6$ alkoxy, $C_1-C_6$ alkanoyl, $C_1-C_6$ alkanoyloxy, $C_1-C_6$ alkoxycarbonyl, —$NR^aR^b$, and —$C(=O)NR^cR^d$, wherein any $C_1-C_6$ alkyl, $C_1-C_6$ alkoxy, $C_1-C_6$ alkanoyl, $C_1-C_6$ alkanoyloxy, and $C_1-C_6$ alkoxycarbonyl is optionally substituted with one or more groups independently selected from halo.

A specific value for $R^3$ is $C_6-C_{10}$ aryl that is optionally substituted with one or more (e.g., 1, 2, 3, or 4) groups independently selected from $C_1-C_6$ alkyl that is optionally substituted with one or more groups independently selected from halo.

A specific value for $R^3$ is phenyl that is optionally substituted with one or more (e.g., 1, 2, 3, or 4) groups independently selected from $C_1-C_6$ alkyl that is optionally substituted with one or more groups independently selected from halo.

A specific value for $R^3$ is $C_6-C_{10}$ aryl that is substituted with $C_1-C_6$ alkyl.

A specific value for $R^3$ is phenyl that is substituted with $C_1-C_6$ alkyl.

A specific value for $R^3$ is 4-methylphenyl.

A specific value for $R^4$ is $C_6-C_{10}$ aryl, 5-10 membered heteroaryl, $C_6-C_{10}$ aryl$C_1-C_3$ alkyl, or 5-10 membered heteroaryl$C_1-C_3$ alkyl, wherein any $C_6-C_{10}$ aryl, 5-10 membered heteroaryl, $C_6-C_{10}$ aryl$C_1-C_3$ alkyl, and 5-10 membered heteroaryl$C_1-C_3$ alkyl is substituted with carboxy and is further optionally substituted with one or more groups independently selected from halo, cyano, nitro, carboxy, $C_1-C_6$ alkyl, $C_1-C_6$ alkoxy, $C_1-C_6$ alkanoyl, $C_1-C_6$ alkanoyloxy, $C_1-C_6$ alkoxycarbonyl, —$NR^eR^f$, or —$C(=O)NR^gR^h$, wherein any $C_1-C_6$ alkyl, $C_1-C_6$ alkoxy, $C_1-C_6$ alkanoyl, $C_1-C_6$ alkanoyloxy, and $C_1-C_6$ alkoxycarbonyl is optionally substituted with one or more groups independently selected from halo;

A specific value for $R^4$ is $C_6-C_{10}$ aryl that is substituted with carboxy and that is further optionally substituted with one or more (e.g., 1, 2, 3, or 4) groups independently selected from halo, cyano, nitro, carboxy, $C_1-C_6$ alkyl, $C_1-C_6$ alkoxy, $C_1-C_6$ alkanoyl, $C_1-C_6$ alkanoyloxy, $C_1-C_6$ alkoxycarbonyl, —$NR^aR^b$, and —$C(=O)NR^cR^d$, wherein any $C_1-C_6$ alkyl, $C_1-C_6$ alkoxy, $C_1-C_6$ alkanoyl, $C_1-C_6$ alkanoyloxy, and $C_1-C_6$ alkoxycarbonyl is optionally substituted with one or more groups independently selected from halo.

A specific value for $R^4$ is phenyl that is substituted with carboxy and that is further optionally substituted with one or more (e.g., 1, 2, 3, or 4) groups independently selected from halo, cyano, nitro, carboxy, $C_1-C_6$ alkyl, $C_1-C_6$ alkoxy, $C_1-C_6$ alkanoyl, $C_1-C_6$ alkanoyloxy, $C_1-C_6$ alkoxycarbonyl, —$NR^aR^b$, and —$C(=O)NR^cR^d$, wherein any $C_1-C_6$ alkyl, $C_1-C_6$ alkoxy, $C_1-C_6$ alkanoyl, $C_1-C_6$ alkanoyloxy, and $C_1-C_6$ alkoxycarbonyl is optionally substituted with one or more groups independently selected from halo.

A specific value for $R^4$ is $C_6-C_{10}$ aryl that is substituted with carboxy and that is further optionally substituted with one or more (e.g., 1, 2, 3, or 4) groups independently selected from $C_1-C_6$ alkyl that is optionally substituted with one or more groups independently selected from halo.

A specific value for $R^4$ is phenyl that is substituted with carboxy and that is further optionally substituted with one or more (e.g., 1, 2, 3, or 4) groups independently selected from $C_1$-$C_6$ alkyl that is optionally substituted with one or more groups independently selected from halo.

A specific value for $R^4$ is $C_6$-$C_{10}$ aryl that is substituted with carboxy.

A specific value for $R^4$ is phenyl that is substituted with carboxy.

A specific value for $R^4$ is 4-carboxyphenyl.

A specific value for $R^5$ is H.

A specific value for $R^6$ is H.

A specific compound or salt is a compound of formula (Ia):

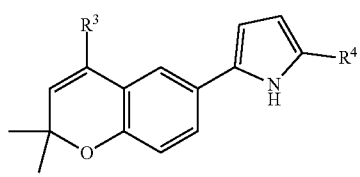

(Ia)

or a pharmaceutically acceptable salt, stereoisomer, solvate, or prodrug thereof.

A specific compound or salt is a compound of formula (Ib):

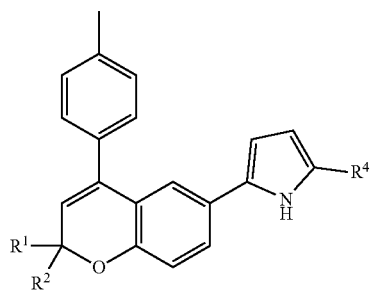

(Ib)

or a pharmaceutically acceptable salt, stereoisomer, solvate, or prodrug thereof.

A specific compound or salt is a compound of formula (Ic):

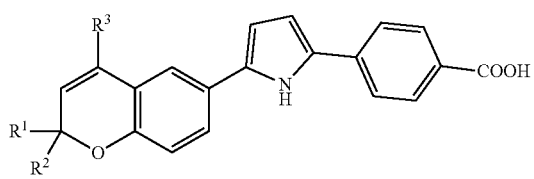

(Ic)

or a pharmaceutically acceptable salt, stereoisomer, solvate, or prodrug thereof.

A specific compound or salt is a compound of formula (Id):

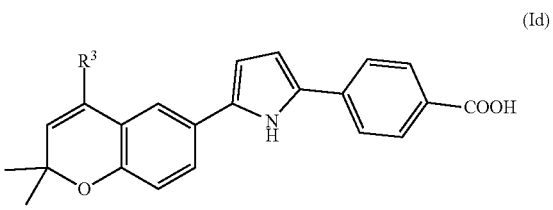

(Id)

or a pharmaceutically acceptable salt, stereoisomer, solvate, or prodrug thereof.

A specific compound or salt is:

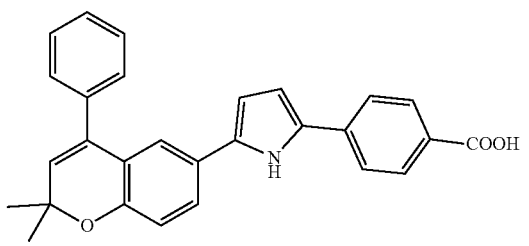

or

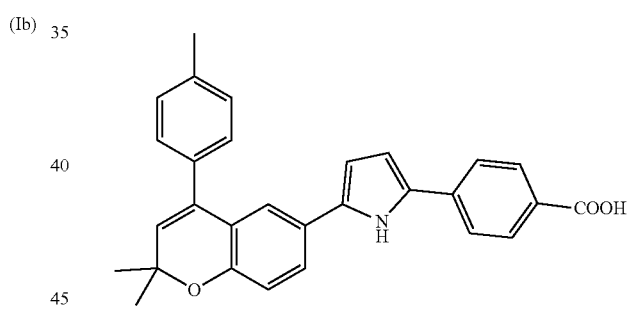

or a pharmaceutically acceptable salt thereof.

A specific compound or salt is:

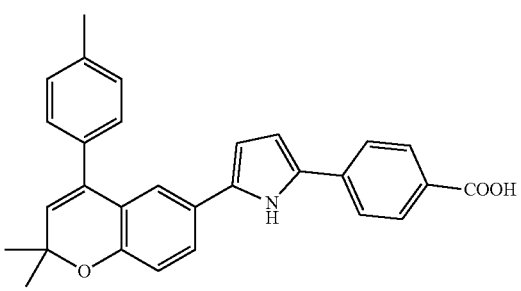

or a pharmaceutically acceptable salt thereof.

A specific compound, pharmaceutically acceptable salt, stereoisomer, solvate, or prodrug is selected from the group consisting of:

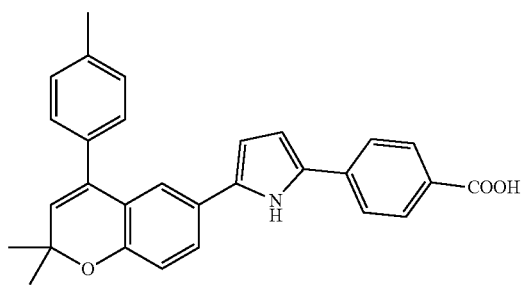 [SMILES: Cc1ccc(C2=CC(C)(C)Oc3ccc(-c4ccc(-c5ccc(C(=O)O)cc5)[nH]4)cc32)cc1]
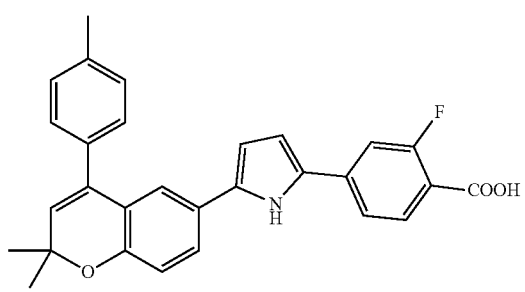
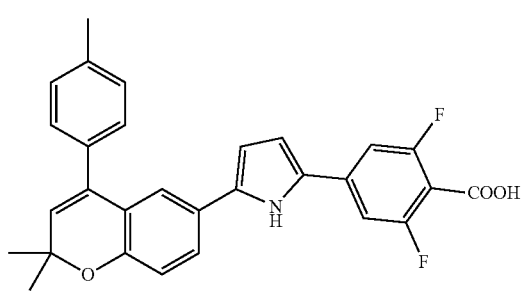
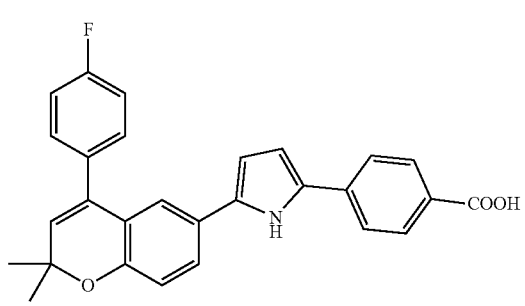
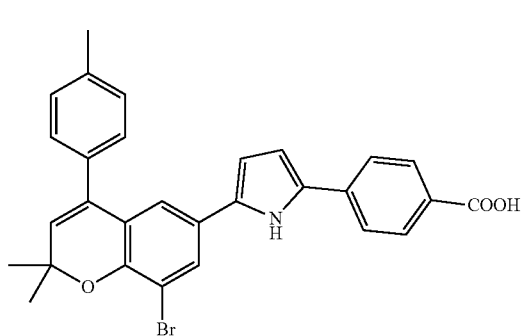
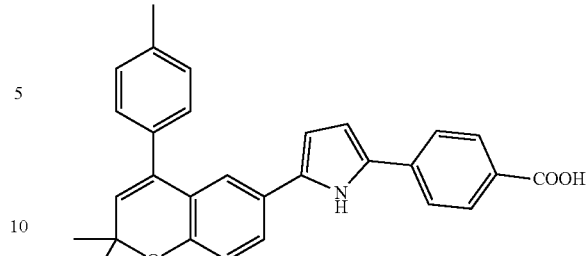
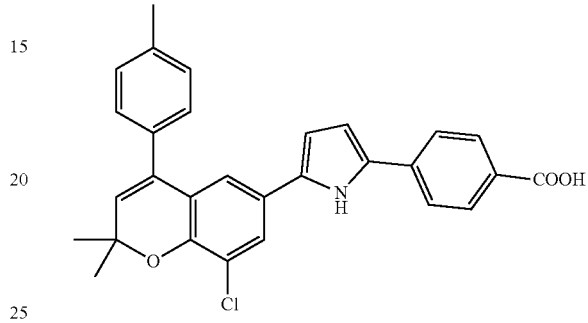
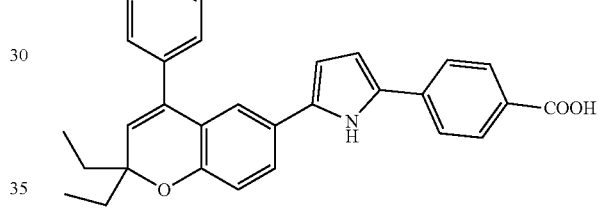
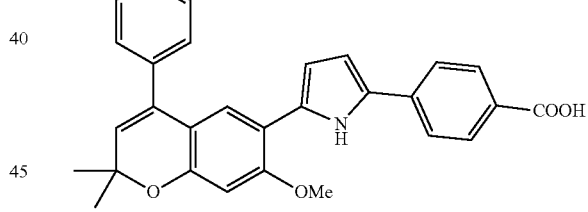
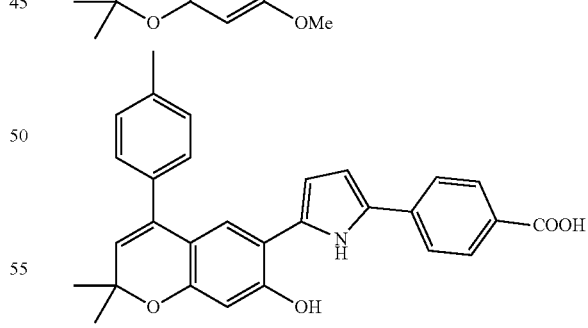
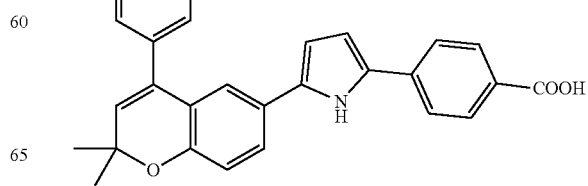

-continued

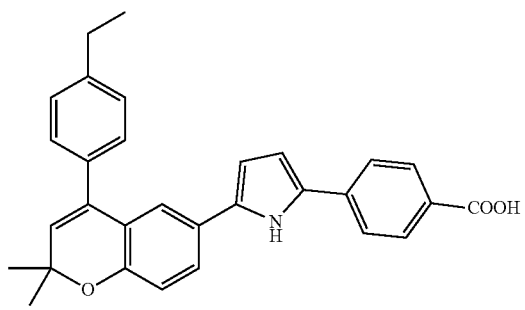
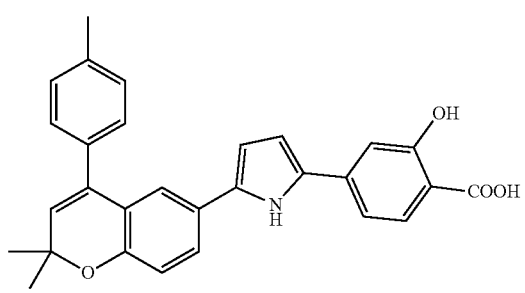
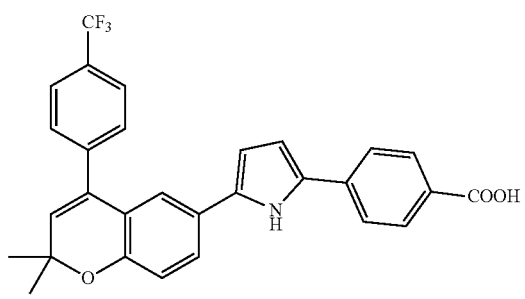
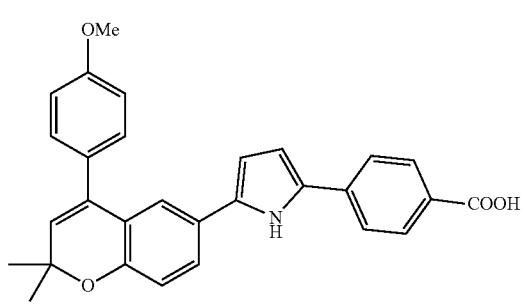
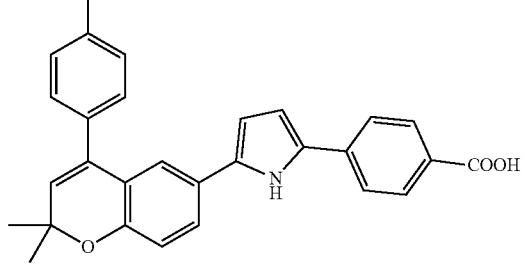

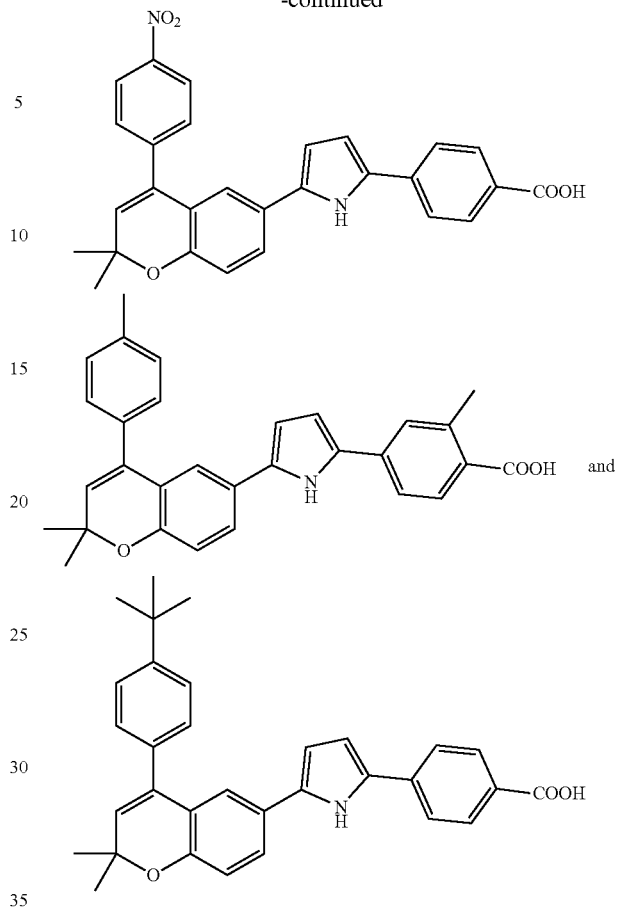

and pharmaceutically acceptable salts, stereoisomers, solvates, and prodrugs thereof.

Processes for preparing compounds of formula I are provided as further embodiments of the invention and are illustrated by the following procedures in which the meanings of the generic radicals are as given above unless otherwise qualified.

In cases where compounds are sufficiently basic or acidic, a salt of a compound of formula I can be useful as an intermediate for isolating or purifying a compound of formula I. Additionally, administration of a compound of formula I as a pharmaceutically acceptable acid or base salt may be appropriate. Examples of pharmaceutically acceptable salts are organic acid addition salts formed with acids which form a physiological acceptable anion, for example, tosylate, methanesulfonate, acetate, citrate, malonate, tartarate, succinate, benzoate, ascorbate, α-ketoglutarate, and α-glycerophosphate. Suitable inorganic salts may also be formed, including hydrochloride, sulfate, nitrate, bicarbonate, and carbonate salts.

Salts may be obtained using standard procedures well known in the art, for example by reacting a sufficiently basic compound such as an amine with a suitable acid affording a physiologically acceptable anion. Alkali metal (for example, sodium, potassium or lithium) or alkaline earth metal (for example calcium) salts of carboxylic acids can also be made.

The compounds of formula (I) can be formulated as pharmaceutical compositions and administered to a mammalian host, such as a human subject, in a variety of forms adapted to the chosen route of administration, i.e., orally or parenterally, by intravenous, intramuscular, topical or subcutaneous routes. The pharmaceutical compositions of the invention can comprise one or more excipients. When used in combination with the pharmaceutical compositions of the invention the term "excipients" refers generally to an additional ingredient that is combined with the compound of formula (I) or the pharmaceutically acceptable salt thereof to provide a corresponding composition. For example, when used in combination with the pharmaceutical compositions of the invention the term "excipients" includes, but is not limited to: carriers, binders, disintegrating agents, lubricants, sweetening agents, flavoring agents, coatings, preservatives, and dyes.

As used herein, "pharmaceutical composition" refers to a formulation comprising an active ingredient, and optionally a pharmaceutically acceptable carrier, diluent or excipient. The term "active ingredient" can interchangeably refer to an "effective ingredient" and is meant to refer to any agent that is capable of inducing a sought-after effect upon administration. Examples of active ingredient include, but are not limited to, chemical compound, drug, therapeutic agent, small molecule, etc.

The pharmaceutical compositions of the invention can comprise one or more excipients. When used in combination with the pharmaceutical compositions of the invention the term "excipients" refers generally to an additional ingredient that is combined with the compound of formula (I) or the pharmaceutically acceptable salt thereof to provide a corresponding composition. For example, when used in combination with the pharmaceutical compositions of the invention the term "excipients" includes, but is not limited to: carriers, binders, disintegrating agents, lubricants, sweetening agents, flavoring agents, coatings, preservatives, and dyes.

By "pharmaceutically acceptable" it is meant the carrier, diluent or excipient must be compatible with the other ingredients of the formulation and not deleterious to the recipient thereof, nor to the activity of the active ingredient of the formulation. Pharmaceutically acceptable carriers, excipients or stabilizers are well known in the art, for example Remington's Pharmaceutical Sciences, 16th edition, Osol, A. Ed. (1980). Pharmaceutically acceptable carriers, excipients, or stabilizers are nontoxic to recipients at the dosages and concentrations employed, and may include buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (for example, Zn-protein complexes); and/or non-ionic surfactants such as TWEEN™, PLURONICS™ or polyethylene glycol (PEG). Examples of carrier include, but are not limited to, liposome, nanoparticles, ointment, micelles, microsphere, microparticle, cream, emulsion, and gel. Examples of excipient include, but are not limited to, anti-adherents such as magnesium stearate, binders such as saccharides and their derivatives (sucrose, lactose, starches, cellulose, sugar alcohols and the like) protein like gelatin and synthetic polymers, lubricants such as talc and silica, and preservatives such as antioxidants, vitamin A, vitamin E, vitamin C, retinyl palmitate, selenium, cysteine, methionine, citric acid, sodium sulfate and parabens. Examples of diluent include, but are not limited to, water, alcohol, saline solution, glycol, mineral oil and dimethyl sulfoxide (DMSO).

Thus, the present compounds may be systemically administered, e.g., orally, in combination with a pharmaceutically acceptable vehicle or excipient such as an inert diluent or an assimilable edible carrier. They may be enclosed in hard or soft shell gelatin capsules, may be compressed into tablets, or may be incorporated directly with the food of the subject's diet. For oral therapeutic administration, the active compound may be combined with one or more pharmaceutically acceptable excipients and used in the form of ingestible tablets, buccal tablets, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 60% of the weight of a given unit dosage form. The amount of active compound in such therapeutically useful compositions is such that an effective dosage level will be obtained.

The tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the active compound may be incorporated into sustained-release preparations and devices.

The active compound may also be administered intravenously or intraperitoneally by infusion or injection. Solutions of the active compound or its salts can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

The pharmaceutical dosage forms suitable for injection or infusion can include sterile aqueous solutions or dispersions or sterile powders comprising the active ingredient which are adapted for the extemporaneous preparation of sterile injectable or infusible solutions or dispersions, optionally encapsulated in liposomes. In all cases, the ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions are prepared by incorporating the active compound in the required amount in the appropriate solvent with various of the other ingredients enumerated above, as required, followed by filter sterilization. In the case of sterile powders for the preparation of sterile injectable solutions, the preferred methods of preparation are vacuum drying and the freeze-drying techniques, which yield a powder of the active ingredient plus any additional desired ingredient present in the previously sterile-filtered solutions.

For topical administration, the present compounds may be applied in pure form, i.e., when they are liquids. However, it will generally be desirable to administer them to the skin as compositions or formulations, in combination with a dermatologically acceptable carrier, which may be a solid or a liquid.

Useful solid carriers include finely divided solids such as talc, clay, microcrystalline cellulose, silica, alumina and the like. Useful liquid carriers include water, alcohols or glycols or water-alcohol/glycol blends, in which the present compounds can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers.

Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user.

Examples of useful dermatological compositions which can be used to deliver the compounds of formula (I) to the skin are known to the art; for example, see Jacquet et al. (U.S. Pat. No. 4,608,392), Geria (U.S. Pat. No. 4,992,478), Smith et al. (U.S. Pat. No. 4,559,157) and Wortzman (U.S. Pat. No. 4,820,508).

Useful dosages of the compounds of formula (I) can be determined by comparing their in vitro activity, and in vivo activity in animal models. Methods for the extrapolation of effective dosages in mice, and other animals, to humans are known to the art; for example, see U.S. Pat. No. 4,938,949.

The amount of the compound, or an active salt or derivative thereof, required for use in treatment will vary not only with the particular salt selected but also with the route of administration, the nature of the condition being treated and the age and condition of the subject or patient and will be ultimately at the discretion of the attendant physician or clinician.

The dose of a compound of formula (I) to be administered to a subject can optionally range from about 0.0001 mg/kg to about 100 mg/kg, about 0.01 mg/kg to about 5 mg/kg, about 0.15 mg/kg to about 3 mg/kg, 0.5 mg/kg to about 2 mg/kg and about 1 mg/kg to about 2 mg/kg of the subject's body weight. In other aspects, the dose ranges from about 100 mg/kg to about 5 g/kg, about 500 mg/kg to about 2 mg/kg and about 750 mg/kg to about 1.5 g/kg of the subject's body weight. For example, depending on the type and severity of the disease, about 1 μg/kg to 15 mg/kg (e.g., 0.1-20 mg/kg) of compound is a candidate dosage for administration to the subject, whether, for example, by one or more separate administrations, or by continuous infusion. A typical daily dosage is in the range from about 1 μg/kg to 100 mg/kg or more, depending on the factors mentioned above. For repeated administrations over several days or longer, depending on the condition, the treatment is sustained until a desired suppression of disease symptoms occurs. However, other dosage regimens may be useful. Unit doses can be in the range, for instance of about 5 mg to 500 mg, such as 50 mg, 100 mg, 150 mg, 200 mg, 250 mg and 300 mg. Specific dosages include 0.1 mg, 0.5 mg, 1, mg, 1.5 mg, 2 mg, 2.5 mg, 3 mg, 3.5 mg, 4 mg, 4.5 mg, 5 mg, 5.5 mg, 6 mg, 6.5 mg, 7.0 mg, 7.5 mg, 8 mg, 8.5 mg, 9 mg, 9.5 mg, 10 mg, 11 mg, 12 mg, 13, mg 14 mg, 15 mg, 16 mg, 7 mg, 18 mg, 19 mg, 20 mg, 25 mg, 30 mg, 35 mg, 40 mg, 45 mg and 50 mg. The progress of therapy is monitored by conventional techniques and assays.

In some aspects, a compound of formula (I) can be administered to a human subject at an effective amount (or dose) of less than about 1 μg/kg, for instance, about 0.35 to about 0.75 μg/kg or about 0.40 to about 0.60 μg/kg. In some aspects, the dose of the compound is about 0.35 μg/kg, or about 0.40 μg/kg, or about 0.45 μg/kg, or about 0.50 μg/kg, or about 0.55 μg/kg, or about 0.60 μg/kg, or about 0.65 μg/kg, or about 0.70 μg/kg, or about 0.75 μg/kg, or about 0.80 μg/kg, or about 0.85 μg/kg, or about 0.90 μg/kg, or about 0.95 μg/kg or about 1 μg/kg. In various aspects, the absolute dose of a compound is about 2 μg/subject to about 45 μg/subject, or about 5 to about 40, or about 10 to about 30, or about 15 to about 25 μg/subject. In some aspects, the absolute dose of a compound is about 20 μg, or about 30 μg, or about 40 μg.

In various aspects, the dose of a compound of formula (I) may be determined by the human subject's body weight. For example, an absolute dose of a compound of about 2 μg for a pediatric human subject of about 0 to about 5 kg (e.g. about 0, or about 1, or about 2, or about 3, or about 4, or about 5 kg); or about 3 μg for a pediatric human subject of about 6 to about 8 kg (e.g. about 6, or about 7, or about 8 kg), or about 5 μg for a pediatric human subject of about 9 to about 13 kg (e.g. 9, or about 10, or about 11, or about 12, or about 13 kg); or about 8 μg for a pediatric human subject of about 14 to about 20 kg (e.g. about 14, or about 16, or about 18, or about 20 kg), or about 12 μg for a pediatric human subject of about 21 to about 30 kg (e.g. about 21, or about 23, or about 25, or about 27, or about 30 kg), or about 13 μg for a pediatric human subject of about 31 to about 33 kg (e.g. about 31, or about 32, or about 33 kg), or about 20 μg for an adult human subject of about 34 to about 50 kg (e.g. about 34, or about 36, or about 38, or about 40, or about 42, or about 44, or about 46, or about 48, or about 50 kg), or about 30 μg for an adult human subject of about 51 to about 75 kg (e.g. about 51, or about 55, or about 60, or about 65, or about 70, or about 75 kg), or about 45 μg for an adult human subject of greater than about 114 kg (e.g. about 114, or about 120, or about 130, or about 140, or about 150 kg).

In one aspect, the compound formula (I) may be administered to a mammal (e.g., a human) at a dose of about 7.5 mg/kg.

The desired dose may conveniently be presented in a single dose or as divided doses administered at appropriate intervals, for example, as two, three, four or more sub-doses per day. The sub-dose itself may be further divided, e.g., into a number of discrete loosely spaced administrations; such as multiple inhalations from an insufflator or by application of a plurality of drops into the eye.

As used herein, the terms "fertility" or "fertile" refer to the ability to produce offspring.

As used herein, the terms "infertility" of "infertile" refer to a reduced ability or inability to produce offspring. The term "reversible infertility" as used herein relates to the induction of infertility in a subject which is then reversed so that the subject is fertile. The compounds disclosed herein produce reversible infertility in male subjects. While the compounds are administered the subjects become infertile and are unable to produce offspring. After cessation of administration of the disclosed compounds the subjects are no longer infertile and have the ability to produce offspring. In some embodiments, infertility is measured as less than 20 million sperm per milliliter, less than 19 million sperm per milliliter, less than 18 million sperm per milliliter, less than 17 million sperm per milliliter, less than 16 million sperm per milliliter, less than 15 million sperm per milliliter, less than 14 million sperm per milliliter, less than 13 million sperm per milliliter, less than 12 million sperm per milliliter, less than 11 million sperm per milliliter, less than 10 million sperm per milliliter, less than 9 million sperm per milliliter, less than 8 million sperm per milliliter, less than 7 million sperm per milliliter, less than 6 million sperm per milliliter, less than 5 million sperm per milliliter, less than 4 million sperm per milliliter, less than 3 million sperm per milliliter, less than 2 million sperm per milliliter, less than 1 million sperm per milliliter. In some embodiments, infertility is measured as motility less than 40%, 35%, 30%, 25%, 20%, 15%, 10%, 5% 0%. In some embodiments, infertility is measured as less than 12% normal morphologic sperm, less than 11% normal morphologic sperm, less than 10% normal morphologic sperm, less than 9% normal morphologic sperm, less than 8% normal morphologic sperm, less than 7% normal morphologic sperm, less than 6% normal morphologic sperm, less than 5% normal morphologic sperm, less than 4% normal morphologic sperm, less than 3% normal morphologic sperm, less than 2% normal morphologic sperm, or less than 1% normal morphologic sperm.

In one embodiment, infertility is achieved in less than 145 days, 140 days, 135 days, 130 days, 125 days, 120 days, 115 days, 110 days, 105 days, 100 days, 95 days, 90 days, 85 days, 80 days, 75 days, 70 days, 65 days, 60 days, 55 days, 50 days, 45 days, 40 days, 35 days, 30 days, 29 days, 28 days, 27 days, 26 days, 25 days, 24 days, 23 days, 22 days, 21 days, 20 days, 19 days, 18 days, 17 days, 16 days, 15 days, 14 days, 13 days, 12 days, 11 days, 10 days, 9 days, 8 days, 7 days, 6 days, 5 days, 4 days, 3 days, 2 days, or 1 days after treatment. In one embodiment, infertility is achieved in less than 20 weeks, 19 weeks, 18 weeks, 17 weeks, 16 weeks, 15 weeks, 14 weeks, 13 weeks, 12 weeks, 11 weeks, 10 weeks, 9 weeks, 8 weeks, 7 weeks, 6 weeks, 5 weeks, 4 weeks, 3 weeks, 2 weeks, or 1 weeks.

The term "contraceptive" as used here in refers a method, pharmaceutical agent or compound or device used to prevent pregnancy.

The term "disease or condition associated with RAR alpha activity" refers to any condition that can be improved by administering a RAR alpha specific antagonist. Examples of such diseases and conditions include cancer, metabolic disease, eye diseases, acne, neurodegenerative diseases and renal diseases.

The term "disease or condition associated with RAR alpha activity" also includes: aging, depression, hyperlipidemia, vascular trauma (e.g., lowering serum triglycerides), ischemic injury (e.g., in dermal tissue) and rheumatoid arthritis. Additionally, the compounds of the invention may also be useful for reducing mucin secretion, to reduce the side-effects of chemotherapy or radiation therapy, as an antidote for retinoid intoxication, to inhibit viral (e.g., HIV, human cytomegalovirus) replication, or to antagonize the inhibitive effect of ATRA and rescue BMP2-induced osteoblastogenesis.

The term "cancer" refers to a group of diseases characterized by abnormal and uncontrolled cell proliferation starting at one site (primary site) with the potential to invade and to spread to others sites (secondary sites, metastases) which differentiate cancer (malignant tumor) from benign tumor. Virtually all the organs can be affected, leading to more than 100 types of cancer that can affect humans. Cancers can result from many causes including genetic predisposition, viral infection, exposure to ionizing radiation, exposure environmental pollutant, tobacco and or alcohol use, obesity, poor diet, lack of physical activity or any combination thereof. As used herein, "neoplasm" or "tumor" including grammatical variations thereof, means new and abnormal growth of tissue, which may be benign or cancerous. In a related aspect, the neoplasm is indicative of a neoplastic disease or disorder, including but not limited, to various cancers. For example, such cancers can include prostate, pancreatic, biliary, colon, rectal, liver, kidney, lung, testicular, breast, ovarian, pancreatic, brain, and head and neck cancers, melanoma, sarcoma, multiple myeloma, leukemia, lymphoma, and the like.

Metabolic diseases are disorders that negatively alters the body's processing and distribution of macronutrients such as proteins, fats, and carbohydrates. Metabolic diseases include obesity and diabetes.

Neurodegenerative diseases are a heterogeneous group of disorders that are characterized by the progressive degeneration of the structure and function of the central nervous system or peripheral nervous system. Examples of neurodegenerative diseases include Alzheimer's disease and Parkinson's disease.

Renal diseases are diseases that cause damage to the kidney. Examples of renal diseases include glomerulosclerosis and polycystic kidney disease.

The invention will now be illustrated by the following non-limiting Examples.

EXAMPLES

General Scheme for Preparing Compounds of Formula (I)

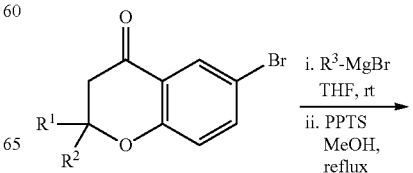

-continued

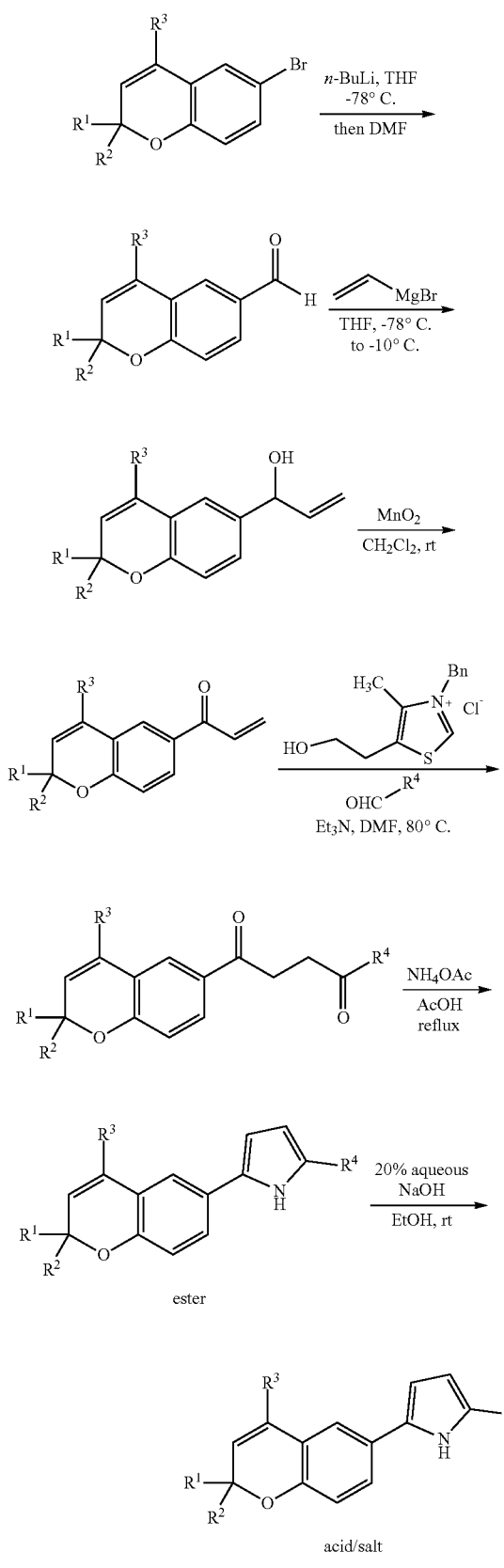

Example 1. Synthesis of Sodium 4-(5-(2,2-dimethyl-4-(p-tolyl)-2H-chromen-6-yl)-1H-pyrrol-2-yl)benzoate

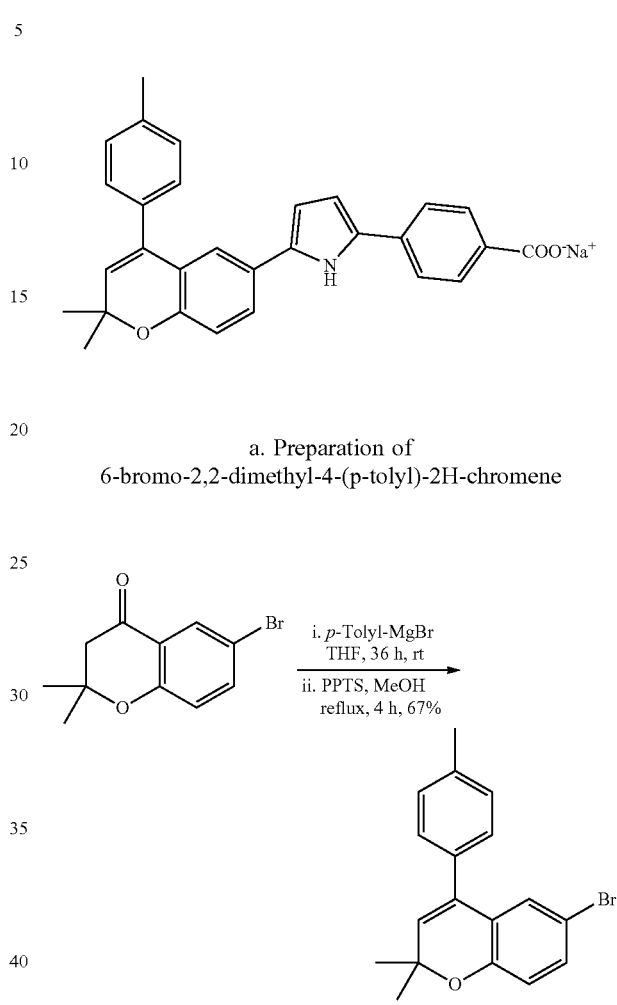

a. Preparation of 6-bromo-2,2-dimethyl-4-(p-tolyl)-2H-chromene

To a solution of ketone (8.00 g, 31.4 mmol, 1 eq.) in THF (20 mL), p-tolylmagnesium bromide (100 mL, 1 M in THF, 3.2 eq.) was added slowly over 15 minutes at 0° C. The reaction mixture was slowly warmed to room temperature and stirred for 36 h. Then the reaction was quenched with saturated NH$_4$Cl solution at 0° C. and extracted with EtOAc (40×3 mL) The organic layers were collected, washed with brine, dried over Na$_2$SO$_4$, and evaporated to obtain a semi-solid crude product. It was then dissolved in anhydrous MeOH (60 mL) and PPTS (1.60 g, 6.37 mmol, 0.2 eq.) was added to the reaction mixture and refluxed for 4 h. Then the solvent was evaporated under reduced pressure and the reaction mixture was dissolved in EtOAc:water (30 mL: 30 mL) and extracted with EtOAc (30×3 mL). Organic layer was washed with brine, dried over Na$_2$SO$_4$, and evaporated to dryness. Dried residue was purified by flash column chromatography (SiO$_2$, 100% hexanes to 5% EtOAc in hexanes) to obtain titled compound (6.89 g, 67%). $^1$H NMR (400 MHz, CD$_3$OD) δ 7.31-7.27 (m, 5H), 7.19 (d, J=2.3 Hz, 1H), 6.82 (d, J=8.5 Hz, 1H), 5.67 (s, 1H), 2.45 (s, 3H), 1.53 (s, 6H).

b. Preparation of 2,2-dimethyl-4-(p-tolyl)-2H-chromene-6-carbaldehyde

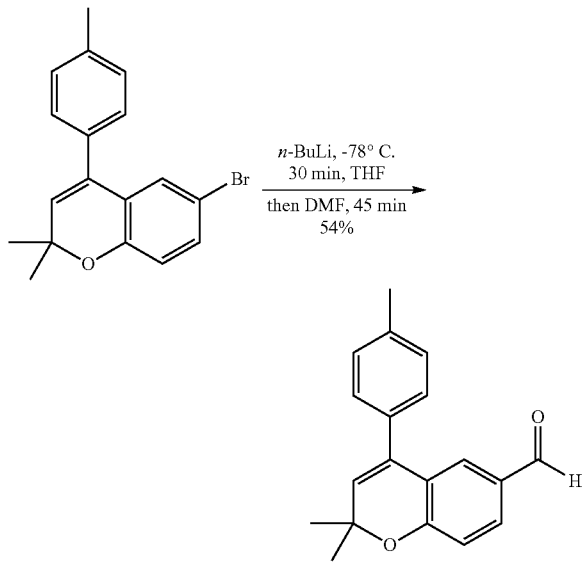

6-Bromochromene (2.43 g, 7.38 mmol) was dissolved in anhydrous THF (13 mL) and the reaction mixture was cooled to −78° C. To this, was added n-BuLi (4.20 mL, 6.64 mmol) and the reaction mixture was stirred for 30 minutes at −78° C. DMF (0.92 mL, 11.80 mmol) was then added to the reaction mixture at −78° C. and the reaction was stirred for additional 45 minutes at the same temperature. After the completion of the reaction as monitored by TLC, the reaction mixture was warmed to 0° C. and quenched with saturated NH$_4$Cl solution. The aqueous layer was extracted twice with ethyl acetate. The combined organic layer was dried over Na$_2$SO$_4$ and the solvent was evaporated. The crude reaction mixture was purified using flash column chromatography to obtain the titled compound as white solid (1.1 g, 54%). $^1$H NMR (400 MHz, CDCl$_3$) δ 9.79 (s, 1H), 7.73 (dd, J=8.3, 1.9 Hz, 1H), 7.58 (d, J=2.1 Hz, 1H), 7.31-7.23 (m, 4H), 7.00 (d, J=8.3 Hz, 1H), 5.68 (s, 1H), 2.44 (s, 3H), 1.55 (s, 6H). $^{13}$C NMR (100 MHz, CDCl$_3$) δ 190.9, 159.3, 138.1, 134.7, 133.9, 131.5, 129.9, 129.5, 129.4, 128.6, 127.9, 122.6, 117.6, 77.7, 28.3, 21.4.

c. Preparation of 1-(2,2-dimethyl-4-(p-tolyl)-2H-chromen-6-yl)prop-2-en-1-ol

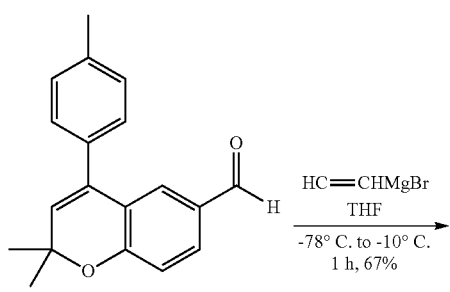

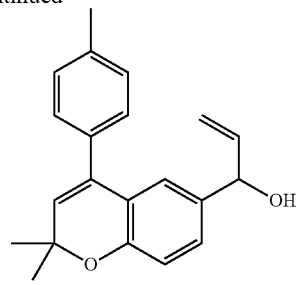

The aldehyde (1 g, 3.59 mmol) was dissolved in anhydrous THF (36 mL) and the reaction mixture was cooled to −78° C. To this was added vinylmagnesium bromide (4 mL, 3.59 mmol) and the reaction mixture was allowed to warm up slowly to −10° C. over 1 h. The reaction was quenched after complete conversion of starting material as monitored by TLC with saturated solution of ammonium chloride. The aqueous layer was extracted with ethyl acetate. The combined organic layer was dried over Na$_2$SO$_4$ and the solvent was evaporated. The crude reaction mixture was purified by using flash column chromatography to yield the allylic alcohol product as yellow viscous oil (743 mg, 67%). $^1$H NMR (400 MHz, CDCl$_3$) δ 7.27 (dd, J=12.7, 4.5 Hz, 4H), 7.19 (dd, J=8.3, 2.2 Hz, 1H), 7.07 (d, J=2.1 Hz, 1H), 6.90 (d, J=8.3 Hz, 1H), 6.03 (ddd, J=16.6, 10.3, 5.8 Hz, 1H), 5.63 (s, 1H), 5.30 (dt, J=17.2, 1.5 Hz, 1H), 5.17 (dt, J=10.5, 1.4 Hz, 1H), 5.08 (dd, J=5.7, 3.2 Hz, 1H), 2.44 (s, 3H), 1.85 (d, J=3.5 Hz, 1H), 1.51 (d, J=2.2 Hz, 6H). $^{13}$C NMR (100 MHz, CDCl$_3$) δ 153.2, 140.4, 137.6, 135.4, 134.9, 134.7, 136.9, 133.4, 130.1, 128.0, 127.3, 124.1, 122.5, 117.9, 114.9, 76.0, 75.2, 27.8, 27.7, 21.4.

d. Preparation of 1-(2,2-dimethyl-4-(p-tolyl)-2H-chromen-6-yl)prop-2-en-1-one

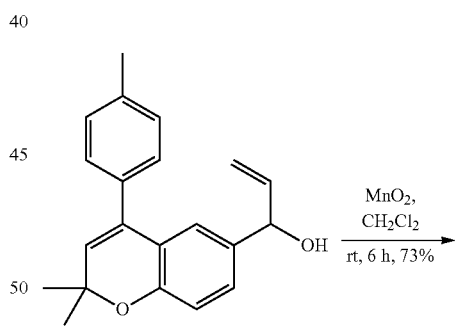

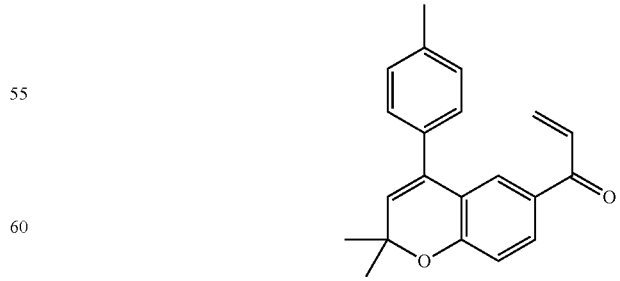

To a stirring solution of chromene-allylic alcohol (70 mg, 0.23 mmol) in anhydrous dichloromethane (2 mL) was added 8 equivalent of manganese dioxide (160 mg, 1.8 mmol, activated by heating in the oven for 1-2 h). The reaction was stirred at room temperature for 3 hours. To this was added another batch of manganese dioxide (160 mg, 1.8 mmol) and the resulting reaction mixture was stirred for an additional 2 hours after which TLC showed complete consumption of starting material. The reaction mixture was filtered through Celite® and the solvent was evaporated. The crude product was purified using flash column chromatography to obtain the vinyl ketone as a colorless viscous liquid (51 mg, 73%). $^1$H NMR (400 MHz, CDCl$_3$) δ 7.89 (dd, J=8.5, 2.1 Hz, 1H), 7.80-7.76 (m, 1H), 7.33-7.25 (m, 4H), 7.10 (dd, J=17.0, 10.5 Hz, 1H), 6.99 (d, J=8.4 Hz, 1H), 6.43 (dd, J=17.0, 1.9 Hz, 1H), 5.86 (dd, J=10.5, 1.8 Hz, 1H), 5.71 (s, 1H), 2.47 (s, 3H), 1.58 (s, 6H). $^{13}$C NMR (100 MHz, CDCl$_3$) δ 189.1, 158.0, 137.8, 134.6, 134.0, 132.0, 130.5, 130.1, 129.3, 129.1, 129.0, 128.4, 126.7, 122.1, 77.2, 27.9, 21.2.

e. Preparation of methyl 4-(4-(2,2-dimethyl-4-(p-tolyl)-2H-chromen-6-yl)-4-oxobutanoyl)benzoate

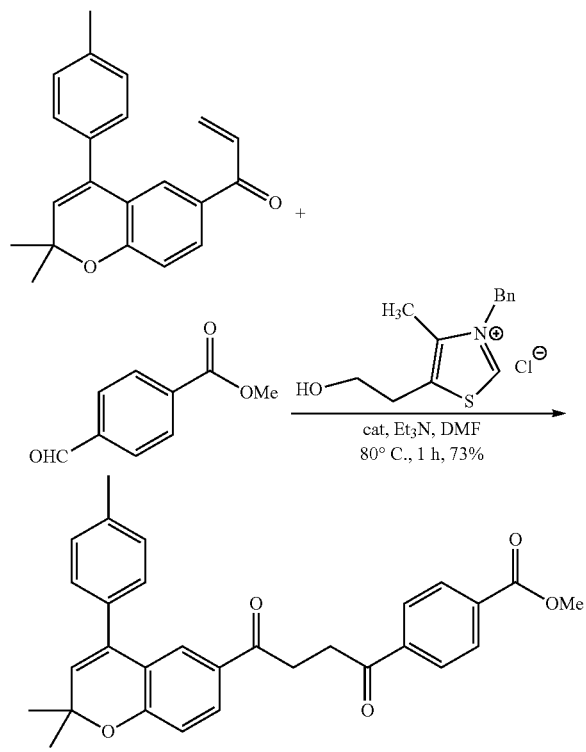

To a stirring solution of 1-(2,2-dimethyl-4-(p-tolyl)chroman-6-yl)prop-2-en-1-one (392 mg, 1.28 mmol) in DMF (4 mL) was added 3-benzyl-5-(2-hydroxyethyl)-4-methylthiazol-3-ium Chloride (69.1 mg, 0.26 mmol) followed by methyl 4-formylbenzoate (210 mg, 1.28 mmol) and triethylamine (0.2 ml, 1.54 mmol). The reaction mixture was degassed for 5-10 minutes and heated to 80° C. Upon completion as monitored by TLC, the reaction mixture was cooled to room temperature and diluted with ethyl acetate and water. The aqueous layer was extracted twice with ethyl acetate and the combined organic layer was dried (Na$_2$SO4) and evaporated. The crude product was purified using flash column chromatography. $^1$H NMR (400 MHz, CDCl$_3$) δ 8.16 (d, J=8.1 Hz, 2H), 8.09 (d, J=8.1 Hz, 2H), 7.95-7.87 (m, 1H), 7.78 (d, J=2.2 Hz, 1H), 7.31-7.22 (m, 4H), 6.96 (d, J=8.4 Hz, 1H), 5.68 (s, 1H), 3.98 (s, 3H), 3.44-3.38 (m, 2H), 3.38-3.33 (m, 2H), 2.42 (s, 3H), 1.55 (s, 6H). $^{13}$C NMR (101 MHz, CDCl$_3$) δ 198.5, 196.8, 166.2, 158.1, 140.1, 137.8, 134.6, 134.1, 133.8, 129.9, 129.8, 129.6, 129.3, 129.0, 128.4, 128.0, 126.1, 122.0, 116.8, 77.1, 52.4, 32.8, 32.1, 27.9, 21.2.

f. Preparation of methyl 4-(5-(2,2-dimethyl-4-(p-tolyl)-2H-chromen-6-yl)-1H-pyrrol-2-yl)benzoate

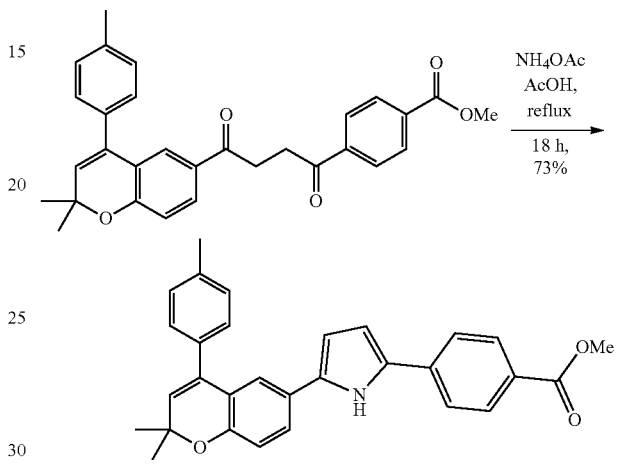

Methyl 4-(4-(2,2-dimethyl-4-(p-tolyl)-2H-chromen-6-yl)-4-oxobutanoyl)benzoate (440 mg, 0.939 mmol) was dissolved in glacial AcOH (16 mL) and to this was added ammonium acetate (362 mg, 4.70 mmol). The reaction mixture was then refluxed at 110° C. for 18 h. Upon completion as monitored by TLC the solvent was removed and crude product was dissolved in EtOAc (50 mL) and washed with saturated sodium bicarbonate solution. The combined organic layer was dried (Na$_2$SO$_4$), evaporated and purified using flash column chromatography. $^1$H NMR (400 MHz, CDCl$_3$) δ 8.55 (s, 1H), 8.00 (d, J=8.1 Hz, 2H), 7.50 (d, J=7.7 Hz, 2H), 7.36 (d, J=7.6 Hz, 1H), 7.29 (d, J=7.8 Hz, 3H), 7.23 (d, J=7.6 Hz, 3H), 6.93 (d, J=8.3 Hz, 1H), 6.65 (s, 1H), 6.38 (s, 1H), 5.66 (s, 1H), 3.90 (s, 3H), 2.42 (s, 3H), 1.51 (s, 6H). $^{13}$C NMR (101 MHz, CDCl$_3$) δ 130.3, 129.5, 129.2, 128.5, 127.0, 125.2, 125.0, 122.8, 121.6, 117.4, 109.7, 107.5, 76.1, 52.0, 27.6, 21.2.

g. Preparation of 4-(5-(2,2-dimethyl-4-(p-tolyl)-2H-chromen-6-yl)-1H-pyrrol-2-yl)benzoic Acid

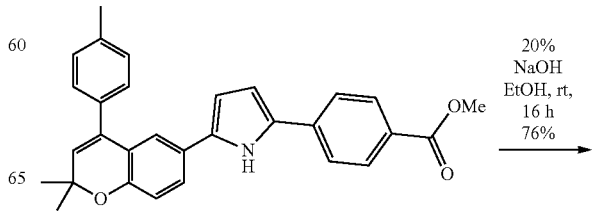

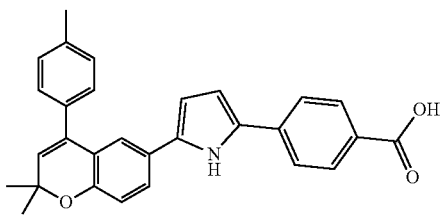

To a stirring solution of pyrrole ester (309 mg, 0.687 mmol) in ethanol (26 ml) was added NaOH solution (20% wt/wt, 3.44 mmol) and the reaction mixture was stirred for 48 h at room temperature till complete disappearance of starting material as monitored by TLC. The solvent was then evaporated and the reaction was acidified using 6N HCl to pH 6-7. The aqueous layer was extracted with ethyl acetate (2×50 ml)) and then with dichloromethane (2×50 ml). The combined organic layer was dried (Na$_2$SO$_4$) and the solvent was evaporated. The crude product was purified using flash column chromatography to yield the titled compound as a yellow solid (230 mg, 76%). $^1$H NMR (400 MHz, CD$_3$OD) δ 7.96 (d, J=8.2 Hz, 2H), 7.68 (d, J=8.2 Hz, 2H), 7.51 (dd, J=8.3, 2.2 Hz, 1H), 7.35-7.16 (m, 5H), 6.88 (d, J=8.4 Hz, 1H), 6.63 (d, J=3.6 Hz, 1H), 6.25 (d, J=3.7 Hz, 1H), 5.68 (s, 1H), 2.40 (s, 3H), 1.48 (s, 6H). $^{13}$C NMR (100 MHz, CD$_3$OD) δ 169.9, 153.7, 138.9, 138.8, 136.8, 136.6, 136.1, 132.9, 131.3, 130.3, 130.2, 129.7, 128.0, 127.2, 126.6, 124.1, 123.9, 123.1, 118.1, 110.5, 108.0, 76.9, 27.7, 21.3.

h. Preparation of Sodium 4-(5-(2,2-dimethyl-4-(p-tolyl)-2H-chromen-6-yl)-1H-pyrrol-2-yl)benzoate To a stirring solution of acid dissolved in methanol was added 1 M aqueous NaOH solution dropwise and the resulting mixture was stirred at rt for 30 mins. The solvent was evaporated and the crude reaction mixture was co-evaporated with toluene (3 times) to remove any traces of water. The solid was further washed with 5% aqueous acetone to remove any inorganic impurities and thereafter evaporated to dryness to yield the sodium salt as a yellow solid (quantitative yield). $^1$H NMR (400 MHz, CD$_3$OD) δ 7.91 (d, J=8.1 Hz, 2H), 7.59 (d, J=8.2 Hz, 2H), 7.51 (dd, J=8.4, 2.2 Hz, 1H), 7.29 (d, J=7.6 Hz, 5H), 6.87 (d, J=8.4 Hz, 1H), 6.53 (d, J=3.6 Hz, 1H), 6.22 (d, J=3.6 Hz, 1H), 5.69 (s, 1H), 2.42 (s, 3H), 1.49 (s, 6H). 13C NMR (100 MHz, CD$_3$OD) δ 175.6, 153.4, 138.8, 136.8, 136.3, 136.2, 135.8, 135.6, 133.8, 130.8 (2C), 130.2, 130.1 (2C), 129.7 (2C), 127.5, 126.4, 123.9, 123.9, 123.0, 118.1, 109.0, 108.9, 107.6, 76.9, 27.7 (2C), 21.3.

Example 2. Alternative Synthesis of Representative Compounds of Formula (I)

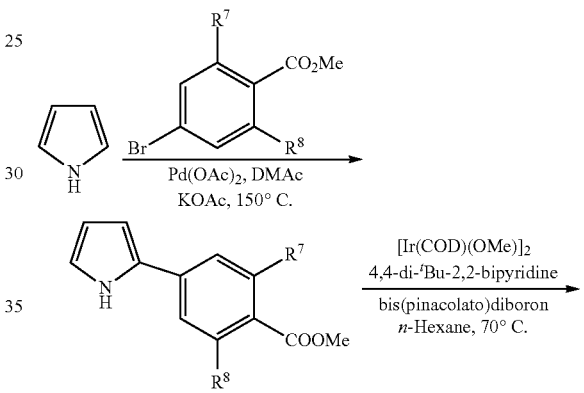

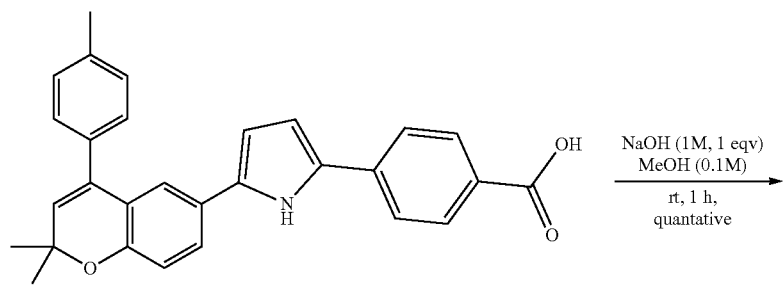

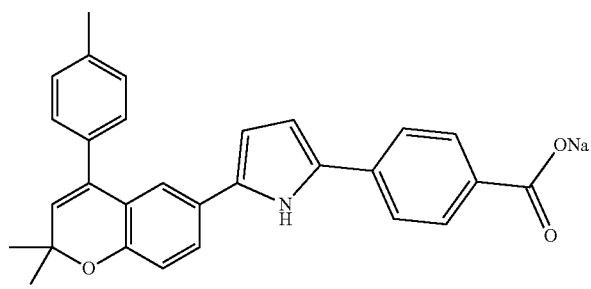

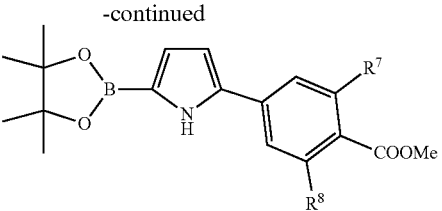

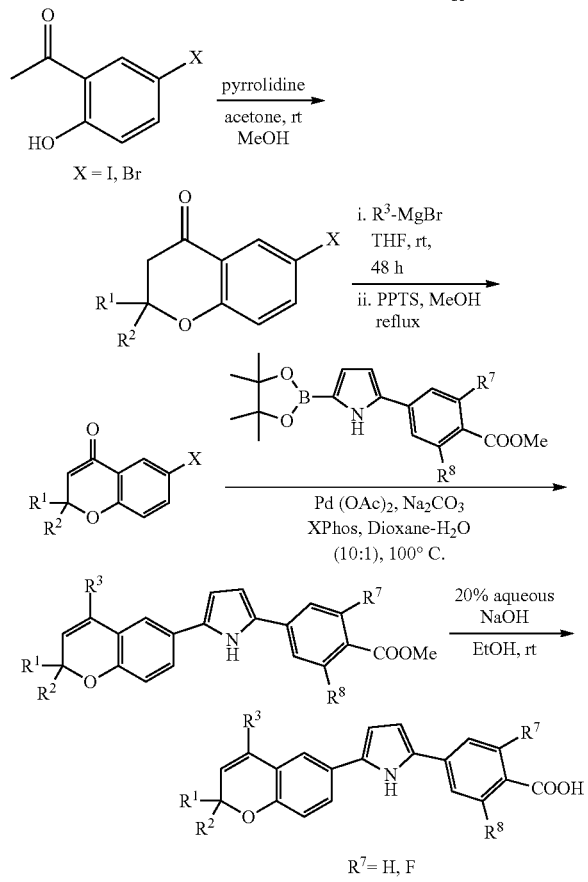

a. Preparation of tert-Butyl 2-(4-(methoxycarbonyl)phenyl)-1H-pyrrole-1-carboxylate

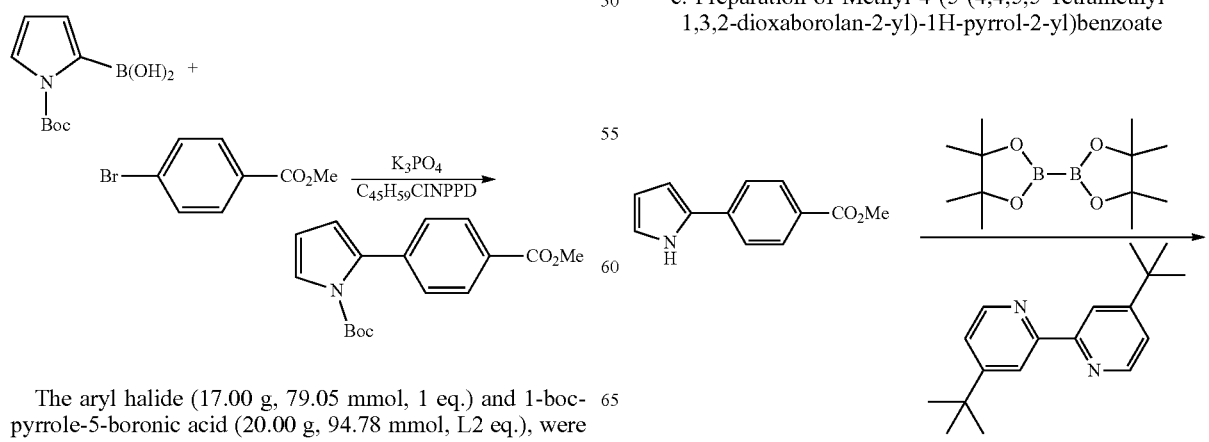

The aryl halide (17.00 g, 79.05 mmol, 1 eq.) and 1-boc-pyrrole-5-boronic acid (20.00 g, 94.78 mmol, L2 eq.), were combined in a round bottom flask followed by addition of THF (190 mL) and aqueous solution of $K_3PO_4$ (0.5 M, 380 mL, 2.4 eq.). Nitrogen gas was bubbled through the reaction mixture for 15 minutes followed by addition of XPhos Pd G2 (1.50 g, 1.91 mmol, 0.024 equiv.). Then the flask was placed in a preheated oil bath at 45° C. and stirred for 5 hours. After the reaction was complete, brine was added and the mixture was extracted with EtOAc (50 mL×3) and dried with $MgSO_4$. The solvent was evaporated to dryness. The residue was purified by flash column chromatography ($SiO_2$, 100% hexanes to 20% EtOAc in hexanes) to obtain the coupled product as a white solid (22.142 g, 93%). $^1$H NMR (400 MHz, $CDCl_3$) δ 8.06-7.98 (m, 2H), 7.45-7.35 (m, 3H), 6.29-6.21 (n, 2H), 3.93 (s, 3H), 1.37 (s, 9H) $^{13}$C NMR (100 MHz, $CDCl_3$) δ 167.1, 149.3, 139.1, 134.1, 129.1, 128.7, 123.6, 115.6, 111.0, 84.2, 52.2, 27.8 This compound is also commercially available.

b. Preparation of Methyl 4-(1H-Pyrrol-2-yl)benzoate

The product from step a (18.13 g, 60.16 mmol, 1 eq.) was dissolved in THF (60 mL) and NaOMe (80 mL, 25 wt,% in MeOH, 6 eq.) was added. The mixture was stirred for 5 minutes and quenched with saturated $NH_4Cl$ solution. The resulting mixture was extracted with dichloromethane (50 mL×3) and the organic phase was dried with $MgSO_4$ and evaporated to dryness to provide the deprotected product as a white solid (11.615 g, 96%). $^1$H NMR (400 MHz, $CDCl_3$) δ 8.62 (s, 1H), 8.09-8.01 (m, 2H), 7.59-7.51 (m, 2H), 6.95 (td, J=2.7, 1.4 Hz, 1H), 6.69 (ddd, J=3.8, 2.7, 1.4 Hz, 1H), 6.36 (dt, J=3.7, 2.6 Hz, 1H), 3.94 (s, 3H). $^{13}$C NMR (100 MHz, $CDCl_3$) δ 166.9, 136.8, 131.0, 130.4, 127.3, 1231, 120.3, 110.7, 108.0, 52.1.

c. Preparation of Methyl 4-(5-(4,4,5,5-Tetramethyl-1,3,2-dioxaborolan-2-yl)-1H-pyrrol-2-yl)benzoate

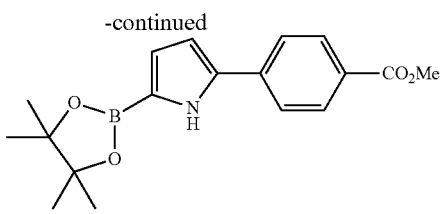

The product from step b (12.00 g, 59.63 mmol, 1 eq.), B₂Pin₂ (8.304 g, 32.7 mmol, 0.55 eq.) [Ir(COD)OMe] (0.60 g, 0.91 mmol, 0.015 eq.), and 4,4'-dtbpy (0.484 g, 1.80 mmol, 0.03 eq) were combined in a round bottom flask, evacuated under vacuum, and purged with nitrogen. This process was repeated three times followed by mixing with hexanes (120 mL). The suspension was refluxed under nitrogen for 6 hours. After 6 hours, the reaction mixture was solubilized in DCM and a silica gel slurry was prepared for flash chromatography (SiO, 100% hexanes to 20% EtOAc in hexanes) to obtain the pyrrole boronate product as an off-white solid (16.71 g, 86%). %). ¹H NMR (400 MHz, CDCl₃) δ 8.99 (s, 1H), 8.07-8.00 (m, 2H), 7.63-7.56 (m, 2H), 6.89 (dd, J=3.7, 2.4 Hz, 1H), 6.69 (dd, J=3.7, 2.5 Hz, 1H), 3.92 (s, 3H), 1.34 (s, 12H). ¹³C NMR (101 MHz, CDCl₃) δ 167.0, 136.4, 135.6, 130.5, 128.2, 124.0, 122.1, 109.3, 84.1, 52.2, 24.9.

d. Preparation of 6-Bromo-2,2-dimethyl-4-(p-tolyl)-2H-chromene

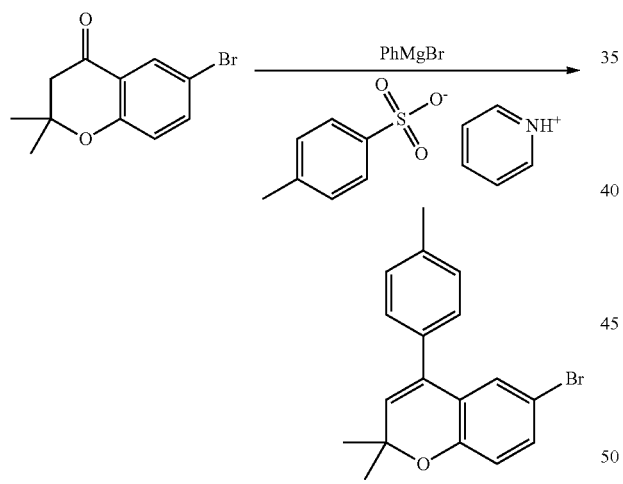

To a solution of bromochromone (8.00 g, 31.4 mmol, 1 eq.) in THF (20 mL), p-tolylmagnesium bromide (100 mL, 1 M in THF, 3.2 eq.) was added slowly over 15 minutes at 0° C. The reaction mixture was slowly warmed to room temperature and stirred for 36 hours. The reaction was quenched with saturated NH₄Cl solution at 0° C. and extracted with EtOAc (40×3 mL). The organic layers were collected, washed with brine, dried over MgSO₄, and evaporated to obtain a semisolid crude product. The semisolid crude product was dissolved in anhydrous MeOH (60 mL) and PPTS (1.60 g, 6.37 mmol, 0.2 eq.) was added. The resulting mixture was allowed to reflux for 4 hours. The solvent was evaporated under reduced pressure and the resulting material was dissolved in EtOAc:water (30 mL:30 mL) and extracted with EtOAc (30×3 mL). The combined organic layers were washed with brine, dried over MgSO₄, and evaporated to dryness. The residue was purified by flash column chromatography (SiO₂, 100% hexanes to 5% EtOAc in hexanes) to provide the bromochromene product (6.89 g, 67%) as a colorless liquid that turned solid upon freezing. ¹H NMR (400 MHz, CD₃OD) δ 7.31-7.27 (m, 5H), 7.19 (d, J=2.3 Hz, 1H), 6.82 (d, J=8.5 Hz, 1H), 5.67 (s, 1H), 2.45 (s, 3H), 1.53 (s, 6H). ¹³C NMR (100 MHz, CD₃OD) δ 152.5, 137.8, 134.8, 133.9, 131.8, 129.8, 129.3, 128.5, 128.2, 124.5, 118.7, 112.8, 76.2, 27.6, 21.3.

e. Preparation of methyl 4-(5-(2,2-dimethyl-4-(p-tolyl)-2H-chromen-6-yl)-1H-pyrrol-2-yl)benzoate

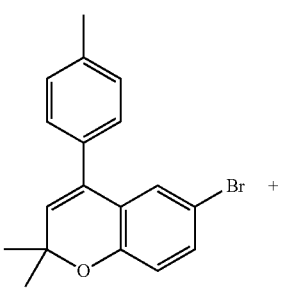

The bromochromene from step d (580 mg, 1.76 mmol, 1 eq.) and the pyrrole boronate from step c (630 mug, 1.93 mmol, 1, eq.), were combined in a vial and dissolved into THF (3.5 mL) and an aqueous solution of K₃PO₄ (0.5 M, 7 mL, 2.0 eq.) was added. Nitrogen gas was bubbled through the reaction mixture for 15 minutes followed by addition of XPhos Pd G2 (0.035 g, 0.04 mmol, 0.025 eq.). The mixture was placed in a preheated oil bath at 45° C. and stirred for 3 hours, After the reaction was complete, brine was added and the resulting mixture was extracted with EtOAc (50 ml×3). The combined organics were dried over MgSO₄ and evaporated to dryness. The residue was purified by flash column chromatography (SiO₂, 100% hexanes to 20% EtOAc in hexanes) to provide the chromene ester product as a bright yellow solid (681 g, 86%).

f. Preparation of 4-(5-(2,2-dimethyl-4-(p-tolyl)-2H-chromen-6-yl)-1H-pyrrol-2-yl)benzoic Acid

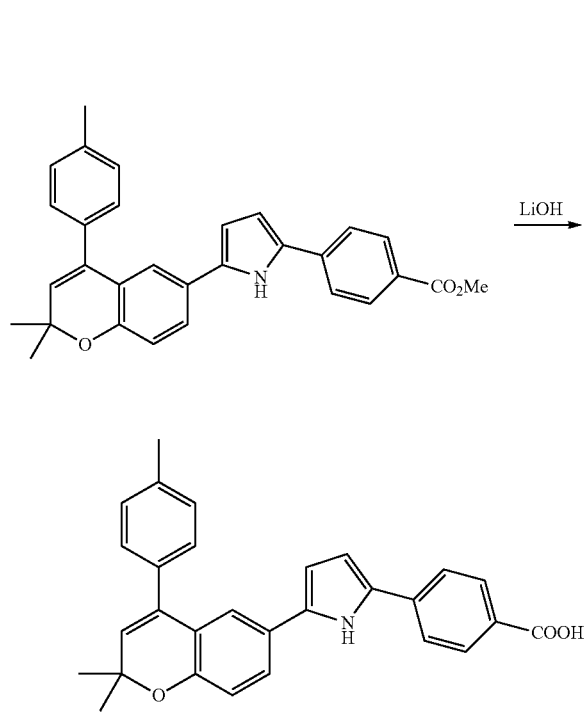

To a solution of chromene ester product (600 ng, 1.33 mmol, 1 eq.) in THF (10 mL) and MeOH (10 mL), was added LiOH (280 mg, 6.67 mmol, 5 eq.) dissolved in water (10 mL) and the resulting mixture was stirred for 20 hours at room temperature. The organic layer was evaporated under reduced pressure and the aqueous suspension was acidified with 2N HCl to reach pH 1.0. Then mixture was extracted with EtOAc (10 mL×3), washed with brine, and dried with MgSO$_4$. The extract was purified by flash column chromatography (SiO$_2$, 100% hexanes to 50% EtOAc and 2% HCOOH in hexanes) to provide the acid (526 mg, 91%) as a yellow solid.

Example 3 Sodium 4-(5-(2,2-dimethyl-4-(p-tolyl)-2H-chromen-6-yl)-1H-pyrrol-2-yl)-2-fluorobenzoate

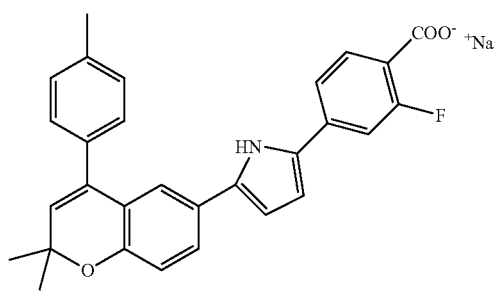

a. Preparation of methyl 2-fluoro-4-(1H-pyrrol-2-yl)benzoate

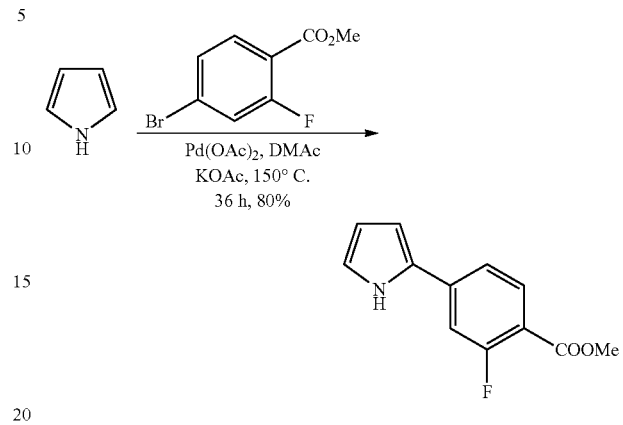

To a stirring solution of 1H-pyrrole (230 mg, 238 µL, 4 Eq, 3.43 mmol) in N,N-dimethylacetamide (3 mL, 0.3 molar) was added palladium(II) acetate (9.63 mg, 0.05 Eq, 42.9 µmol), potassium acetate (168 mg, 2 Eq, 1.72 mmol) and methyl 4-bromo-2-fluorobenzoate (200 mg, 1 Eq, 858 µmol). The solution was degassed using nitrogen for 15 minutes. The resulting solution was heated in a sealed tube at 150° C. for 36 hours. The reaction mixture was purified directly using flash column chromatography to give the titled compound (150 mg, 80%). $^1$H NMR (400 MHz, CDCl$_3$) δ 8.59 (s, 1H), 7.93 (t, J=8.0 Hz, 1H), 7.28 (dd, J=8.3, 1.7 Hz, 1H), 7.20 (dd, J=12.2, 1.8 Hz, 1H), 6.94 (td, J=2.7, 1.3 Hz, 1H), 6.67 (dq, J=3.8, 1.6 Hz, 1H), 6.34 (q, J=2.8 Hz, 1H), 3.93 (s, 3H).

b. Preparation of methyl 2-fluoro-4-(5-(4,4,5,5-tetramethyl-1,3,2-dioxaborolan-2-yl)-1H-pyrrol-2-yl)benzoate

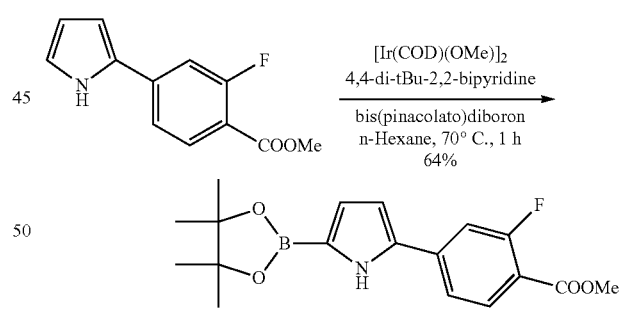

To a solution of methyl 2-fluoro-4-(1H-pyrrol-2-yl)benzoate (141 mg, 1 Eq, 0.643 mmol) in anhydrous n-hexane (5.88 mL, 0.170 molar) were added 4,4'-di-tert-butyl-2,2'-bipyridine (5.18 mg, 0.030 Eq, 19.3 µmol), bis(pinacolato)diboron (163 mg, 1 Eq, 643 µmol) and (1,5-Cyclooctadiene)(methoxy)iridium (I) dimer (6.39 mg, 0.015 Eq, 9.64 µmol). The resulting mixture (not homogeneous) was heated to reflux and stirred for 1 and half hour (Within 1 h of heating the reaction color changed to dark brown and reaction mixture becomes homogeneous). The crude mixture was then evaporated and directly purified using flash column chromatography to provide the titled compound (142 mg, 64%). $^1$H NMR (400 MHz, CDCl$_3$) δ 9.13 (s, 1H), 7.96 (t, J=7.9 Hz, 1H), 7.37 (dd, J=8.3, 1.7 Hz, 1H), 7.30 (dd, J=12.3, 1.6 Hz, 1H), 6.90 (dd, J=3.7, 2.3 Hz, 1H), 6.71 (dd, J=3.7, 2.5 Hz, 1H), 3.95 (s, 3H), 1.36 (s, 12H).

c. Preparation of 6-Iodo-2,2-dimethylchroman-4-one

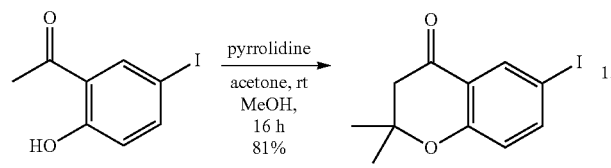

To a solution of 1-(2-hydroxy-5-iodophenyl)ethan-1-one (2.00 g, 1 Eq, 7.63 mmol) in methanol (40.0 mL, 0.19 molar, 1.0 Eq, 7.6 mmol) were added pyrrolidine (847 mg, 0.98 mL, 1.56 Eq, 11.9 mmol) and acetone (678 mg, 0.86 mL, 1.53 Eq, 11.7 mmol). The reaction mixture was left stirring overnight. TLC showed complete consumption of starting material, MeOH was evaporated and the crude mixture was washed with 1N HCl (aqueous), extracted with EtOAc. The crude reaction mixture was dried over $Na_2SO_4$ and evaporated. The resulting residue was purified on flash column chromatography (silica gel, hexanes/ethyl acetate, 100:00 to 70:30) to give the titled compound (1.86 g, 81%, brown oil). $^1$H NMR (400 MHz, $CDCl_3$) δ 8.12 (d, J=2.3 Hz, 1H), 7.68 (dd, J=8.7, 2.3 Hz, 1H), 6.69 (d, J=8.7 Hz, 1H), 2.69 (s, 2H), 1.43 (s, 6H). $^{13}$C NMR (100 MHz, $CDCl_3$) δ 191.1, 159.6, 144.4, 135.2, 122.1, 120.9, 82.9, 79.7, 48.5, 26.6.

d. Preparation of 6-iodo-2,2-dimethyl-4-(p-tolyl)-2H-chromene

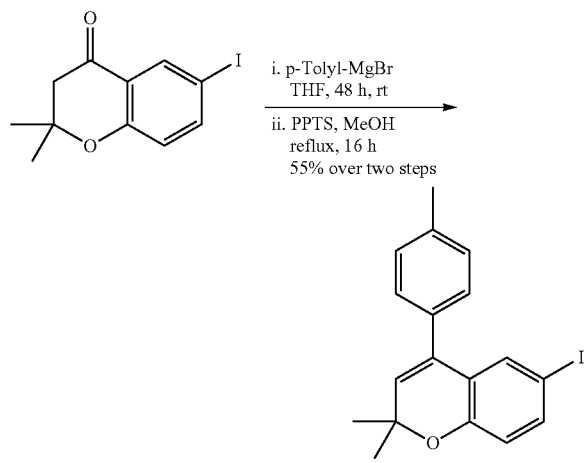

The title compound was prepared compound (55% off-white solid) following the procedure described for its bromo analog. $^1$H NMR (400 MHz, $CDCl_3$) 7.47 (dd, J=8.5, 2.2 Hz, 1H), 7.34 (d, J=2.2 Hz, 1H), 7.26 (s, 4H), 6.70 (d, J=8.5 Hz, 1H), 5.64 (s, 1H), 2.45 (s, 3H), 1.52 (s, 6H).

e. Preparation of methyl 4-(5-(2,2-dimethyl-4-(p-tolyl)-2H-chromen-6-yl)-1H-pyrrol-2-yl)-2-fluorobenzoate

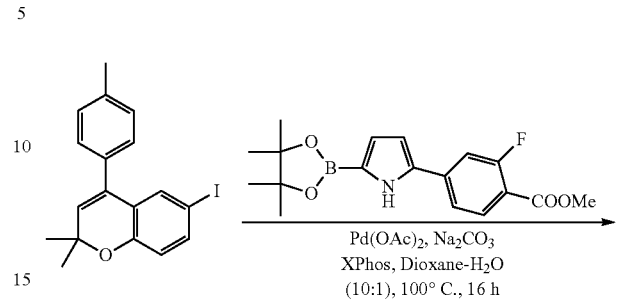

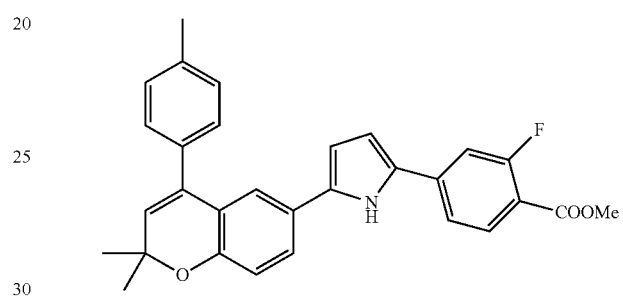

To a mixture of 6-iodo-2,2-dimethyl-4-(p-tolyl)-2H-chromene (154 mg, 1 Eq, 0.408 mmol) and methyl 2-fluoro-4-(5-(4,4,5,5-tetramethyl-1,3,2-dioxaborolan-2-yl)-1H-pyrrol-2-yl)benzoate (141 mg, 1.00 Eq, 0.408 mmol) in 1,4-dioxane (12.36 mL, 0.033 molar) and water (1.24 mL, 0.33 molar) were added sodium carbonate (303 mg, 7 Eq, 2.86 mmol), diacetoxypalladium (14.7 mg, 0.160 Eq, 0.0653 mmol) and dicyclohexyl(2',4',6'-triisopropyl-[1,1'-biphenyl]-2-yl)phosphane (97.3 mg, 0.500 Eq, 0.204 mmol). The resulting solution was degassed for 15 minutes using $N_2$ gas. The reaction mixture was then refluxed at 100° C. for 16 h. The crude reaction mixture was evaporated to dryness and purified via flash column chromatography to afford the titled compound (149 mg, 78%). $^1$H NMR (400 MHz, $CDCl_3$) δ 8.75 (s, 1H), 7.81 (t, J=8.0 Hz, 1H), 7.30 (dd, J=8.4, 2.2 Hz, 1H), 7.23-7.10 (m, 7H), 6.84 (d, J=8.3 Hz, 1H), 6.57 (t, J=3.2 Hz, 1H), 6.33-6.25 (m, 1H), 5.57 (s, 1H), 3.83 (s, 3H), 2.33 (s, 3H), 1.43 (s, 6H).

f. Preparation of sodium 4-(5-(2,2-dimethyl-4-(p-tolyl)-2H-chromen-6-yl)-1H-pyrrol-2-yl)-2-fluorobenzoate

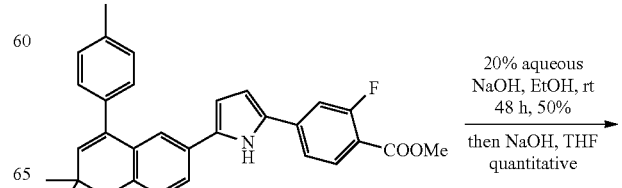

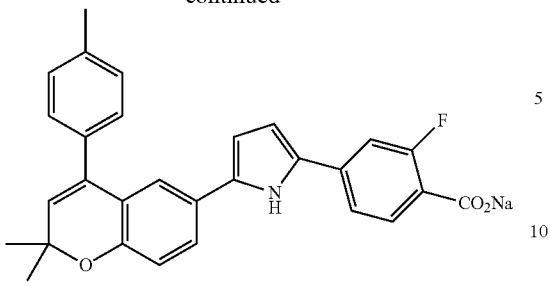

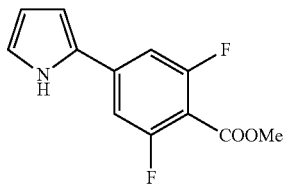

To a stirring solution of pyrrole ester (97 mg, 0.21 mmol) in ethanol (2.0 mL) was added aqueous sodium hydroxide solution (5 M, 1 mmol) and the reaction mixture was stirred for 48 h at room temperature till complete disappearance of starting material as monitored by TLC. The solvent was then evaporated, and the reaction was acidified using 6N HCl to pH 6-7. The aqueous layer was extracted with ethyl acetate (2×10 ml)) and then with dichloromethane (2×10 mL). The combined organic layer was dried over sodium sulfate and the solvent was evaporated to give acid (47 mg, 50%). To a stirring solution of acid (20 mg, 44 mmol) dissolved in anhydrous MeOH (0.44 mL) was added sodium hydroxide (1 M, 40 mL) and the resulting mixture was stirred at room temperature for 30 minutes. The solvent was evaporated and the crude reaction mixture was co-evaporated with toluene (3 times) to remove any traces of water. The crude solid was purified using reverse phase column chromatography to give the titled compound (quantitative yield). $^1$H NMR (400 MHz, MeOD) δ 7.64 (t, J=8.0 Hz, 1H), 7.49 (dd, J=8.3, 2.2 Hz, 1H), 7.38-7.32 (m, 1H), 7.28 (d, J=12.4 Hz, 5H), 6.86 (d, J=8.4 Hz, 1H), 6.53 (d, J=3.6 Hz, 1H), 6.21 (d, J=3.6 Hz, 1H), 5.68 (s, 1H), 2.40 (s, 3H), 1.48 (s, 6H).

To a mixture of methyl 4-bromo-2,6-difluorobenzoate (300.00 mg, 1 Eq, 1.1951 mmol) and 2-(4,4,5,5-tetramethyl-1,3,2-dioxaborolan-2-yl)-1H-pyrrole (576.77 mg, 2.5 Eq, 2.9877 mmol) in 1,4-dioxane (36.2 mL, 0.033 molar) and water (3.62 mL, 0.330 molar) were added sodium carbonate (886.66 mg, 7 Eq, 8.37 mmol), diacetoxypalladium (42.93 mg, 0.16 Eq, 191.21 μmol) and Xphos (dicyclohexyl(2',4',6'-triisopropyl-[1,1'-biphenyl]-2-yl)phosphane) (284.9 mg, 0.5 Eq, 597.5 μmol). The resulting solution was degassed for 15 minutes using $N_2$ gas. The reaction mixture was then refluxed at 100° C. for 16 h. The crude reaction mixture was evaporated to dryness and purified via flash column chromatography to yield the titled compound (181 mg, 64%) as white solid. $^1$H NMR (400 MHz, CDCl$_3$) δ 9.93 (s, 1H), 7.10-7.01 (m, 2H), 6.89 (td, J=2.8, 1.4 Hz, 1H), 6.61 (ddd, J=3.9, 2.6, 1.4 Hz, 1H), 6.26 (dt, J=3.7, 2.5 Hz, 1H), 3.90 (s, 3H).

b. Preparation of methyl 2,6-difluoro-4-(5-(4,4,5,5-tetramethyl-1,3,2-dioxaborolan-2-yl)-1H-pyrrol-2-yl)benzoate Example 4 Sodium 4-(5-(2,2-dimethyl-4-(p-tolyl)-2H-chromen-6-yl)-1H-pyrrol-2-yl)-2,6-difluorobenzoate

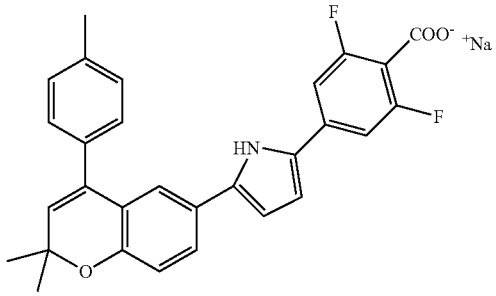

a. Preparation of methyl 2,6-difluoro-4-(1H-pyrrol-2-yl)benzoate

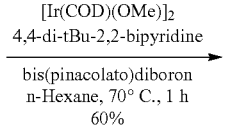

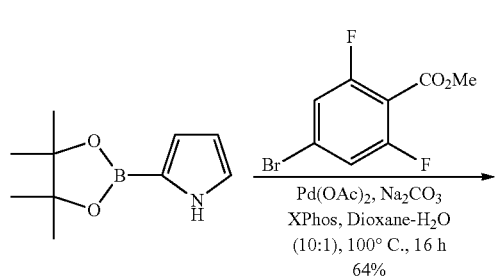

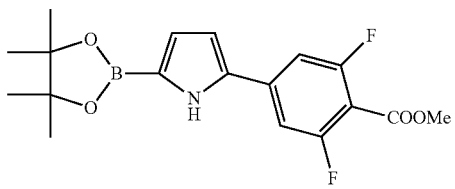

The titled compound (234 mg, 60%) was prepared following the procedure described for its mono-flouro analog. $^1$H NMR (400 MHz, CDCl$_3$) δ 9.06 (s, 1H), 7.12-7.05 (m, 2H), 6.86 (dd, J=3.7, 2.3 Hz, 1H), 6.66 (dd, J=3.7, 2.5 Hz, 1H), 3.94 (s, 3H), 1.33 (s, 12H).

c. Preparation of methyl 4-(5-(2,2-dimethyl-4-(p-tolyl)-2H-chromen-6-yl)-1H-pyrrol-2-yl)-2,6-difluorobenzoate

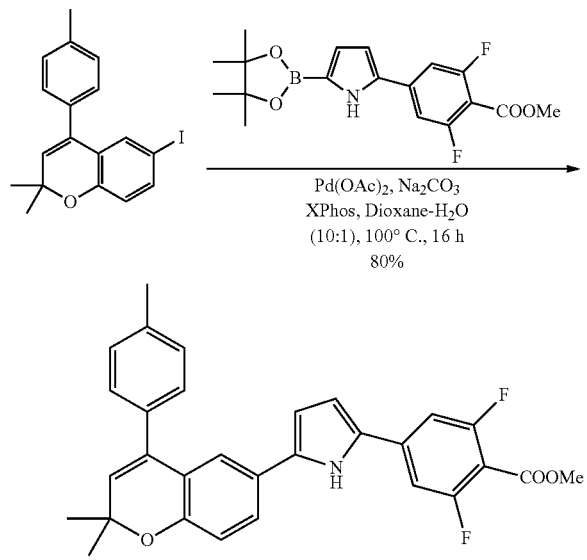

The titled compound was prepared using a procedure similar to that described in Example 3, sub-part e (33 mg, 80%). $^1$H NMR (400 MHz, CDCl$_3$) δ 8.59 (s, 1H), 7.41-7.34 (m, 1H), 7.27 (dt, J=13.4, 6.8 Hz, 5H), 7.01 (d, J=10.1 Hz, 2H), 6.95 (d, J=8.3 Hz, 1H), 6.65 (t, J=3.2 Hz, 1H), 6.40 (d, J=3.2 Hz, 1H), 5.68 (s, 1H), 3.94 (s, 3H), 2.44 (s, 3H), 1.53 (s, 6H).

d. Preparation of sodium 4-(5-(2,2-dimethyl-4-(p-tolyl)-2H-chromen-6-yl)-1H-pyrrol-2-yl)-2,6-difluorobenzoate

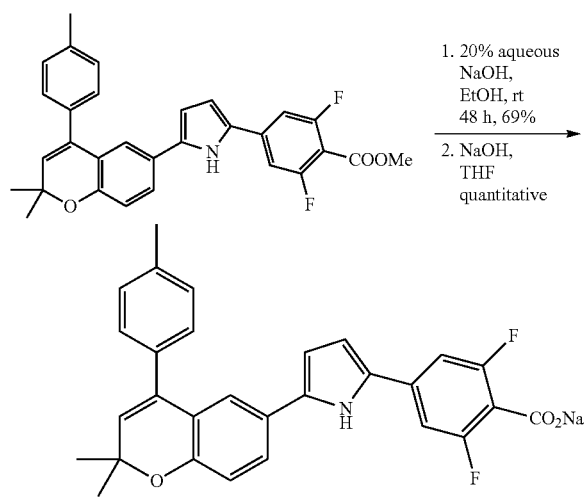

The titled compound was prepared using a procedure similar to that described in Example 3, sub-part f (68 mg, 69%). $^1$H NMR (400 MHz, MeOD) δ 7.49 (dd, J=8.4, 2.2 Hz, 1H), 7.32-7.23 (m, 5H), 7.17 (d, J=8.6 Hz, 2H), 6.87 (d, J=8.3 Hz, 1H), 6.53 (d, J=3.7 Hz, 1H), 6.21 (d, J=3.7 Hz, 1H), 5.68 (s, 1H), 2.40 (s, 3H), 1.48 (s, 6H).

Example 5. Metabolic Stability Assays

The metabolic stability of the compound of Example 1 was evaluated using standard assay protocols. Results are provided in the following tables.

Metabolic Stability of Test Compounds in Male Mouse Liver Microsomes

| Compound | Remaining Percentage (%) @ 60 min | |
| --- | --- | --- |
| | With NADPH | Without NADPH |
| Verapamil | 2.68 | 104.75 |
| Example 1 | 86.20 | 94.70 |
| Verapamil | 2.68 | 104.75 |
| Example 1 | 86.20 | 94.70 |

Metabolic Stability of Test Compounds in Pooled Human Liver Microsomes (a)

| Compound | Species | $T_{1/2}$ (min) | $CL_{int}$ (μL/min/mg protein) | Scaled-up $CL_{int}$ (mL/min/Kg) |
| --- | --- | --- | --- | --- |
| Verapamil | Human | 15.39 | 90.08 | 112.97 |
| Example 1 | Human | 569.64 | 2.43 | 3.05 |

Metabolic Stability of Test Compounds in Pooled Human Liver Microsomes (b)

| Compound | Species | Assay Format | Remaining Percentage (%) | | | | |
| --- | --- | --- | --- | --- | --- | --- | --- |
| | | | 0 min | 15 min | 30 min | 45 min | 60 min |
| Verapamil | Human | With NADPH | 100.00 | 32.16 | 15.37 | 9.09 | 6.42 |
| | | Without NADPH | 100.00 | 105.07 | 94.01 | 91.24 | 94.01 |
| Example 1 | Human | With NADPH | 100.00 | 97.20 | 104.60 | 95.66 | 92.01 |
| | | Without NADPH | 100.00 | 104.88 | 89.43 | 98.37 | 101.63 |

Example 6. Stability in Mouse and Human Hepatocytes

The metabolic stability of the compound of Example 1 was evaluated in mouse and human hepatocytes using standard assay protocols. Results are provided in the following tables.

Metabolic Stability of Test Compounds in Human and Mouse Hepatocytes

| Compound | Species | In vitro $T_{1/2}$ (min) | In vitro $Cl_{int}$ (μL/min/10$^6$ cells) | Scale-up $Cl_{int}$ (mL/min/kg) |
| --- | --- | --- | --- | --- |
| Verapamil | Human | 25.90 | 53.51 | 136.15 |
| | Mouse | 16.13 | 85.94 | 1015.14 |

Metabolic Stability of Test Compounds in Human and Mouse Hepatocytes

| Compound | Species | In vitro $T_{1/2}$ (min) | In vitro $Cl_{int}$ (μL/min/$10^6$ cells) | Scale-up $Cl_{int}$ (mL/min/kg) |
|---|---|---|---|---|
| Example 1 | Human | 522.36 | 2.65 | 6.75 |
|  | Mouse | 289.56 | 4.79 | 56.54 |

Metabolic Stability of Test Compounds in Human and Mouse Hepatocytes

| Compound | Species | Assay Format | Remaining Percentage (%) | | | | |
|---|---|---|---|---|---|---|---|
|  |  |  | 0 min | 15 min | 30 min | 60 min | 90 min | 120 min |
| Verapamil | Human | Hepatocytes | 100.00 | 54.52 | 30.15 | 13.32 | 7.23 | 3.73 |
|  |  | Boiled hepatocytes | 100.00 | 95.35 | 87.21 | 98.15 | 92.27 | 96.98 |
|  | Mouse | Hepatocytes | 100.00 | 43.64 | 18.29 | 6.52 | 1.90 | 0.61 |
|  |  | Boiled hepatocytes | 100.00 | 92.58 | 91.42 | 89.53 | 86.22 | 87.28 |
| Example 1 | Human | Hepatocytes | 100.00 | 90.54 | 100.06 | 94.23 | 84.66 | 84.71 |
|  |  | Boiled hepatocytes | 100.00 | 98.16 | 81.83 | 94.26 | 96.14 | 89.50 |
|  | Mouse | Hepatocytes | 100.00 | 90.50 | 90.43 | 87.11 | 76.03 | 74.05 |
|  |  | Boiled hepatocytes | 100.00 | 92.45 | 99.92 | 103.79 | 113.92 | 107.73 |

Example 7. Log D Calculations

The Log D's for the compound of Example 1 and progesterone were determined using standard assay protocols. Results are provided in the following table.

Log D Results of Test Compounds in 1-Octanol/PBS pH 7.4

| Compound | LogD Value |
|---|---|
| Progesterone | 3.77 |
| Example 1 | 3.40 |

Example 8. Solubility Measurements

The stabilities of the compound of Example 1 and progesterone in PBS at pH 7.4 were determined using standard assay protocols. Results are provided in the following table.

Solubility Results of Test Compounds and Control Compound in PBS at pH 7.4

| Compound | Solubility (μM) |
|---|---|
| Progesterone | 14.02 |
| Example 1 | 78.57 |

Example 9. hERG Assay

The potential inhibitory effect on human Ether-á-go-go related gene (hERG) channel was evaluated using a manual patch-clamp system. A HEK293 cell line stably transfected with hERG gene was employed. Dofetilide was used as a positive control. The results are shown in the following tables. From this data, the compound of Example 1 is ranked as a weak inhibitor on hERG channel.

| Compound | Concentration (μM) | % of hERG inhibition Cell 1 | % of hERG inhibition Cell 2 | Average % of inhibition hERG | SD |
|---|---|---|---|---|---|
| Example 1 | 0.37 | −0.16 | −2.51 | −1.33 | 1.66 |
|  | 1.11 | 3.73 | 3.62 | 3.68 | 0.08 |
|  | 3.33 | 6.99 | 16.45 | 11.72 | 6.69 |
|  | 10.00 | 19.54 | 20.16 | 19.85 | 0.44 |
|  | 30.00 | 35.90 | 43.18 | 39.54 | 5.14 |
| Dofetilide | 0.00185 | 3.38 | 8.52 | 5.95 | 3.64 |
|  | 0.00556 | 12.81 | 11.40 | 12.11 | 1.00 |
|  | 0.01667 | 53.60 | 53.10 | 53.35 | 0.35 |
|  | 0.05000 | 82.47 | 85.29 | 83.88 | 2.00 |
|  | 0.15000 | 96.14 | 94.20 | 95.17 | 1.37 |

| Test article | hERG $IC_{50}$ [μM] | Comment |
|---|---|---|
| Compound of Example 1 | >30[1] | 39.54% inhibition @ 30 μM |
| Dofetilide | 0.016 [2] | — |

Example 10. Mini-Ames Assay

The compound of Example 1 was evaluated in a mini-Ames assay. The results were negative.

Example 11. HepG2 and Human Liver Fibroblast Assay

The compound of Example 1 was evaluated in a HepG2 cytotoxicity assay. The results were negative.

Example 12. Human Liver Fibroblast Assay

The compound of Example 1 was evaluated in a human liver fibroblast assay. The results were negative.

The data from Examples 5-12 is summarized below.

Summary of In Vitro Assays

Metabolic Stability (mouse): 86% after 1 hour
Metabolic Stability (human): 100% after 1 hour, $t_{1/2}$-570 minutes
Log D=3.5
Solubility: 2 mg/ml (saline)
hERG (negative, >30 μm)
Mini Ames (negative)
HepG2 cytotoxicity assay (negative)
Human lung fibroblast assay (negative)

Example 13. Transactivation Assay

A dose-response of agonist, 9-cis-retinoic acid (9-cis-RA) for RARα or all-trans-retinoic acid (ATRA) for RAR β and γ, and reference antagonists BMS-189453 or BMS-189532 were included on every 384-well plate. Control wells containing cells without added agonist defined the background signal values. An $EC_{50}$ concentration of agonist in DMSO (180 nM 9-cis-RA for RARα, 8 nM ATRA for RAR β and γ) was added to control and compound wells using the Echo acoustic nanoliter dispenser (Labcyte, San Jose, Calif.). The compound of Example 1 and reference compounds in DMSO (final 0.4%) were added to plates in 8-point dose response in triplicate using the Echo. Cell suspension (30 μL) was added to each well and the assay plate was incubated overnight in a 5% $CO_2$ incubator at 37° C. Luciferase detection reagent (15 μL) was then added and the plate was incubated at RT for 30 minutes. Luminescence was quantified using an EnSpire plate reader (PerkinElmer, Waltham, Mass.). $IC_{50}$ values were determined by fitting dose response data using the four-parameter logistic equation in GraphPad Prism 7.0. The resulting data is shown below.

$IC_{50}$RARα=6.8 nM $IC_{50}$RARβ=>3700 nM $IC_{50}$RARγ=>3700 nM

Example 14. Distribution Assay

30 CD-1 Mice were dosed orally with 10 mg/kg of the compound of Example 1. At specified time points (5, 15, 30 min and 1, 2 4, 8, 16, 24, 48 h) sets of 3 animals were bled and euthanized. Testes and brain were then harvested. Resulting plasma and tissue were frozen at <−20° C. until analysis by LC/MS/MS. Peak levels in the plasma is about 2.1 μM at 15 minutes post-dose, plateaus between 30 minutes and 8 hours at about 1.5 μM and still remains detectable at 48 hours (12.9 nM). The resulting data is shown in FIG. 1.

Example 15. Effects on Male Fertility

Figure 2:
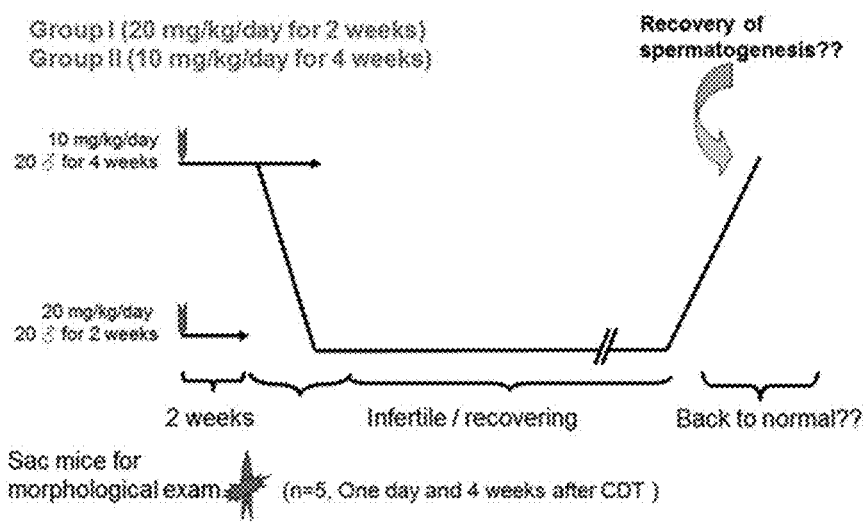
FIG. 2 shows an experimental scheme for testing the effect of the compound of Example 1 on male fertility (identified as GPHR-00354529) from Example 14.

Studies were performed on male mice to determine the effect of the compound of Example 1 on male fertility. Mice were administered 10 mg/kg daily for four weeks or 20 mg/kg daily for two weeks resulting in infertility (FIG. 2). Following cessation of administration of the compound fertility was restored.

Example 16. Mating Studies with Embryo Counts

Figure 3:
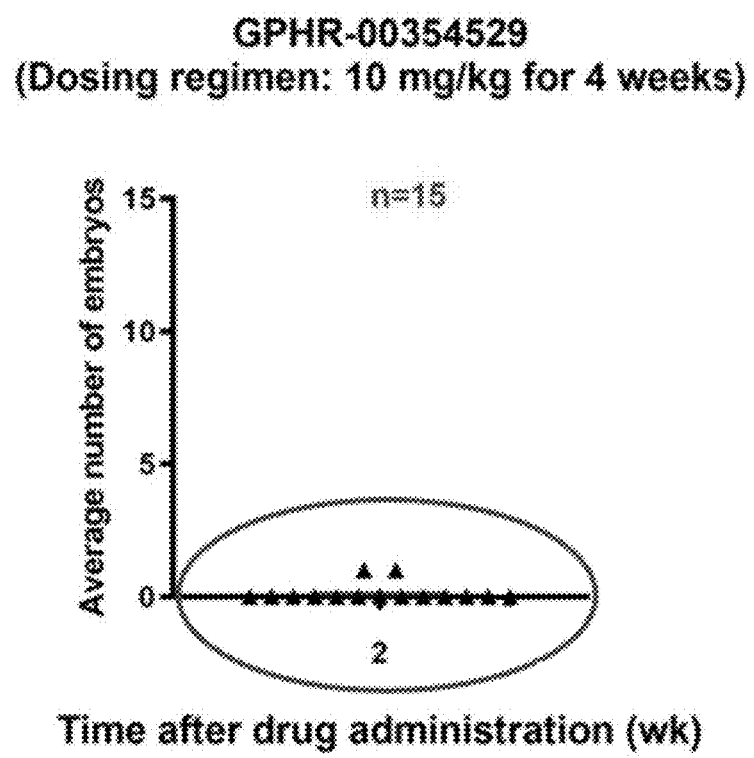
FIG. 3 shows that the administration of the compound of Example 1 (identified as GPHR-00354529) to male mice at 10 mg/kg for four weeks results in infertility two weeks post administration from Example 16.
Figure 4:
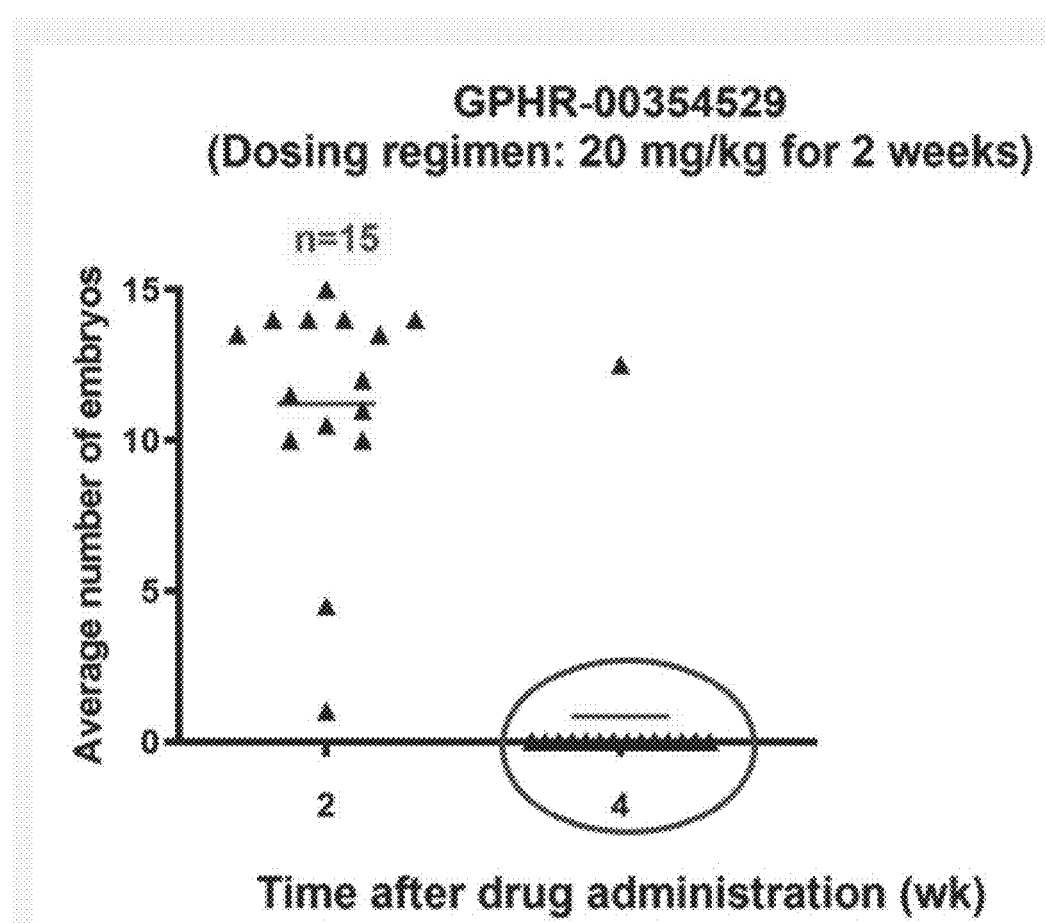
FIG. 4 shows that the administration of the compound of Example 1 (identified as GPHR-00354529) to male mice at 20 mg/kg for two weeks results in infertility four weeks post administration from Example 16.
Figure 5:
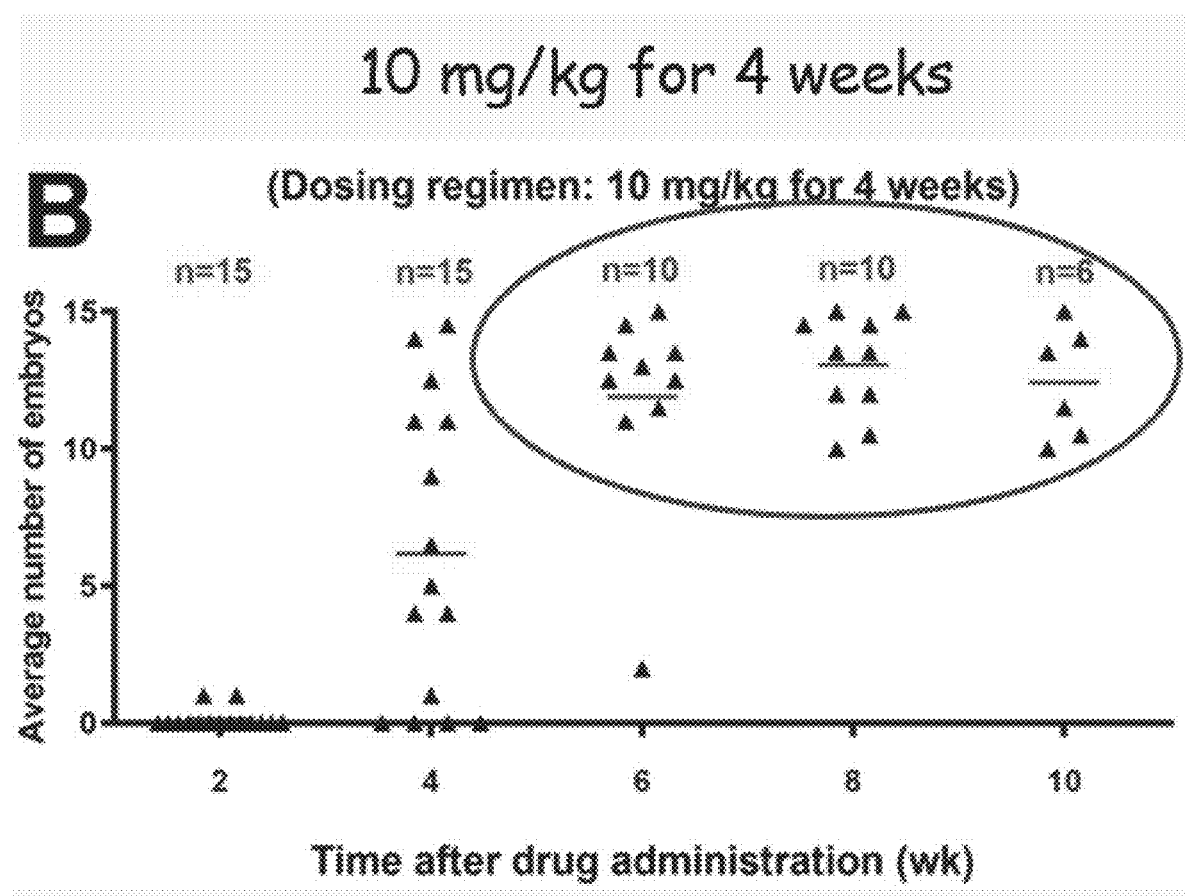
FIG. 5 shows that the administration of the compound of Example 1 (identified as GPHR-00354529) to male mice at 10 mg/kg for four weeks results in infertility and that fertility is recovered four to six weeks post administration from Example 16.
Figure 6:
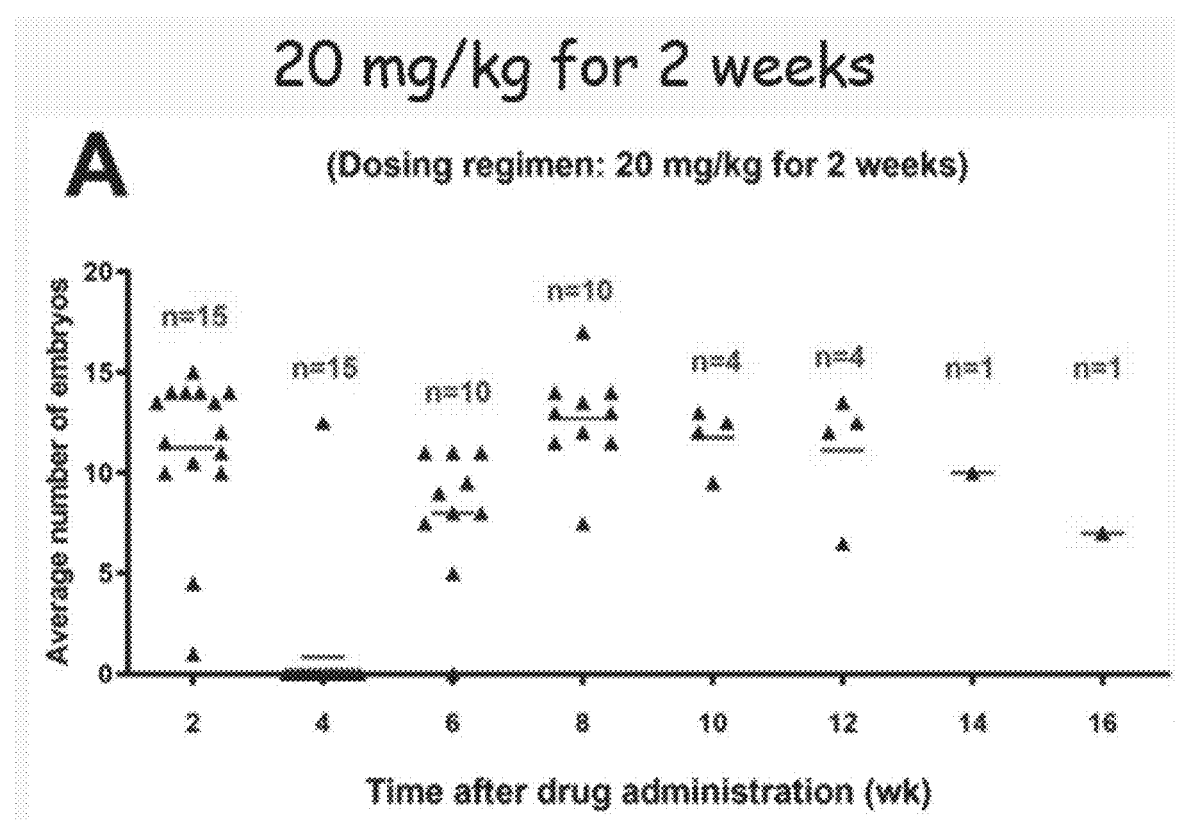
FIG. 6 shows that administration of the compound of Example 1 (identified as GPHR-00354529) to male mice at 20 mg/kg for two weeks resulted in infertility and that fertility is recovered six weeks post administration from Example 16.

Mating Studies with Embryo Counts were conducted as described by, Chung, S. S.; Wang, X.; Roberts, S. S.; Griffey, S. M.; Reczek, P. R.; Wolgemuth, D. J. Oral administration of a retinoic Acid receptor antagonist reversibly inhibits spermatogenesis in mice. *Endocrinology* 2011, 152, 2492-2502. The data show that administration of the compound of Example 1 to male mice at a dose of 10 mg/kg daily for four weeks or 20 mg/kg daily for two weeks results in the induction of infertility (FIGS. 3 and 4). These experiments also demonstrated that the induction of infertility was reversible. FIG. 5 shows that infertility induced in male mice administered the compound of Example 1 at 10 mg/kg/day for four weeks was reversed four to six weeks following cessation of administration of the compound. FIG. 6 shows that infertility induced in male mice administered the compound of Example 1 at 20 mg/kg/day for two weeks was reversed six weeks following cessation of administration of the compound.

Example 17. Representative Pharmaceutical Dosage Forms

The following illustrate representative pharmaceutical dosage forms, containing a compound of formula (I) ('Compound X'), for therapeutic or prophylactic use in humans.

| (i) Tablet 1 | mg/tablet |
| --- | --- |
| Compound X = | 100.0 |
| Lactose | 77.5 |
| Povidone | 15.0 |
| Croscarmellose sodium | 12.0 |
| Microcrystalline cellulose | 92.5 |
| Magnesium stearate | 3.0 |
| | 300.0 |

| (ii) Tablet 2 | mg/tablet |
| --- | --- |
| Compound X = | 20.0 |
| Microcrystalline cellulose | 410.0 |
| Starch | 50.0 |
| Sodium starch glycolate | 15.0 |
| Magnesium stearate | 5.0 |
| | 500.0 |

| (iii) Capsule | mg/capsule |
| --- | --- |
| Compound X = | 10.0 |
| Colloidal silicon dioxide | 1.5 |
| Lactose | 465.5 |
| Pregelatinized starch | 120.0 |
| Magnesium stearate | 3.0 |
| | 600.0 |

| (v) Injection 2 (10 mg/ml) | mg/ml |
| --- | --- |
| Compound X = (free acid form) | 10.0 |
| Monobasic sodium phosphate | 0.3 |
| Dibasic sodium phosphate | 1.1 |
| Polyethylene glycol 400 | 200.0 |
| 1.0N Sodium hydroxide solution (pH adjustment to 7.0-7.5) | q.s. |
| Water for injection | q.s. ad 1 mL |

| (iv) Injection 1 (1 mg/ml) | mg/ml |
|---|---|
| Compound X = (free acid form) | 1.0 |
| Dibasic sodium phosphate | 12.0 |
| Monobasic sodium phosphate | 0.7 |
| Sodium chloride | 4.5 |
| 1.0N Sodium hydroxide solution (pH adjustment to 7.0-7.5) | q.s. |
| Water for injection | q.s. ad 1 mL |

| (vi) Aerosol | mg/can |
|---|---|
| Compound X = | 20.0 |
| Oleic acid | 10.0 |
| Trichloromonofluoromethane | 5,000.0 |
| Dichlorodifluoromethane | 10,000.0 |
| Dichlorotetrafluoroethane | 5,000.0 |

The above formulations may be obtained by conventional procedures well known in the pharmaceutical art.

Example 18. Safety Profile

Introduction and Objectives: Men are lacking contraceptive options that meet their needs and lifestyles. The compound of Example 1 acts as a retinoic acid receptor (RAR)-alpha antagonist thus inhibiting both spermatogenesis and spermiogenesis. The compound of Example 1 has demonstrated a 99% contraceptive efficacy and full reversibility in mice at 10 mg/kg, and sufficient reduction of sperm counts at 7.5 mg/kg.

Methods: The safety profile of the compound of Example 1 was assessed in vitro with target selectivity (cell-based luciferase assays), off-target screening (e.g., patch clamp and cAMP assays), and genotoxicity (Ames test) studies. Acute toxicity in animals was studied with single dose experiments in mice, rats, and dogs. Dose range finding (DRF) studies in rats and dogs were performed to evaluate sub chronic toxicity over a 14-Day dosing period.

Results: The compound of Example 1 is highly selective for RAR-alpha (the respective $IC_{50}$ of the compound of Example 1 was 6.7 nM against RAR-alpha and >3,700 nM against RAR-beta and RAR-gamma), is not considered a hERG inhibitor (the $IC_{50}$ was >30 PM) and has no genotoxic potential (negative Ames test). Single dose studies showed that the respective maximum tolerated dose in mice, rats and dogs was >1,000 mg/kg, 750 mg/kg and >500 mg/kg. Repeated dosing for 14 days demonstrated that rats and dogs tolerated 50-75 mg/kg and 25 mg/kg, respectively. Using simple dose conversion, these values represent 13-20× and 22× multiples over mouse efficacy (7.5 mg/kg).

Conclusions: The compound of Example 1 has demonstrated potent and reversible efficacy in mice and an initial safety profile with an at least 10× safety margin in rats and dogs.

Example 19. In Vivo Studies of Reversing Infertility

Figure 7:
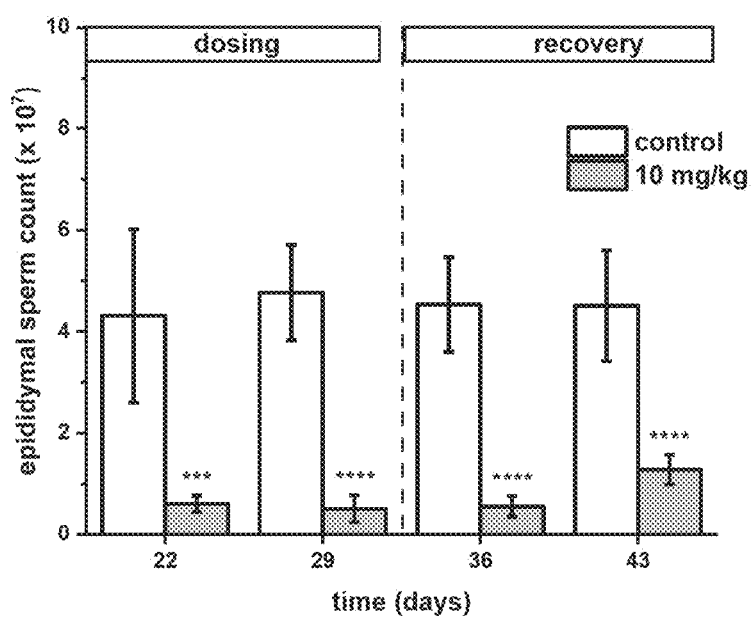
FIG. 7 shows that 10 mg/kg of the compound of Example 1 reversibly reduces sperm counts in mice. 25 male CD-1 mice were dosed with 10 mg/kg/day (grey bars) for 4 weeks. Epididymal sperm counts were assessed once per week as of week 3 and compared to control (white bars). Shown are means±SD of absolute sperm counts from 5 mice per time point. *$p<0.001$, **$p<0.0001$. See Example 19.
Figure 8:
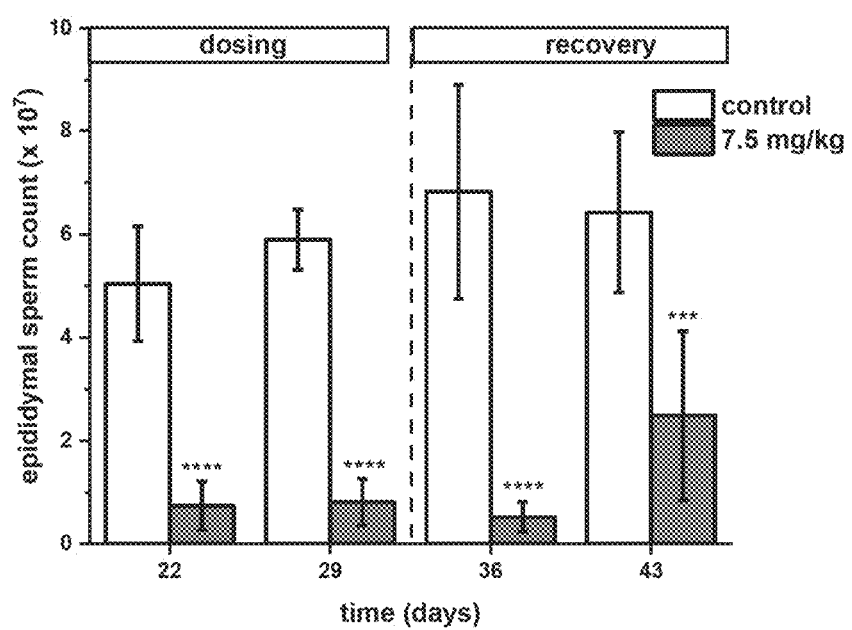
FIG. 8 shows that 7.5 mg/kg of the compound of Example 1 reversibly reduces sperm counts in mice. 40 male CD-1 mice were dosed with 7.5 mg/kg/day (greybars) for 4 weeks. Epididymal sperm counts were assessed once per week as of week 3 and compared to control (white bars). Shown are means±SD of absolute sperm counts from 10 mice per time point. *$p<0.001$, **$p<0.0001$. See Example 19.
Figure 9:
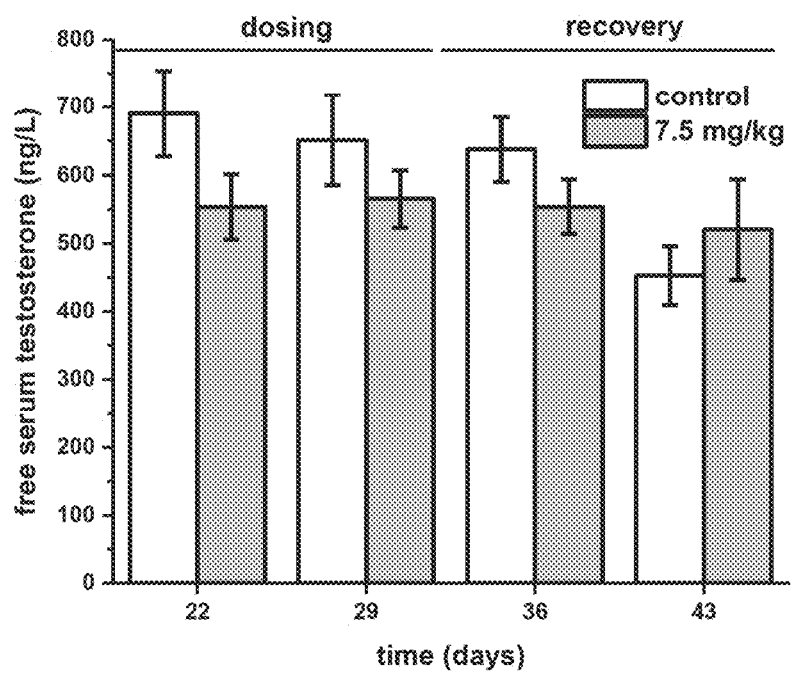
FIG. 9 shows that the compound of Example 1 does not change free serum testosterone levels in mice. 40 male CD-1 mice were dosed with 7.5 mg/kg/day (grey bars) for 4 weeks. Free serum testosterone levels were assessed with ELISA once per week as of week 3 and compared to control (white bars). Shown are means±SD from 10 mice per time point. See Example 19.

Mouse studies with sperm count as readout: In an initial study, 25 sexually mature male CD-1 mice were dosed with 10 mg/kg/day for 4 weeks that resulted in a 90% reduction of epididymal sperm counts to $0.51\pm0.27\times10^7$ as assessed 24 h after administering the last dose. Dosing was stopped on Day 29. Sperm counts started to increase over the remaining 2 weeks supporting reversibility of the effect (FIG. 7). Study 2: Subsequent efficacy studies with 7.5 mg/kg of the compound of Example 1 were performed to determine the minimum efficacious dose in mice. Dosing 40 sexually mature male CD-1 mice with 7.5 mg/kg/day for 4 weeks resulted in an 86% reduction of epididymal sperm counts to $0.82\pm0.45\times10^7$ as assessed 24 h after administering the last dose. Dosing was stopped on Day 29. Sperm counts started to increase over the remaining 2 weeks supporting reversibility of the effect (FIG. 8). Free serum testosterone levels were also determined in the animals dosed at 7.5 mg/kg/day. Free testosterone levels did not significantly change during the dosing and recovery period in dosed animals compared to control animals (FIG. 9).

Figure 10:
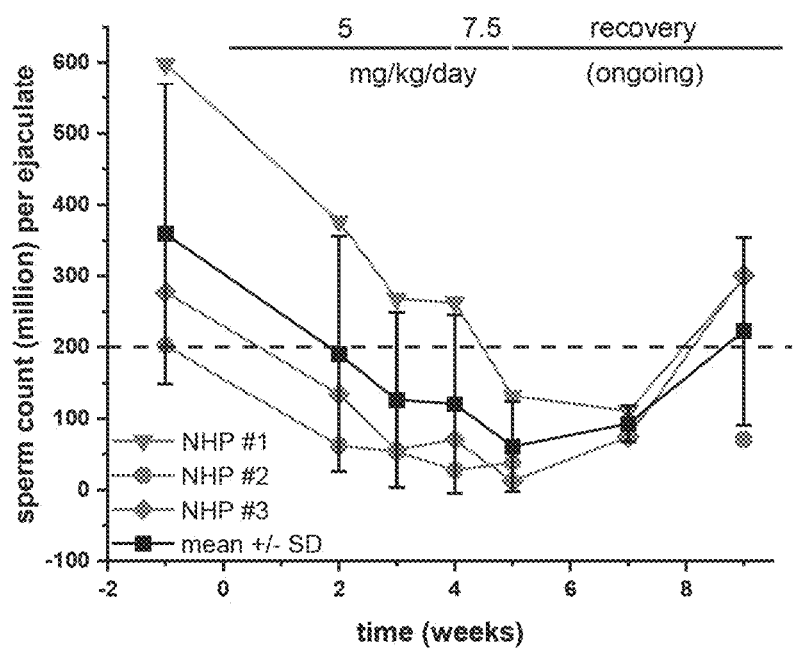
FIG. 10 Three male cynomolgus macaques were dosed at 5 mg/kg/day for 30 days followed by 7.5 mg/kg/day for 1 week with the compound of Example 1. As of Day 38, the animals have been in recovery (ongoing). Sperm counts were assessed from fresh semen samples collected with electro-ejaculation at the indicated time points. Shown are sperm counts of each animal (dark grey lines with triangle, circle and diamond symbols) and means±SD (black line with square symbol). The horizontal dashed line indicates reported sperm counts of non-breeders. See Example 19.

Cynomolgus macaque study with sperm concentration as readout: The design of the study is to daily dose sexually mature male cynomolgus macaques with the compound of Example 1 until sperm counts per ejaculate drop to below 200 million sperm cells per ejaculate. Cynomolgus macaques with $130\pm70$ million sperm per ejaculate are considered poor candidates for breeding programs compared to $734\pm136$ million sperm per ejaculate reported from successful breeders. Sperm counts were assessed weekly or bi-weekly in fresh semen samples obtained with electro-ejaculation. 3 macaques were orally dosed with 2.5 mg/kg, which is the dose equivalent to 10 mg/kg in mouse based on body surface area. Over a dosing period of 54 days, individual sperm counts decreased to 27, 175 and $31\times10^6$. The animals are now in recovery to assess reversibility (data not shown). A second cohort of 3 male cynomolgus macaques was dosed with 5 mg/kg/day of the compound of Example 1 for 30 days followed by 7.5 mg/kg/day for 1 week. Initial individual sperm counts of 598, 203 and $277\times10^6$ decreased to 377, 62 and $134\times10^6$ after 14 days, and to 262, 28 and $70\times10^6$ after 30 days of dosing with 5 mg/kg/day showing efficacy in animal #1 and animal #3 (FIG. 10). After dosing for another week at 7.5 mg/kg/day, individual sperm counts were 132, 38 and $12\times10^6$ showing efficacy in all 3 animals. Since day 38, the animals have been in recovery to assess reversibility. Four weeks after the animals received the last dose, individual sperm counts were 297, 71 and $300\times10^6$ showing 50% reversibility in animal #1, 65% reversibility in animal #2 and 100% reversibility in animal #3.

Figure 11:
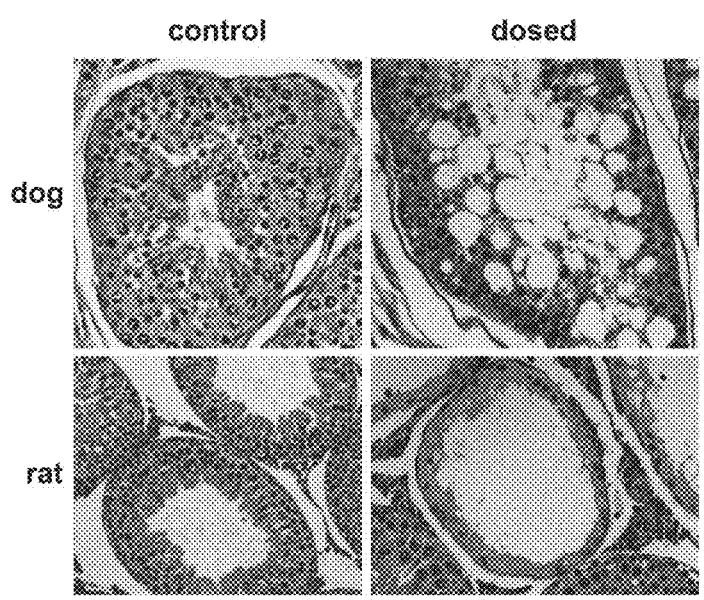
FIG. 11 shows that the compound of Example 1 impairs the germinal epithelium in dog and rat testis. 2 male Beagle dogs and 5 male SD rats were dosed with 25 mg/kg/day for 14 days. On Day 15, animals were euthanized to harvest organs for histopathology. Shown are representative images. See Example 19.

Rat and dog studies: In male Sprague-Dawley rats and male Beagle dogs that received various daily doses of the compound of Example 1 for 14 days in a repeat dose toxicity study (see Example 22), histopathology showed the degeneration of the germinal epithelium in the testis. The effect was visible in all evaluated tubuli seminiferi contorti of dog testis slides and in a subset of evaluated tubuli seminiferi contorti of rat testis slides (FIG. 11).

Example 20. Pharmacokinetics (PK) Studies

Single dose pharmacokinetics (PK) studies at therapeutic dose levels: Presented are area under the curve (AUC) values to better compare exposure levels between species.

Mouse study: 15 sexually mature male CD-1 mice received a single 10 mg/kg dose of the compound of Example 1, which demonstrated contraceptive efficacy in an initial study. AUC from time point 0 extrapolated to infinite time ($AUC_{0-inf}$) in plasma was 6,681 h*(ng/mL). This value serves as the basis to calculate multiples over efficacy across species.

NHP studies: Three young adult male marmosets received a single 5 mg/kg dose of the compound of Example 1 and the compound of 3 sexually mature male cynomolgus macaques received a single dose of 0.5, 1, 5 and 10 mg/kg. Table 1 shows respective plasma $AUC_{0-last}$ levels and multiples over mouse exposure.

TABLE 1

AUC$_{0\text{-}inf}$ levels and multiples over mouse exposure in marmosets and cynomolgus macaques (cyno).

| | Mouse 10 mg/kg | Marmoset 5 mg/kg | Cyno 0.5 mg/kg | Cyno 1 mg/kg | Cyno 5 mg/kg | Cyno 10 mg/kg |
|---|---|---|---|---|---|---|
| Mouse equivalent dose | — | 10 mg/kg | 2 mg/kg | 4 mg/kg | 20 mg/kg | 40 mg/kg |
| AUC$_{0\text{-}inf}$ (h*ng*mL$^{-1}$) | 6,681 | 6,920 | 23,382 | 33,394 | 175,202 | 293,423 |
| Multiple over mouse exposure | — | 1X | 3.5X | 5X | 26X | 44X |

Repeat Dose PK Studies at Supratherapeutic Dose Levels:

Rat study: Male Sprague-Dawley rats (7-9 weeks old) received 0, 25, 50 and 125 mg/kg/day of the compound of Example 1 (3 rats per group) for 14 days. Since 125 mg/kg/day was not tolerated well, the dose was reduced to 75 mg/kg on Day 7. In this study, the AUC from time point 0 to the time of the last measured concentration (48 h) was measured (AUC$_{0\text{-}48}$). Table 2 shows plasma AUC$_{0\text{-}48}$ levels on Day 14 and multiples over mouse exposure.

TABLE 2

AUC$_{0\text{-}48}$ levels on Day 14 and multiples over mouse exposure in rats after a 14-day dosing period.

| | Mouse 10 mg/kg | Rat 25 mg/kg | Rat 50 mg/kg | Rat 125/75 mg/kg |
|---|---|---|---|---|
| Mouse equivalent dose | — | 50 mg/kg | 100 mg/kg | 250/150 mg/kg |
| AUC$_{0\text{-}48}$ (h*ng*mL$^{-1}$) | 6,577 | 78,778 | 91,122 | 202,091 |
| Multiple over mouse exposure | — | 12X | 14X | 31X* |

*This is related to 75 mg/kg.

Dog study Two male Beagle dogs (8-12 months old) received 0, 25 and 100 mg/kg/day of the compound of Example 1 for 14 days. In this study, AUC$_{0\text{-}inf}$ was measured. Table 3 shows plasma AUC$_{0\text{-}last}$ levels on Day 14 and multiples over mouse exposure

TABLE 3

AUC$_{0\text{-}inf}$ levels on Day 14 and multiples over mouse exposure in dogs after a 14-day dosing period.

| | Mouse 10 mg/kg | Dog 25 mg/kg | Dog 100 mg/kg |
|---|---|---|---|
| Mouse equivalent dose | — | 167 mg/kg | 667 mg/kg |
| AUC$_{0\text{-}inf}$ (h*ng*mL$^{-1}$) | 6,681 | 751,730 | 14,128,277 |
| Multiple over mouse exposure | — | 113X | 2,115X |

Example 21. In Vitro Studies

The following Table 4 summarizes in vitro study results for the compound of Example 1.

TABLE 4

| | The compound of Example 1 in vitro studies |
|---|---|
| Solubility | Up to 100 mg/mL in saline and >100 mg/mL in 50% carbitol [2-(2-ethoxyethoxy)ethanol |
| LogD | 3.5 |
| Target selectivity: | The respective half-maximal inhibitory concentration (IC$_{50}$) of the compound of Example 1 was 6.7 nM against retinoic acid receptor (RAR)-alpha and >3,700 nM against RAR-beta and RAR-gamma. |
| hERG: | The compound of Example 1 is not considered an hERG inhibitor. The IC$_{50}$ in hERG-transfected HEK293 cells was >30 µM. |
| Antagonist activity against ion channels, transporters, enzymes and nuclear receptors: | Agonist and antagonist activity of the compound of Example 1 was tested against 48 potential off-targets including 6 ion channels, 17 non-nuclear receptors, 2 transporters, 11 enzymes, and 2 nuclear receptors. At 10 µM the compound of Example 1 had agonist or antagonist activity of <10% against 39 of them (including glucocorticoid and androgen receptors). The following 10 targets were inhibited by at least 10% with 10 µM of the compound of Example 1: 1) acetylcholinesterase (AChE) by 10.2%, 2) Kir2.1 (potassium channel of excitable cells) by 13.2%, 3) KVLQT(7.1)/mink (cardiac potassium ion channel) by 14.9%, 4) KCNQ1 (neuronal potassium ion channel) by 22.8%, 5) cannabinoid receptor 2 (CB2) by 34.3%, 6) NaV1.5 (cardiac sodium ion channel) by 37.4%, 7) monoamine oxidase A (MAO-A) by 45.8%, 8) cyclooxygenase 2 (COX2) by 61.8%, 9) cyclooxygenase 1 (COX1) by 78.9% and 10) cannabinoid receptor 1 (CB1) by 90.5%. The respective IC$_{50}$ values were: 1.41 µM (COX1), 1.8 µM (CB1), 8.51 µM (COX2), 8.8 µM (NaV1.5), >10 µM (Kir2.1), 23.3 µM (CB2), 24.6 µM (MAO-A), and >30 µM (AChE). The IC$_{50}$ against KCNQ1 was not determined. |
| Ames test: | The results showed no indication that the compound of Example 1 has genotoxic potential. |

TABLE 4-continued

| The compound of Example 1 in vitro studies | | | |
|---|---|---|---|
| The stability of the compound of Example 1 was assessed in mammalian hepatocytes and liver microsomes. Shown below are the respective half-lives ($T_{1/2}$). | | | |
| | | Hepatocytes (Phase 1 and Phase II metabolism) | Liver microsomes (Phase I metabolism) |
| Stability in hepatocytes and liver microsomes: | human | 8.7 h | 9.5 h |
| | monkey | 3.2 h | 23.1 h |
| | mouse | 4.8 h | >23.1 h |
| | rat | 7.9 h | >23.1 h |
| | rabbit | not tested | 19.6 h |
| | dog | >10 h | >23.1 h |
| MetID | Under the experimental conditions, very little metabolism of the compound of Example 1 occurred in hepatocytes of various mammalian species (human, monkey, mouse, rat, dog, and rabbit) and neither of the ten metabolites was detected at greater than 10% of total metabolites. | | |
| Cytotoxicity: | The compound of Example 1 showed no cytopathic effects in HepG2 and human lung fibroblast assays. | | |

Example 22. Toxicity Studies

Single Dose Toxicity:

The respective maximum tolerated dose (MTD) of the compound of Example 1 in male CD-1 mice, Sprague-Dawley rats and Beagle dogs was ≥1,000 mg/kg, ≥750 mg/kg and ≥500 mg/kg. These were the respective highest dose levels tested.

Repeat Dose Toxicity at Therapeutic Levels:

Mouse: 40 sexually mature male CD-1 mice received 7.5 and 10 mg/kg/day of the compound of Example 1, respectively, for 4 weeks. All dosed animals behaved normally, had no changes in body weight, CBC parameters or clinical chemistry parameters compared to control animals.

Non-human primate: All 6 male cynomolgus macaques of the efficacy studies behaved normally and had no substantial changes in body weight, CBC parameters or clinical chemistry parameters.

Repeated Dose Toxicity at Supratherapeutic Levels 14-day dose range finding (DRF) study with rats: Male Sprague-Dawley rats (7-9 weeks old) received 0, 25, 50, 125 and 250 mg/kg/day of the compound of Example 1 (5 rats per group) via oral gavage. 25 and 50 mg/kg were tolerated well. Initial dosing with 125 mg/kg was not tolerated well so that the dose was reduced to 75 mg/kg for the remaining 8 days. Over that period the animals' overall health and activity improved, they gained weight, and had normal CBC and clinical chemistry. 250 mg/kg/day was not tolerated. These results show that the maximum tolerated dose over a 2-week dosing period was 50 mg/kg. 14-day DRF study with dogs: Male Beagle dogs (8-12 months old) received 0, 25, 50 and 100 mg/kg/day of the compound of Example 1 (2 dogs per group) via oral gavage. 25 mg/kg were tolerated well and both animals behaved normally and did not show signs of toxicity. 50 mg/kg was not tolerated. In the 100 mg/kg group one dog did not show any signs of toxicity. The other dog lost weight as of Day 12 until termination. Based on these results, the maximum tolerated dose over a 2-week dosing period was 25 mg/kg.

Example 23. Synthesis of 4-(5-(4-(4-fluorophenyl)-2,2-dimethyl-2H-chromen-6-yl)-1H-pyrrol-2-yl)benzoic Acid

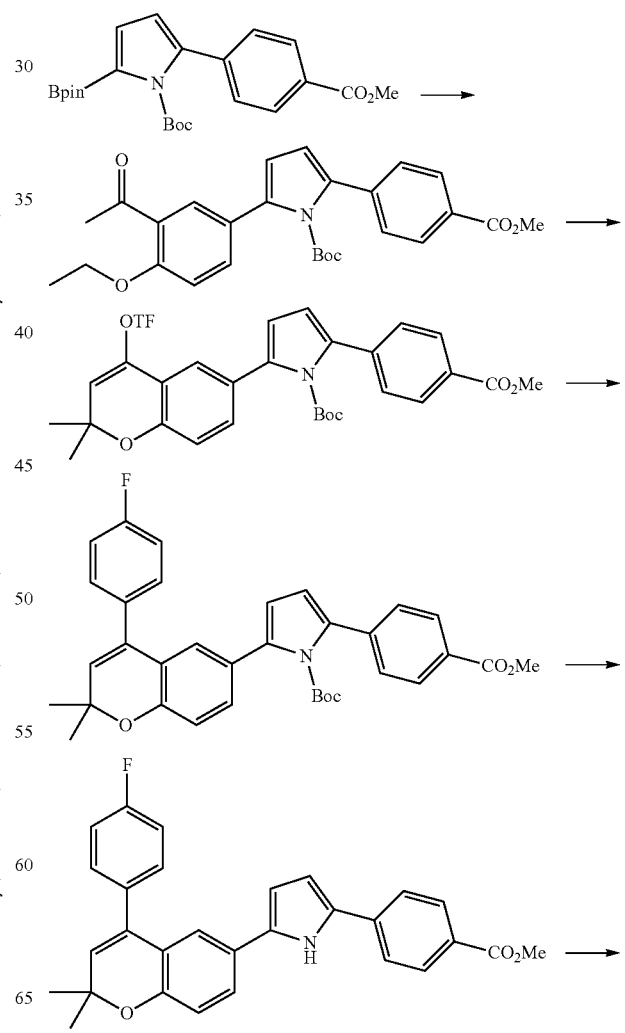

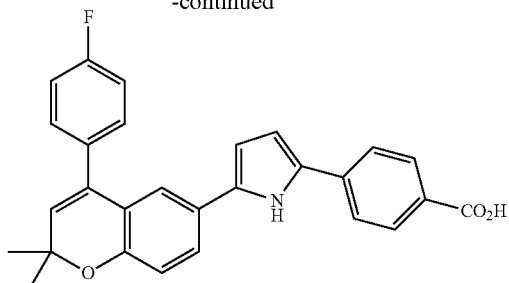

a. Preparation of tert-butyl 2-(4-(methoxycarbonyl)phenyl)-5-(4,4,5,5-tetramethyl-1,3,2-dioxaborolan-2-yl)-1H-pyrrole-1-carboxylate

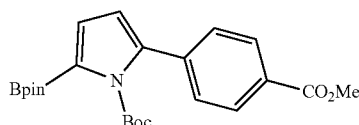

Under a nitrogen atmosphere, (Boc)₂O (20.0 mL, 1 M in DCM, 2.1 equiv) was added to a solution of methyl 4-(4,4,5,5-tetramethyl-1,3,2-dioxaborolan-2-yl)-1H-pyrrole-2-yl)benzoate (3.20 g, 9.72 mmol, 1.0 equiv) and DMAP (60 mg, 0.49 mmol, 0.05 equiv) in dry MeCN (5 mL) at room temperature. The mixture was stirred until the starting material disappeared completely. After water was added, the resulting mixture was extracted with DCM (20 mL×3). The organic phase was washed with brine, dried over Na₂SO₄, and evaporated under reduced pressure. The residue was purified by flash column chromatography (SiO₂, 100% hexanes to 10% EtOAc in hexanes) to give the product (2.34 g, 56%) as a colorless oil. ¹H NMR (400 MHz, CDCl₃) δ 8.04-7.97 (m, 2H), 7.40-7.34 (m, 2H), 6.64 (d, J=3.3 Hz, 1H), 6.25 (d, J=3.3 Hz, 1H), 3.92 (s, 3H), 1.35 (s, 12H), 1.32 (s, 9H).

b. Preparation of tert-butyl 2-(2,2-dimethyl-4-oxochroman-6-yl)-5-(4-(methoxy-carbonyl)phenyl)-1H-pyrrole-1-carboxylate

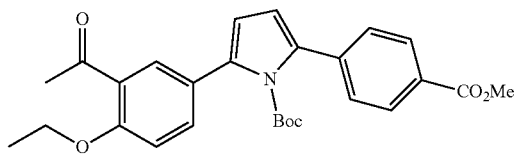 [SMILES: CCOc1ccc(-c2ccc(-c3ccc(C(=O)OC)cc3)n2C(=O)OC(C)(C)C)cc1C(C)=O]

6-Bromo-2,2-dimethylchroman-4-one (550 g, 2.16 mmol, 1.1 equiv), tert-butyl 2-(4-(methoxycarbonyl)phenyl)-5-(4,4,5,5-tetramethyl-1,3,2-dioxaborolan-2-yl)-1H-pyrrole-1-carboxylate (822 mg, 1.92 mmol, 1.0 equiv), K₂CO₃ (830 mg, 6.01 mmol, 3.1 equiv) were taken into a round-bottom flask followed by addition of DME (15 mL) and H₂O (2 mL). Then N₂ was bubbled through the reaction mixture for 10 min followed by addition of Pd(dppf)Cl₂·CH₂Cl₂ (160 mg, 0.196 mmol, 0.1 equiv). Then the vial was sealed and placed in a preheated oil bath at 90° C. and refluxed for 6 h. After the reaction was complete, brine was added to the reaction mixture and extracted with EtOAc (20 mL×3), dried over MgSO₄. The solvent was evaporated to dryness. The residue was purified by flash column chromatography (SiO₂, 100% hexanes to 20% EtOAc in hexanes) to obtain the product as a white solid (600 mg, 66%). ¹H NMR (400 MHz, CDCl₃) δ 8.08-8.01 (m, 2H), 7.88 (d, J=2.3 Hz, 1H), 7.53 (dd, J=8.5, 2.3 Hz, 1H), 7.48-7.41 (m, 2H), 7.03-6.92 (m, 1H), 6.30 (d, J=3.4 Hz, 1H), 6.23 (d, J=3.4 Hz, 1H), 3.93 (s, 3H), 2.74 (s, 2H), 1.48 (s, 6H), 1.19 (s, 9H).

c. Preparation of tert-butyl 2-(2,2-dimethyl-4-(((trifluoromethyl)sulfonyl)oxy)-2H-chromen-6-yl)-5-(4-(methoxycarbonyl)phenyl)-1H-pyrrole-1-carboxylate

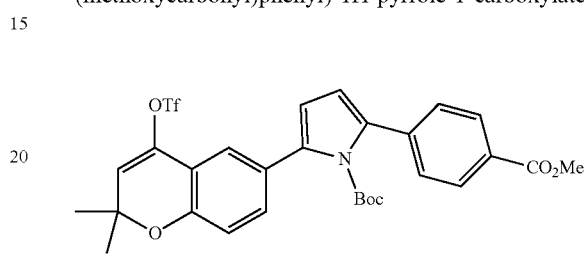

To a stirred solution of tert-butyl 2-(2,2-dimethyl-4-oxochroman-6-yl)-5-(4-(methoxycarbonyl)phenyl)-1H-pyrrole-1-carboxylate (583 mg, 1.23 mmol, 1.0 equiv), 2,6-lutidine (925 mg, 8.63 mmol, 7.0 equiv) and DMAP (41 mg, 0.34 mmol, 0.3 equiv) in anhydrous DCM (10 mL) at 0° C. was added triflic anhydride (1.00 g, 3.54 mmol, 2.9 equiv) dropwise and the reaction mixture was slowly warmed to room temperature with continuous stirring. After stirring overnight at room temperature, the reaction was quenched with saturated sodium bicarbonate solution and extracted with DCM (20 mL×3). The combined organic layers were then washed with brine, dried over MgSO₄, filtered, and concentrated under reduced pressure to yield a crude brown oil. The crude product was purified by flash column chromatography (SiO₂, 100% hexanes to 10% EtOAC in hexanes) to obtain the product (550 mg, 77%) as a colorless liquid. ¹H NMR (400 MHz, CDCl₃) δ 8.09-8.02 (m, 2H), 7.50-7.42 (m, 2H), 7.32-7.23 (m, 2H), 6.86 (d, J=8.9 Hz, 1H), 6.31 (d, J=3.4 Hz, 1H), 6.21 (d, J=3.4 Hz, 1H), 5.66 (s, 1H), 3.93 (s, 3H), 1.55 (s, 6H), 1.19 (s, 9H).

d. Preparation of tert-butyl 2-(4-(4-fluorophenyl)-2,2-dimethyl-2H-chromen-6-yl)-5-(4-(methoxycarbonyl)phenyl)-1H-pyrrole-1-carboxylate

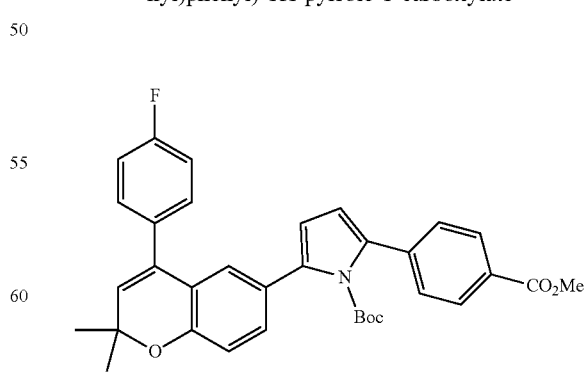

tert-Butyl 2-(2,2-dimethyl-4-(((trifluoromethyl)sulfonyl)oxy)-2H-chromen-6-yl)-5-(4-(methoxycarbonyl)phenyl)-1H-pyrrole-1-carboxylate (200 g, 0.329 mmol, 1 equiv), (4-fluorophenyl)boronic acid (68 mg, 0.49 mmol, 1.5 equiv), $K_3PO_4$ (4.0 mL 0.5 M in $H_2O$, 2.0 mmol, 6.1 equiv) was taken into a round-bottom flask followed by addition of THF (2 mL). Then $N_2$ was bubbled through the reaction mixture for 10 min followed by the addition of XPhos Pd G2 (60 mg, 0.076 mmol, 0.2 equiv). Then the vial was sealed and placed in a preheated block at 45° C. and stirred for 3 h. After the reaction was complete, brine was added to the reaction mixture and extracted with EtOAc (5 mL×3), dried over $MgSO_4$, and the solvent was evaporated under reduced pressure. The residue was purified by flash column chromatography ($SiO_2$, 100% hexanes to 20% EtOAc in hexanes) to obtain the product as a white solid (132 mg, 72%). $^1H$ NMR (400 MHz, $CDCl_3$) δ 8.09-7.99 (m, 2H), 7.45-7.38 (m, 2H), 7.37-7.28 (m, 2H), 7.21 (dd, J=8.3, 2.2 Hz, 1H), 7.13-7.02 (m, 2H), 7.01 (d, J=2.1 Hz, 1H), 6.91 (d, J=8.3 Hz, 1H), 6.27 (d, J=3.4 Hz, 1H), 6.14 (d, J=3.4 Hz, 1H), 5.62 (s, 1H), 3.93 (s, 3H), 1.52 (s, 6H), 1.16 (s, 9H).

e. Preparation of methyl 4-(5-(4-(4-fluorophenyl)-2,2-dimethyl-2H-chromen-6-yl)-1H-pyrrol-2-yl)benzoate

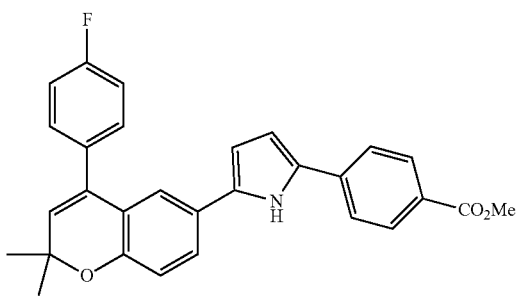 [SMILES: COC(=O)c1ccc(-c2ccc(-c3ccc4c(c3)C(c3ccc(F)cc3)=CC(C)(C)O4)[nH]2)cc1]

tert-Butyl 2-(4-(4-fluorophenyl)-2,2-dimethyl-2H-chromen-6-yl)-5-(4-(methoxycarbonyl)phenyl)-1H-pyrrole-1-carboxylate (100 mg, 0.181 mmol, 1 equiv) was heated to 180° C. under $N_2$ gas for 30 min. The dark residue was purified by flash column chromatography to obtain the product (62 mg, 76%) as a white powder. $^1H$ NMR (400 MHz, $CDCl_3$) δ 8.52 (s, 1H), 8.03 (d, J=8.0 Hz, 2H), 7.52 (d, J=8.1 Hz, 2H), 7.38 (td, J=5.4, 2.3 Hz, 3H), 7.18-7.10 (m, 3H), 6.96 (d, J=8.3 Hz, 1H), 6.67 (t, J=3.2 Hz, 1H), 6.39 (t, J=3.2 Hz, 1H), 5.67 (s, 1H), 3.93 (s, 3H), 1.54 (s, 6H).

f. Preparation of 4-(5-(4-(4-fluorophenyl)-2,2-dimethyl-2H-chromen-6-yl)-1H-pyrrol-2-yl)benzoic Acid

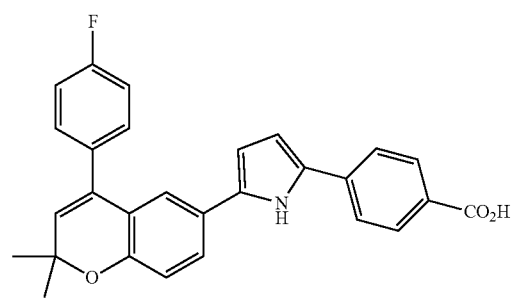 [SMILES: CC1(C)C=C(c2ccc(F)cc2)c2cc(-c3ccc(-c4ccc(C(=O)O)cc4)[nH]3)ccc2O1]

To a solution of methyl 4-(5-(4-(4-fluorophenyl)-2,2-dimethyl-2H-chromen-6-yl)-1H-pyrrol-2-yl)benzoate (50 mg, 0.11 mmol, 1.0 equiv) in THF (1 mL) and MeOH (1 mL), was added LiOH (50 mg, 1.2 mmol, 11 equiv) dissolved in water (1 mL) and the resulting mixture was stirred overnight at room temperature. Then the organic layer was evaporated under reduced pressure and the aqueous suspension was acidified with 2N HCl to reach pH 1.0. Then the reaction mixture was extracted with EtOAc (2 mL×3), washed with brine, and dried over $MgSO_4$. The extract was purified by flash column chromatography ($SiO_2$, 100% hexanes to 50% EtOAc and 2% HCOOH in hexanes) to obtain the product (36 mg, 74%) as a yellow solid. $^1H$ NMR (400 MHz, $THF-d_8$) δ 10.40 (s, 1H), 7.96-7.89 (m, 2H), 7.64-7.57 (m, 2H), 7.50-7.36 (m, 3H), 7.27 (d, J=2.2 Hz, 1H), 7.21-7.12 (m, 2H), 6.86 (d, J=8.4 Hz, 1H), 6.60 (dd, J=3.7, 2.5 Hz, 1H), 6.27 (dd, J=3.7, 2.4 Hz, 1H), 5.72 (s, 1H), 1.46 (s, 6H).

Example 24. Synthesis of Representative Compounds

Using procedures similar to those described above, the following compounds were prepared.

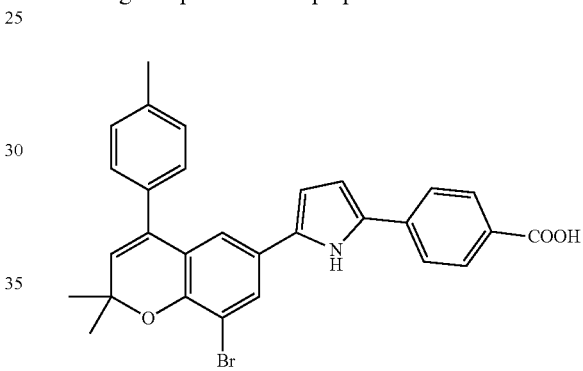

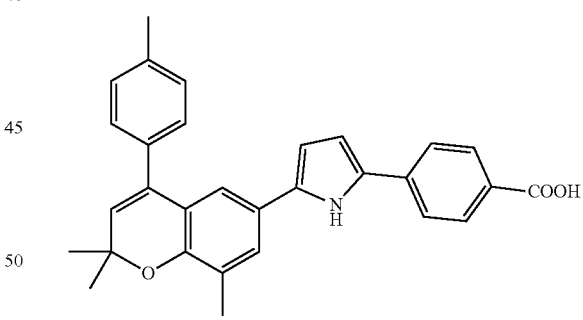

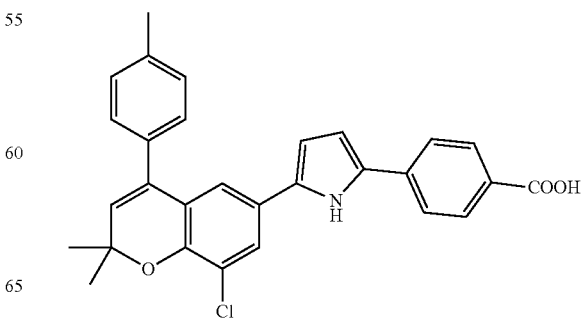

-continued
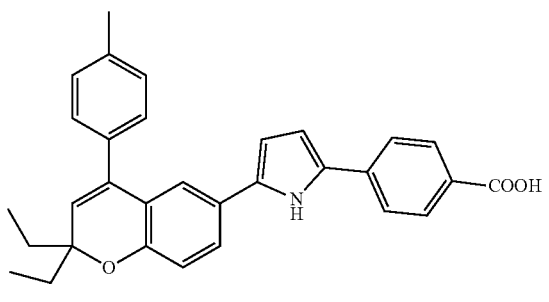 [SMILES: CCC1(CC)C=C(c2ccc(C)cc2)c2cc(-c3ccc(-c4ccc(C(=O)O)cc4)[nH]3)ccc2O1]
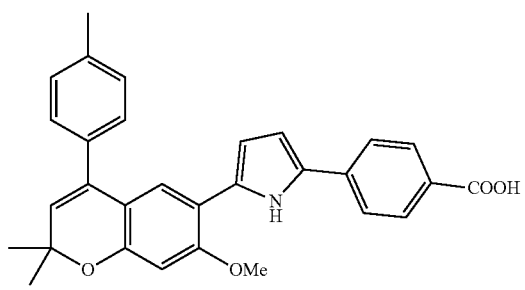 [SMILES: COc1cc2c(cc1-c1ccc(-c3ccc(C(=O)O)cc3)[nH]1)C(c1ccc(C)cc1)=CC(C)(C)O2]
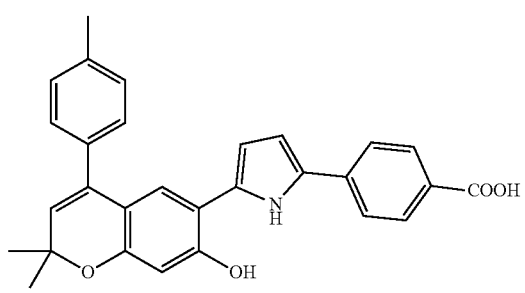 [SMILES: Cc1ccc(C2=CC(C)(C)Oc3cc(O)c(-c4ccc(-c5ccc(C(=O)O)cc5)[nH]4)cc32)cc1]
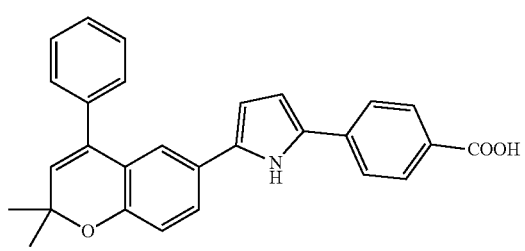 [SMILES: CC1(C)C=C(c2ccccc2)c2cc(-c3ccc(-c4ccc(C(=O)O)cc4)[nH]3)ccc2O1]
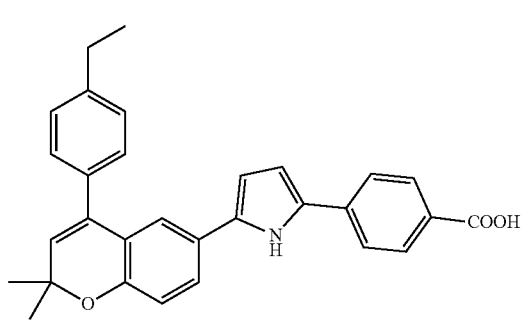 [SMILES: CCc1ccc(C2=CC(C)(C)Oc3ccc(-c4ccc(-c5ccc(C(=O)O)cc5)[nH]4)cc32)cc1]
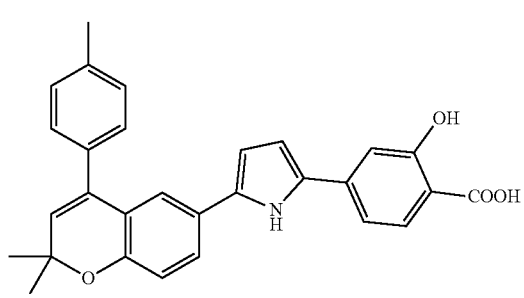 [SMILES: Cc1ccc(C2=CC(C)(C)Oc3ccc(-c4ccc(-c5ccc(C(=O)O)c(O)c5)[nH]4)cc32)cc1]
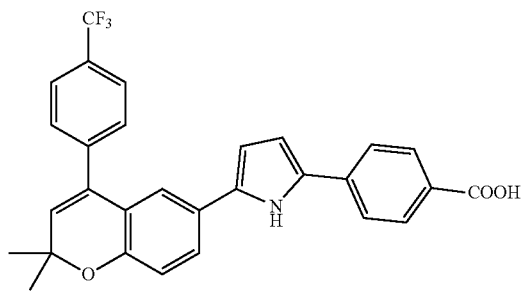 [SMILES: CC1(C)C=C(c2ccc(C(F)(F)F)cc2)c2cc(-c3ccc(-c4ccc(C(=O)O)cc4)[nH]3)ccc2O1]
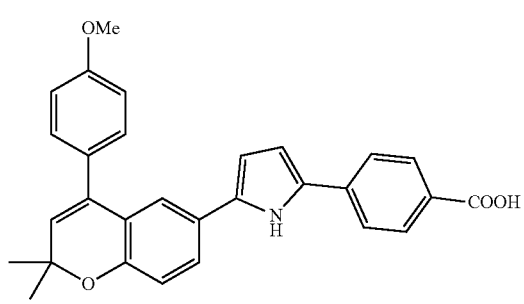
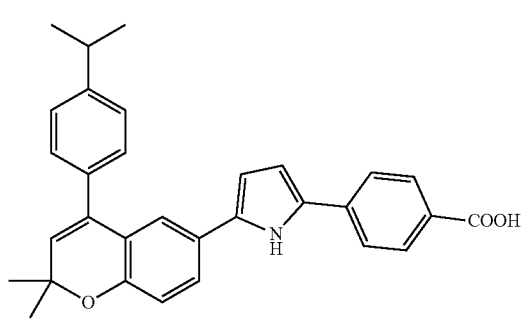 [SMILES: CC(C)c1ccc(C2=CC(C)(C)Oc3ccc(-c4ccc(-c5ccc(C(=O)O)cc5)[nH]4)cc32)cc1]

-continued
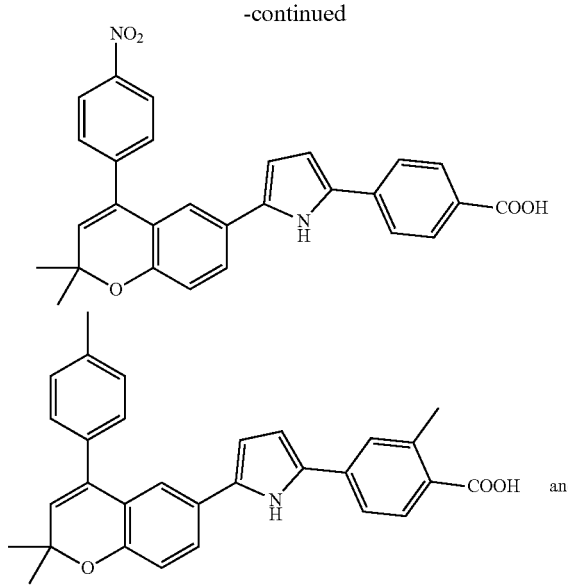
and
-continued
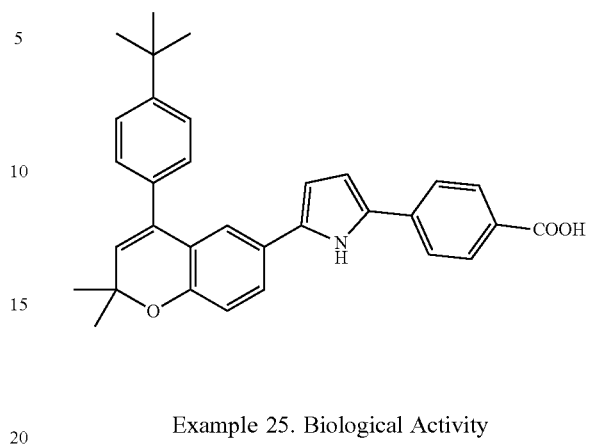
Example 25. Biological Activity
Representative compounds of the invention were evaluated in the assay described in Example 13 to provide the following data.
| Compound | RARα Antagonism IC$_{50}$ (nM) | RARβ Antagonism IC$_{50}$ (nM) | RARγ Antagonism IC$_{50}$ (nM) |
|---|---|---|---|
|  | 6.8 | >3700 | >3700 |
|  | 100 |  |  |
|  | 470 |  |  |

-continued

| Compound | RARα Antagonism IC$_{50}$ (nM) | RARβ Antagonism IC$_{50}$ (nM) | RARγ Antagonism IC$_{50}$ (nM) |
|---|---|---|---|
| (structure with Br) | | | 736 |
| (structure with methyl) | | | 773 |
| (structure with Cl) | | | 943 |
| (structure with diethyl) | | | >3300 |
| (structure with OMe) | | | 2000 |

-continued

| Compound | RARα Antagonism IC$_{50}$ (nM) | RARβ Antagonism IC$_{50}$ (nM) | RARγ Antagonism IC$_{50}$ (nM) |
|---|---|---|---|
| [structure: 4-(p-tolyl)-2,2-dimethyl-7-hydroxy-chromene-6-yl pyrrole-phenyl-COOH] | >3300 | | |
| [structure: 4-phenyl-2,2-dimethyl-chromene-6-yl pyrrole-phenyl-COOH] | 15 | >3300 | >3300 |
| [structure: 4-(4-fluorophenyl)-2,2-dimethyl-chromene-6-yl pyrrole-phenyl-COOH] | 44 | >3000 | >3000 |
| [structure: 4-(4-ethylphenyl)-2,2-dimethyl-chromene-6-yl pyrrole-phenyl-COOH] | 466 | >3000 | >3000 |
| [structure: 4-(p-tolyl)-2,2-dimethyl-chromene-6-yl pyrrole-(3-hydroxy-4-carboxyphenyl)] | 94 | >3000 | >3000 |

-continued

| Compound | RARα Antagonism IC$_{50}$ (nM) | RARβ Antagonism IC$_{50}$ (nM) | RARγ Antagonism IC$_{50}$ (nM) |
|---|---|---|---|
| [structure: 4-CF$_3$-phenyl chromene pyrrole benzoic acid] | 1306 | >3000 | >3000 |
| [structure: 4-OMe-phenyl chromene pyrrole benzoic acid] | 368 | >3000 | >3000 |
| [structure: 4-isopropyl-phenyl chromene pyrrole benzoic acid] | >3300 | >3000 | >3000 |
| [structure: 4-NO$_2$-phenyl chromene pyrrole benzoic acid] | 811 | >3000 | >3000 |
| [structure: 4-methyl-phenyl chromene pyrrole 3-methyl-benzoic acid] | 87 | >3000 | >3000 |

-continued

| Compound | RARα Antagonism IC$_{50}$ (nM) | RARβ Antagonism IC$_{50}$ (nM) | RARγ Antagonism IC$_{50}$ (nM) |
|---|---|---|---|
| 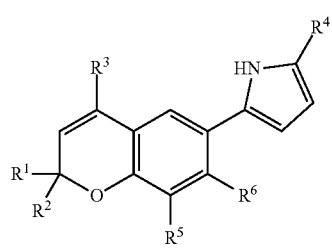 | >3000 | >3000 | >3000 |

All publications, patents, and patent documents are incorporated by reference herein, as though individually incorporated by reference. The invention has been described with reference to various specific and preferred embodiments and techniques. However, it should be understood that many variations and modifications may be made while remaining within the spirit and scope of the invention.

What is claimed is:

1. A compound of formula (I):

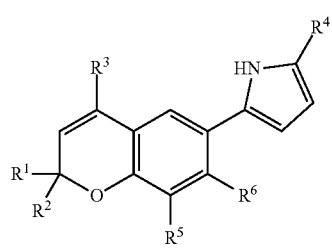

(I)

or a pharmaceutically acceptable salt thereof, wherein:
  $R^1$ is $C_1$-$C_3$alkyl;
  $R^2$ is $C_1$-$C_3$alkyl;
  $R^3$ is phenyl that is optionally substituted with one or more groups independently selected from $C_1$-$C_6$alkyl that is optionally substituted with one or more groups independently selected from halo;
  $R^4$ is phenyl that is substituted with carboxy and that is further optionally substituted with one or more groups independently selected from $C_1$-$C_6$alkyl that is optionally substituted with one or more groups independently selected from halo;
  $R^5$ is H; and
  $R^6$ is H.

2. The compound or pharmaceutically acceptable salt of claim 1, wherein $R^1$ is methyl.

3. The compound or pharmaceutically acceptable salt of claim 1, wherein $R^3$ is phenyl that is substituted with $C_1$-$C_6$alkyl.

4. The compound or pharmaceutically acceptable salt of claim 1, wherein $R^3$ is 4-methylphenyl.

5. The compound or pharmaceutically acceptable salt of claim 1, wherein $R^4$ is phenyl that is substituted with carboxy.

6. The compound or pharmaceutically acceptable salt of claim 1, wherein $R^4$ is 4-carboxyphenyl.

7. The compound or pharmaceutically acceptable salt of claim 1 that is:

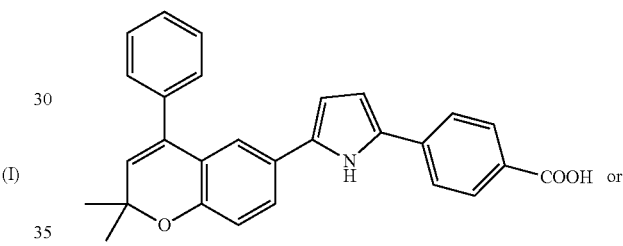

or

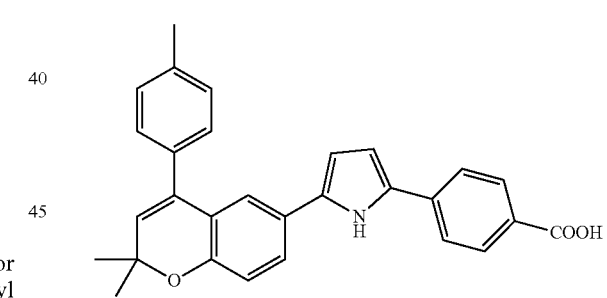

or a pharmaceutically acceptable salt thereof.

8. The compound or pharmaceutically acceptable salt of claim 1, which is a compound of formula (Ia):

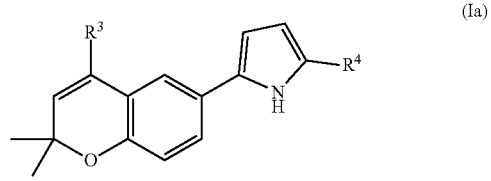

(Ia)

or a pharmaceutically acceptable salt thereof.

9. The compound or pharmaceutically acceptable salt of claim 1, which is a compound of formula (Ib):

(Ib)

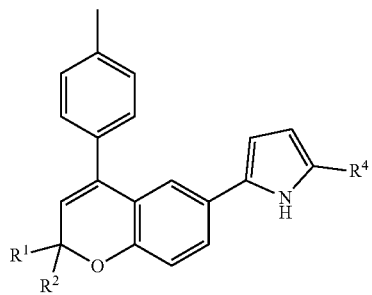

or a pharmaceutically acceptable salt thereof.

10. The compound or pharmaceutically acceptable salt of claim 1, which is a compound of formula (Ic):

(Ic)

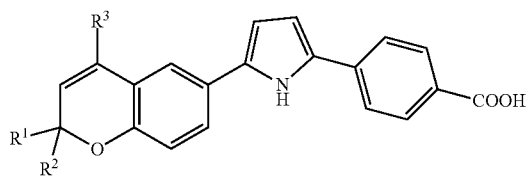

or a pharmaceutically acceptable salt thereof.

11. The compound or pharmaceutically acceptable salt of claim 1, which is a compound of formula (Id):

(Id)

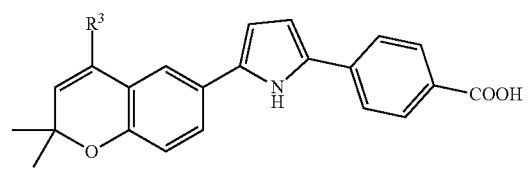

or a pharmaceutically acceptable salt thereof.

12. A compound or pharmaceutically acceptable salt that is selected from the group consisting of:

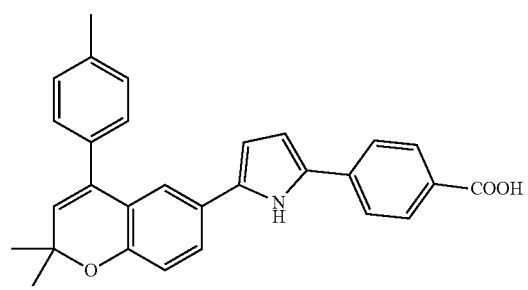 [SMILES: Cc1ccc(C2=CC(C)(C)Oc3ccc(-c4ccc(-c5ccc(C(=O)O)cc5)[nH]4)cc32)cc1]

-continued

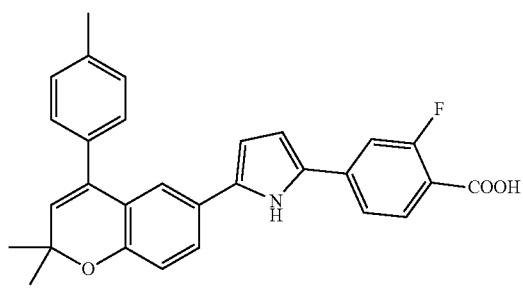

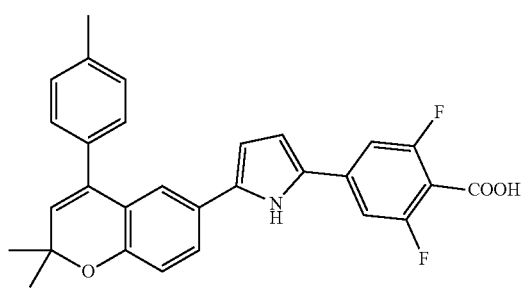

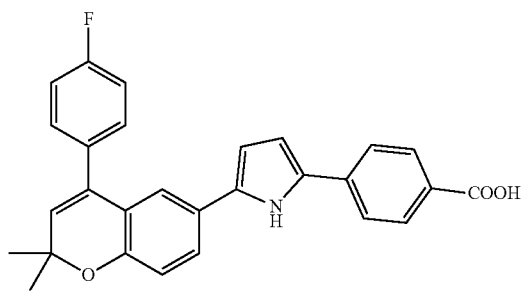

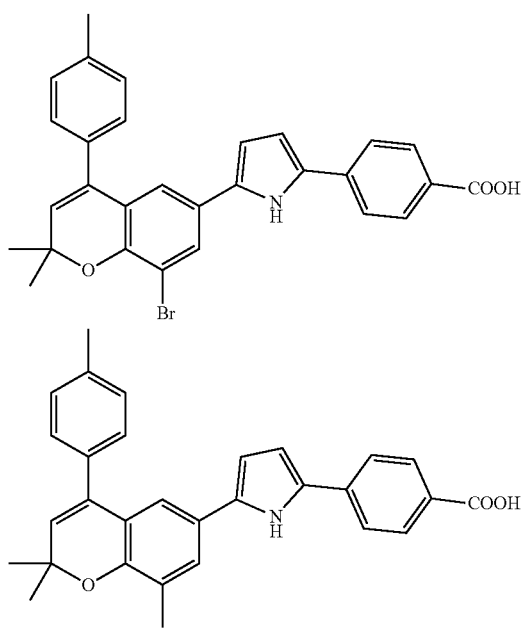

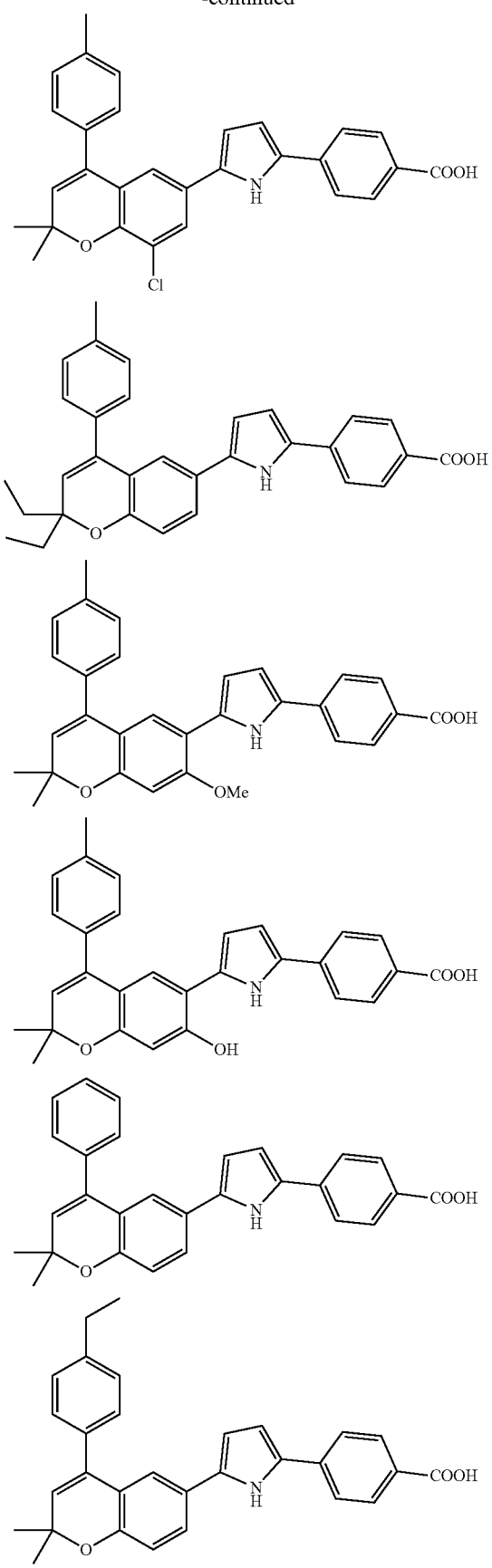
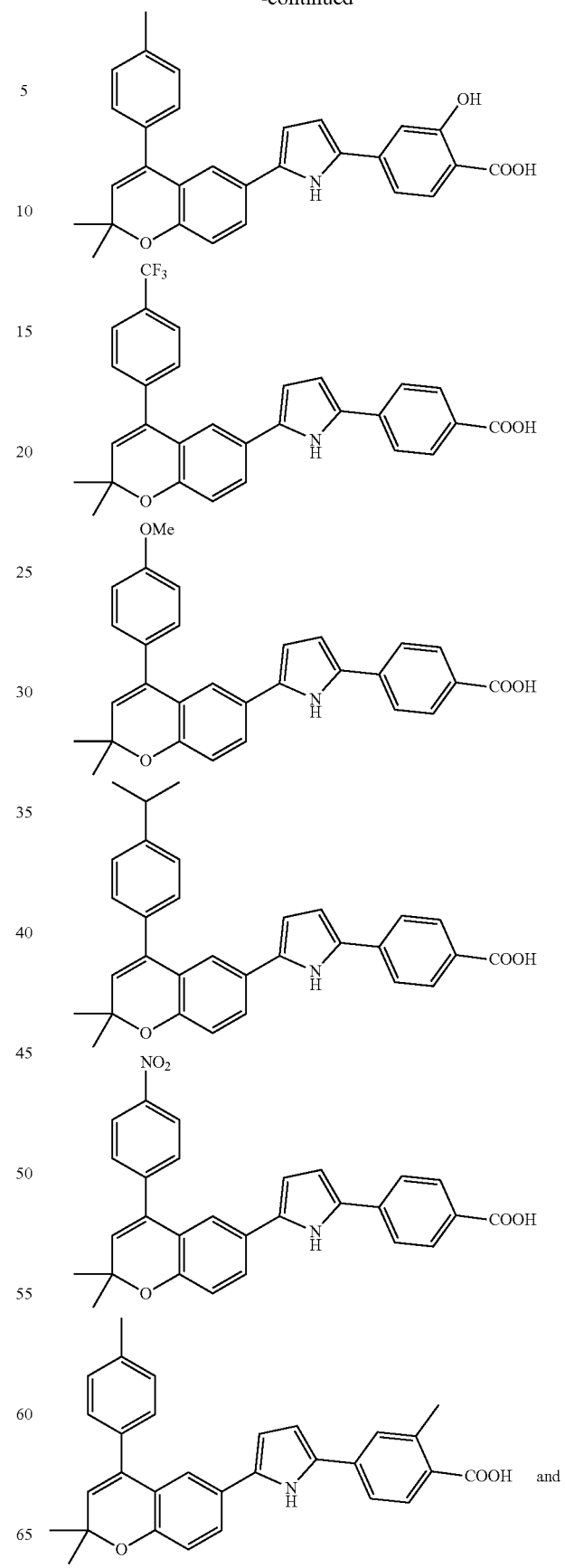

-continued

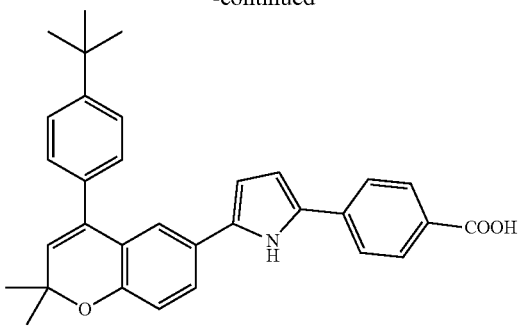

and pharmaceutically acceptable salts thereof.

13. A pharmaceutical composition comprising a compound or pharmaceutically acceptable salt as described in claim 1, and a pharmaceutically acceptable excipient.

14. A compound of the following formula:

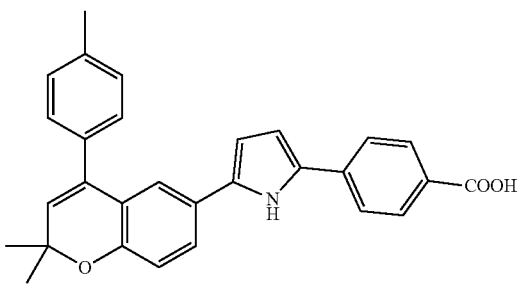

or a pharmaceutically acceptable salt thereof.

15. A pharmaceutical composition comprising the compound as described in claim 14 or a pharmaceutically acceptable salt thereof, and a pharmaceutically acceptable excipient.

16. The pharmaceutically acceptable salt of claim 14, which is:

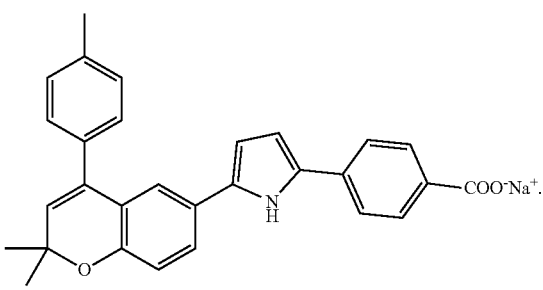

17. A pharmaceutical composition comprising the pharmaceutically acceptable salt as described in claim 16 and a pharmaceutically acceptable excipient.

* * * * *